United States Patent
Ahmad et al.

(10) Patent No.: US 10,736,548 B2
(45) Date of Patent: Aug. 11, 2020

(54) KETONE MEASUREMENT SYSTEM FOR MONITORING MEDICAL CONDITIONS

(71) Applicant: Invoy Holdings, LLC, Aliso Viejo, CA (US)

(72) Inventors: Lubna Ahmad, Chandler, AZ (US); Salman Ahmad, Chandler, AZ (US)

(73) Assignee: Invoy Holdings, Inc., Irvine, CA (US)

( * ) Notice: Subject to any disclaimer, the term of this patent is extended or adjusted under 35 U.S.C. 154(b) by 0 days.

(21) Appl. No.: 15/598,663

(22) Filed: May 18, 2017

(65) Prior Publication Data

US 2017/0332951 A1     Nov. 23, 2017

Related U.S. Application Data

(60) Provisional application No. 62/338,312, filed on May 18, 2016.

(51) Int. Cl.
*A61B 5/08*     (2006.01)
*A61B 5/145*    (2006.01)
(Continued)

(52) U.S. Cl.
CPC ............ *A61B 5/14507* (2013.01); *A61B 5/08* (2013.01); *A61B 5/082* (2013.01); *A61B 5/093* (2013.01); *A61B 5/0935* (2013.01); *A61B 5/145* (2013.01); *A61B 5/14532* (2013.01); *A61B 5/14539* (2013.01); *A61B 5/14551* (2013.01); *A61B 5/4836* (2013.01); *A61B 5/7275* (2013.01);
(Continued)

(58) Field of Classification Search
CPC ............ G01N 33/64; G01N 2010/0087; A61B 2010/0087
See application file for complete search history.

(56) References Cited

U.S. PATENT DOCUMENTS

| | | |
|---|---|---|
| 4,147,514 A | 4/1979 | Magers et al. |
| 4,844,867 A | 7/1989 | Bather |

(Continued)

FOREIGN PATENT DOCUMENTS

| | | |
|---|---|---|
| EP | 1 524 522 | 4/2005 |
| WO | WO 03/039367 | 5/2003 |

(Continued)

OTHER PUBLICATIONS

Ahmad, L. et al., "Design of a Breath Ketone Sensor for Obesity Management", Poster Presentation, Fall Meeting of the Biomedical Engineering Society, 2004, in 3 pages.

(Continued)

*Primary Examiner* — Etsub D Berhanu
(74) *Attorney, Agent, or Firm* — Knobbe, Martens, Olson & Bear, LLP

(57) ABSTRACT

A portable system is provided for measuring a ketone, such as an acetone, in the breath or other bodily fluid of a user. The system includes a portable measurement device that analyzes fluid samples and generates corresponding ketone measurements. The portable measurement device communicates with an application which runs on a smartphone or other mobile device of the user. The application tracks, and generates graphs of, the ketone measurements, and may include various features for facilitating the analysis of the measurements.

27 Claims, 40 Drawing Sheets

(51) Int. Cl.

| | |
|---|---|
| *A61B 5/093* | (2006.01) |
| *A61B 5/1455* | (2006.01) |
| *A61B 5/00* | (2006.01) |
| *G01N 33/497* | (2006.01) |
| *G16H 20/60* | (2018.01) |
| *G16H 50/20* | (2018.01) |
| *G16H 40/63* | (2018.01) |

(52) U.S. Cl.
CPC .......... *G01N 33/497* (2013.01); *G16H 20/60* (2018.01); *G16H 40/63* (2018.01); *G16H 50/20* (2018.01)

(56) References Cited

U.S. PATENT DOCUMENTS

| | | | |
|---|---|---|---|
| 4,931,404 A | 6/1990 | Kundu | |
| 4,970,172 A | 11/1990 | Kundu | |
| 5,071,769 A | 12/1991 | Kundu et al. | |
| 5,174,959 A | 12/1992 | Kundu et al. | |
| 5,465,728 A | 11/1995 | Phillips | |
| 5,474,552 A * | 12/1995 | Palti ............... | A61M 5/1723 |
| | | | 604/67 |
| 5,834,626 A | 11/1998 | De Castro et al. | |
| 6,010,459 A | 1/2000 | Silkoff et al. | |
| 6,067,989 A | 5/2000 | Katzman | |
| 6,190,858 B1 | 2/2001 | Persaud | |
| 6,206,837 B1 | 3/2001 | Brugnoli | |
| 6,221,026 B1 | 4/2001 | Phillips | |
| 6,234,006 B1 | 5/2001 | Sunshine et al. | |
| 6,254,547 B1 | 7/2001 | Phillips | |
| 6,454,723 B1 | 9/2002 | Montagnino | |
| 6,540,691 B1 | 4/2003 | Phillips | |
| 6,582,376 B2 | 6/2003 | Baghdassarian | |
| 6,599,253 B1 | 7/2003 | Baum et al. | |
| 6,607,387 B2 | 8/2003 | Mault | |
| 6,609,068 B2 | 8/2003 | Cranley et al. | |
| 6,629,934 B2 | 10/2003 | Mault et al. | |
| 6,658,915 B2 | 12/2003 | Sunshine et al. | |
| 6,726,637 B2 | 4/2004 | Phillips | |
| 6,841,391 B2 | 1/2005 | Lewis et al. | |
| 6,981,947 B2 | 1/2006 | Melker | |
| 7,052,854 B2 | 5/2006 | Melker et al. | |
| 7,104,963 B2 | 9/2006 | Melker et al. | |
| 7,220,387 B2 | 5/2007 | Flaherty et al. | |
| 7,300,408 B2 | 11/2007 | Hancock et al. | |
| 7,364,551 B2 | 4/2008 | Allen et al. | |
| 7,533,558 B2 | 5/2009 | Flaherty et al. | |
| 7,794,994 B2 | 9/2010 | Cranley et al. | |
| 7,837,936 B1 | 11/2010 | Martin | |
| 7,920,998 B2 | 4/2011 | Brown | |
| 7,976,467 B2 | 7/2011 | Young et al. | |
| 8,021,308 B2 | 9/2011 | Carlson et al. | |
| 8,036,708 B2 | 10/2011 | Oozeki | |
| 8,286,088 B2 | 10/2012 | Shaffer et al. | |
| 8,287,454 B2 | 10/2012 | Wolpert et al. | |
| 8,342,178 B2 | 1/2013 | Hengstenberg et al. | |
| 8,399,837 B2 | 3/2013 | Robbins et al. | |
| 8,514,086 B2 | 8/2013 | Harper et al. | |
| 8,680,974 B2 | 3/2014 | Meiertoberens et al. | |
| 8,816,862 B2 | 8/2014 | Harper et al. | |
| 8,848,189 B2 | 9/2014 | Atkin et al. | |
| 8,871,521 B2 | 10/2014 | Akers, Jr. | |
| 8,917,184 B2 | 12/2014 | Smith et al. | |
| 9,170,225 B2 | 10/2015 | Dutta et al. | |
| 9,173,595 B2 | 11/2015 | Böhm et al. | |
| 9,341,632 B1 | 5/2016 | Ahmad et al. | |
| 9,486,169 B1 | 11/2016 | Ahmad | |
| 9,643,186 B1 | 5/2017 | Ahmad et al. | |
| 2003/0008407 A1* | 1/2003 | Fu ................... | A61B 5/082 |
| | | | 436/161 |
| 2003/0208113 A1* | 11/2003 | Mault ............... | A61B 5/14532 |
| | | | 600/316 |
| 2003/0208133 A1* | 11/2003 | Mault ............... | A61B 5/0002 |
| | | | 600/532 |
| 2004/0018114 A1 | 1/2004 | Wang et al. | |
| 2005/0084921 A1* | 4/2005 | Cranley ............... | C12N 9/0006 |
| | | | 435/25 |
| 2006/0122270 A1* | 6/2006 | Henderson ........... | A61K 31/12 |
| | | | 514/546 |
| 2007/0245810 A1 | 10/2007 | Carter et al. | |
| 2007/0258894 A1 | 11/2007 | Melker et al. | |
| 2008/0008666 A1 | 1/2008 | Phillips | |
| 2008/0053194 A1 | 3/2008 | Ahmad | |
| 2008/0234553 A1 | 9/2008 | Urman et al. | |
| 2009/0054799 A1 | 2/2009 | Vrtis et al. | |
| 2010/0301197 A1 | 12/2010 | Boyle | |
| 2011/0028091 A1 | 2/2011 | Higgins et al. | |
| 2011/0098590 A1 | 4/2011 | Garbutt et al. | |
| 2012/0071737 A1 | 3/2012 | Landini et al. | |
| 2012/0295595 A1 | 11/2012 | Gibori et al. | |
| 2013/0231711 A1 | 9/2013 | Kaib | |
| 2013/0253358 A1 | 9/2013 | Phillips | |
| 2014/0121487 A1* | 5/2014 | Faybishenko ........ | A61B 5/14507 |
| | | | 600/365 |
| 2014/0262830 A1* | 9/2014 | Cha .................. | C12Q 1/006 |
| | | | 205/777.5 |
| 2014/0276100 A1 | 9/2014 | Satterfield et al. | |
| 2014/0364758 A1* | 12/2014 | Schindhelm ......... | A61B 5/082 |
| | | | 600/531 |
| 2014/0366610 A1 | 12/2014 | Rodriguez | |
| 2015/0073233 A1 | 3/2015 | Rich et al. | |
| 2015/0168307 A1 | 6/2015 | Kück et al. | |
| 2015/0289782 A1 | 10/2015 | Peverall et al. | |
| 2016/0146779 A1 | 5/2016 | Gallagher et al. | |
| 2016/0150995 A1 | 6/2016 | Ratto et al. | |

FOREIGN PATENT DOCUMENTS

| | | |
|---|---|---|
| WO | WO 03/039483 | 5/2003 |
| WO | WO 2005/082234 | 9/2005 |
| WO | WO 2010/094967 | 8/2010 |
| WO | WO 2011/104567 | 9/2011 |
| WO | WO 2015/134390 | 9/2015 |

OTHER PUBLICATIONS

Barnett, D. et al., "Breath acetone and blood sugar measurements in diabetes", Clinical Science, vol. 37 (1969), in 1 page.

"CMS Operator Guide", CMS Operator Training 0108, dated Apr. 19, 2002, in 10 pages. URL: http://www.buydraegertubes.com/ds/cms-ops-guide.pdf.

Crofford, O. et al., "Acetone in Breath and Blood", Transactions of the American Clinical and Climatological Association, vol. 88 (1977), in 12 pages.

Diskin, A. et al., "Time variation of ammonia, acetone, isoprene and ethanol in breath: a quantitative SIFT-MS study over 30 days", Physiological Measurement, vol. 24 (2003), in 13 pages.

Dräger CMS Production Information (document properties of document indicate that the document was created on Dec. 1, 2008), in 4 pages. URL: http://www.draeger.com/sites/assets/PublishingImages/Products/cin_chip_measurement_system/US/cms-ds-pi-9044337-en-us.pdf.

DrägerTubes & Accuro Pump Production Information (document properties of document indicate that the document was created on Nov. 11, 2008), in 4 pages. URL: http://www.draeger.com/sites/assets/PublishingImages/Products/cin_accuro/US/081209-pi-DetectorTubes-22-10-2008-en-pdf.

Dubowski, K. et al., "Response of Breath-Alcohol Analyzers to Acetone: Further Studies", Journal of Analytical Toxicology, vol. 8, Sep./Oct. 1984, in 4 pages.

Gervais, T. et al., "Mass transport and surface reactions in microfluidic systems", Chemical Engineering Science, vol. 61 (2006), in 20 pages.

Ketonix US, "Ketonix 2015 Blue Specifications", 2015, in 2 pages. URL:https://www.ketonix.com/index.php/product-2/ketonix-2015-blue.

Ketonix, "Ketonix data for Michel Lundell", 2015, in 1 page. URL: https://www.ketonix.com.

(56) References Cited

OTHER PUBLICATIONS

Khan, A. et al. "Evaluation of a bedside blood ketone sensor: the effects of acidosis, hyperglycaemia and acetoacetate on sensor performance", Diabetic Medicine, vol. 21 (2004), in 5 pages.

Kundu, S. et al., "Breath Acetone Analyzer: Diagnostic Tool to Monitor Dietary Fat Loss", Clinical Chemistry, vol. 39 (1993), in 6 pages.

Kundu, S. K. et al., "Novel Solid-Phase Assay of Ketone Bodies in Urine", Clinical Chemistry, vol. 37 (1991), in 5 pages.

Kupari, M. et al., "Breath Acetone in Congestive Heart Failure", The American Journal of Cardiology, vol. 76, Nov. 15, 1995, in 3 pages.

Landini, B. et al., "Breath Acetone Concentration Measured Using a Palm-Size Enzymatic Sensor System", IEEE Sensors Journal, vol. 9, Dec. 2009, in 6 pages.

Landini, B. et al., "Effect of Exhalation Variables on the Current Response of an Enzymatic Breath Acetone Sensing Device", IEEE Sensors Journal, vol. 10, Jan. 2010, in 6 pages.

Likhodii, S. et al., "Breath Acetone as a Measure of Systemic Ketosis Assessed in a Rat Model of the Ketogenic Diet", Clinical Chemistry, vol. 48 (2002), in 6 pages.

Loken, S. C., "Breath Acetone and Ketone Metabolism in Obese and Diabetic Mice", Diabetes, vol. 25 (1976), in 1 page.

"Figaro Gas Sensor TGS 822", Figaro Engineering Inc., Mar. 1987, in 10 pages.

"MiniMed 530G System User Guide", Medtronic MiniMed, Inc., 2012, in 312 pages.

Musa-Veloso, K. et al., "Breath acetone is a reliable indicator of ketosis in adults consuming ketogenic meals", The American Journal of Clinical Nutrition, vol. 76 (2002), in 6 pages.

Schwarz, K. et al., "Breath acetone—aspects of normal physiology related to age and gender as determined in a PTR-MS study", Journal of Breath Research, vol. 3 (2009), in 9 pages.

Wang, L. et al., "Nanosensor Device for Breath Acetone Detection", Sensor Letters, vol. 8 (2010), in 4 pages.

Wang, L., "Tailored synthesis and characterization of selective metabolite-detecting nanoprobes for handheld breath analysis", Dissertation Ph. D. Thesis, Stony Brook University, Dec. 2008, in 127 pages.

Yoon, S. et al., "Active control of the depletion boundary layers in microfluidic electrochemical reactors", Lab on a Chip, vol. 6 (2006), in 9 pages.

* cited by examiner

Client

Email

First name

Last name

Profile

Date of birth (YYYY-MM-DD)

Baseline breath acetone

Current weight (lbs.)

Goal weight (lbs.)

AM window start

PM window start

07:00 am

07:00 pm

Sex

Lifestyle

Not Specified

In-Between

Exercise frequency

Exercise intensity

Not Specified

High

Step 1 Receive three (3) user-specific trigger points and add to App

|  | 1 | 2 | 3 |
|---|---|---|---|
| Trigger Point | Drink Soda | Eat Chocolate | Drink Coffee |
| Trigger Point State | At Work | At Night Before Bed | Stressful Work Days |

Step 2 Monitor breath acetone & track when the user specific trigger points occur

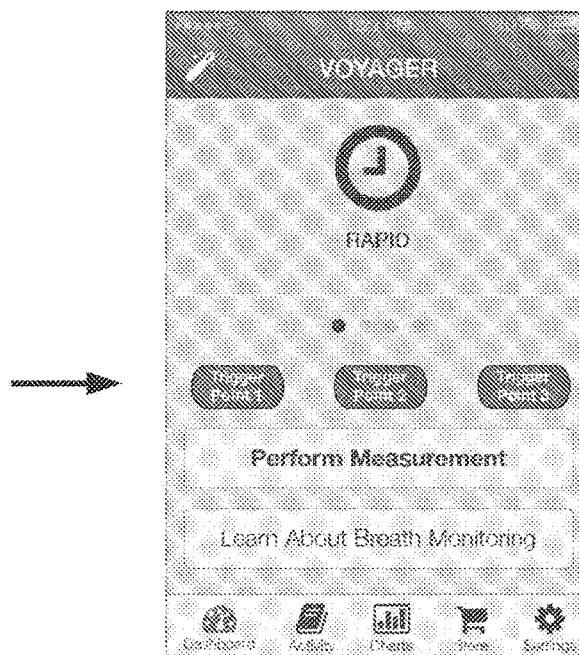

Step 3 After a pattern recognition time period, a pattern is recognized and stored. The App uses the pattern to identify an event that may have occurred that the user may have forgotten or failed to identify

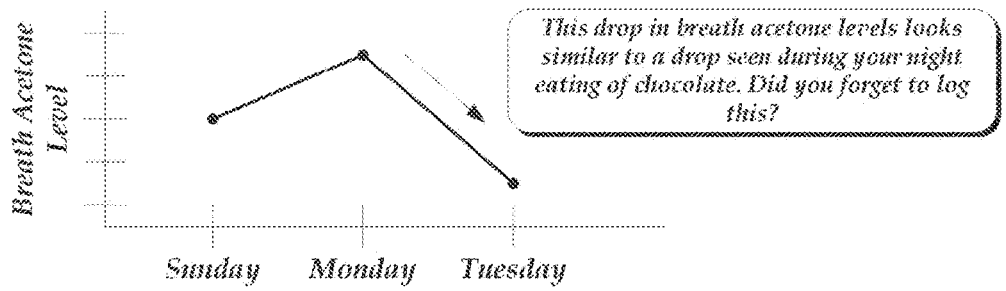

*Fig. 17*

KETONE MEASUREMENT SYSTEM FOR MONITORING MEDICAL CONDITIONS

INCORPORATION BY REFERENCE TO ANY PRIORITY APPLICATIONS

This application claims the benefit of U.S. Provisional Application No. 62/338,312, filed May 18, 2016, which is incorporated by reference herein and is to be considered a part of this specification. Any and all applications for which a foreign or domestic priority claim is identified in the Application Data Sheet as filed with the present application are hereby incorporated by reference under 37 CFR 1.57.

BACKGROUND

Field

The present disclosure relates generally to devices, systems and methods for measuring one or more ketones in one or more body fluids (e.g., blood, urine, breath or some combination of these) or through other means such as the skin, preferably acetone in human breath. It may be used in fields of weight loss, weight management, medical conditions, general health and wellness and in management of ketoacidosis.

Description of the Related Art

Obesity is a major individual and public health concern in the United States and throughout the world. In the United States alone, approximately 33% of the adult population is obese and another 33% are overweight. Treatment of obesity and other weight-related disorders involves a multi-factorial approach (typically a combination of diet, exercise, behavioral health modifications and sometimes medication or surgery) and commonly requires significant and sometimes permanent lifestyle modification. Especially in adults, the oft-required lifestyle changes can make obesity an extremely difficult condition to overcome.

The main goal of obesity management is reducing the amount of fat in the body. For various reasons (to motivate subjects, to enforce compliance and to troubleshoot/customize diets), it is useful and important to have a means to track and trend fat metabolism.

The need for lifestyle changes is not limited to treatment of obesity or overweight. As an example, individuals suffering from other metabolic conditions, such as elevated cholesterol or high blood pressure, may benefit from improving their diet or changing exercise patterns. A growing number of individuals seek to reduce their carbohydrate intake to increase utilization of fat as an energy source, in hopes of reducing their overall insulin usage and thereby counteracting metabolic abnormalities (such as high blood pressure). Other individuals might utilize a low carbohydrate diet to manage other medical conditions, such as cancer and inflammatory diseases.

Athletes and fitness-conscious individuals are concerned about staying in peak physical condition, and are often actively engaged in structured sports activities (whether professional or not). Such individuals struggle with making data-driven decisions about how best to optimize their biochemical and physical condition. They often try to make "smart" decisions about how best to reach their fitness or health goals.

Anorexia nervosa is a psychiatric disorder having substantial implications and is oftentimes a lifelong illness. The disorder is most prevalent in adolescents and young adults, and is 90% more common in young women than men. Because of the complex nature of the disorder and the significant level of mental health treatment, treatment of anorexia nervosa is most effective in-center and is correspondingly expensive. Improving patient outcomes requires considerable counseling and monitoring.

SUMMARY

One aspect of the disclosure provides a system for measuring a ketone in breath of a user. The system comprises a portable measurement device configured to analyze a first breath sample of a user and obtain a first ketone measurement result based on the analysis of the first breath sample. The system further comprises a mobile application configured to run on an electronic device, the mobile application comprising executable instructions that direct the electronic device to at least: display a user interface that comprises an identification of a plurality of conditions that occur on a periodic basis and that affect ketone measurement results, receive a selection of a first condition in the plurality of conditions, receive the first ketone measurement result from the portable measurement device, and update the user interface to display the first ketone measurement result in association with the first condition.

The system of the preceding paragraph can have any sub-combination of the following features: where the executable instructions further direct the electronic device to at least receive the selection of the first condition via an input provided by the user using the user interface; where the executable instructions further direct the electronic device to at least receive the selection of the first condition based on a time of day that the first breath sample is analyzed; where the first condition comprises one of whether the first breath sample is analyzed before or after noon, whether the user ate food before the analysis of the first breath sample and within a first threshold time of the analysis of the first breath sample, whether the user ate food after the analysis of the first breath sample and within the first threshold time of the analysis of the first breath sample, whether the user took medication within a second threshold time of the analysis of the first breath sample, whether the user performed a cardiovascular exercise before the analysis of the first breath sample and within a third threshold time of the analysis of the first breath sample, whether the user performed a cardiovascular exercise after the analysis of the first breath sample and within the third threshold time of the analysis of the first breath sample, whether the user performed a weight bearing exercise before the analysis of the first breath sample and within a fourth threshold time of the analysis of the first breath sample, whether the user performed a weight bearing exercise after the analysis of the first breath sample and within the fourth threshold time of the analysis of the first breath sample, whether the user experienced sleep disruption during a night preceding the analysis of the first breath sample, or whether the user traveled within a fifth threshold time of the analysis of the first breath sample; where the executable instructions further direct the electronic device to at least: update the user interface to request a selection of a state of the first condition to assign to the first ketone measurement result, and receive, via the user interface, a selection of a first state; where the selected first state identifies that the first condition applies to the first ketone measurement result; where the executable instructions further direct the electronic device to at least: update the user interface to request a selection of a state of the first condition to assign to a second ketone measurement result, receive, via the user interface, a selection of a second state, wherein the second state identifies that the first condition does not apply to the second ketone measurement result, receive the second ketone measurement result from the portable measurement device, and update the user interface to display the first ketone measurement result in association with the first condition and the second ketone measurement result in association with an indication that the first condition does not apply; where the user interface further displays baseline ketone measurement results associated with the user; and where the executable instructions further direct the electronic device to at least: modify the first ketone measurement result based on baseline ketone measurement results associated with the user to generate modified first ketone measurement result, and update the user interface to display the modified first ketone measurement result in association with the first condition.

Another aspect of the disclosure provides a computer implemented method. The method comprises generating a first user interface that lists a plurality of ketone tags potentially relevant to a human subject, each ketone tag corresponding to a particular activity or condition that can affect ketone measurements generated from fluid samples from the human subject; receiving, via the first user interface, a selection of a subset of the plurality of ketone tags, the selection being specific to the human subject and corresponding to behaviors of the human subject, the subset omitting one or more of the plurality of ketone tags; generating, by a portable measurement device, a ketone measurement based on a fluid sample generated by the body of the human subject; generating, in connection with the ketone measurement, a second user interface that prompts a user to specify, for each ketone tag in the subset but not for any of the one or more omitted ketone tags, a corresponding ketone tag state corresponding to the measurement; receiving, via the second user interface, data specifying the ketone tag states specified by the user for the subset of ketone tags; and storing the ketone measurement in association with the data specifying the ketone tag states; said method performed under control of program instructions executed by one or more computing devices.

The method of the preceding paragraph can have any sub-combination of the following features: where the second user interface prompts the user to specify, for at least a first ketone tag in the subset, whether the ketone tag applies to the ketone measurement; where the method further comprises using the data specifying the ketone tag states to group the ketone measurement with a plurality of other ketone measurements taken under a common condition, and generating a graph representing ketone measurements taken under the common condition; and where the second user interface is generated prior to generation of the ketone measurement.

Another aspect of the disclosure provides a non-transitory computer readable medium having stored thereon a mobile application comprising executable program instructions that direct a mobile device of a user to at least: receive a selection of a subset of a plurality of ketone tags, each ketone tag corresponding to a particular activity or condition that can affect ketone measurements generated from fluid samples from a human subject, the selection being specific to the human subject and corresponding to behaviors of the human subject, the subset omitting one or more of the plurality of ketone tags; receive, from a portable measurement device, a ketone measurement based on a fluid sample generated by the body of the human subject; generate, in connection with the ketone measurement, a user interface that prompts a user to specify, for each ketone tag in the subset but not for any of the one or more omitted ketone tags, a corresponding ketone tag state corresponding to the measurement; receive, via the user interface, data specifying the ketone tag states specified by the user for the subset of ketone tags; and store the ketone measurement in association with the data specifying the ketone tag states.

The non-transitory computer readable medium of the preceding paragraph can have any sub-combination of the following features: where the user interface prompts the user to specify, for at least a first ketone tag in the subset, whether the ketone tag applies to the ketone measurement; where the executable program instructions further direct the mobile device of the user to at least: use the data specifying the ketone tag states to group the ketone measurement with a plurality of other ketone measurements taken under a common condition, and generate a graph representing ketone measurements taken under the common condition; where the user interface is generated prior to generation of the ketone measurement; where the executable program instructions further direct the mobile device of the user to at least receive the selection of the subset of the plurality of ketone tags based at least in part on a heart rate of the human subject detected by a heart rate monitor; where the fluid sample is one of a breath sample, a blood sample, or a urine sample; where a first ketone tag in the subset comprises one of whether the ketone measurement is measured before or after noon, whether the human subject ate food before the measurement of the ketone measurement and within a first threshold time of the measurement of the ketone measurement, whether the human subject ate food after the measurement of the ketone measurement and within the first threshold time of the measurement of the ketone measurement, whether the human subject took medication within a second threshold time of the measurement of the ketone measurement, whether the human subject performed a cardiovascular exercise before the measurement of the ketone measurement and within a third threshold time of the measurement of the ketone measurement, whether the human subject performed a cardiovascular exercise after the measurement of the ketone measurement and within the third threshold time of the measurement of the ketone measurement, whether the human subject performed a weight bearing exercise before the measurement of the ketone measurement and within a fourth threshold time of the measurement of the ketone measurement, whether the human subject performed a weight bearing exercise after the measurement of the ketone measurement and within the fourth threshold time of the measurement of the ketone measurement, whether the human subject experienced sleep disruption during a night preceding the measurement of the ketone measurement, or whether the human subject traveled within a fifth threshold time of the measurement of the ketone measurement; and where the user interface further displays baseline ketone measurement results associated with the human subject.

BRIEF DESCRIPTION OF THE DRAWINGS

The accompanying drawings, which are incorporated in and constitute a part of the specification, illustrate a presently preferred embodiments and methods of the present disclosure and, together with the general description given above and the detailed description of the preferred embodiments and methods given below, serve to explain the principles of the present disclosure. Of the drawings:

FIG. 7 is a pictorial view of display panels of a software application according to a presently preferred method implementation in accordance with another aspect of the present disclosure.

FIG. 9 provides illustrative inputs for a Settings panel of the software application, display panels for which are shown in FIG. 7.

FIG. 17 is a pictorial diagram that illustrates the inputting of trigger points into a system according to a presently preferred embodiment of another aspect of the present disclosure.

DETAILED DESCRIPTION

Figure 1:
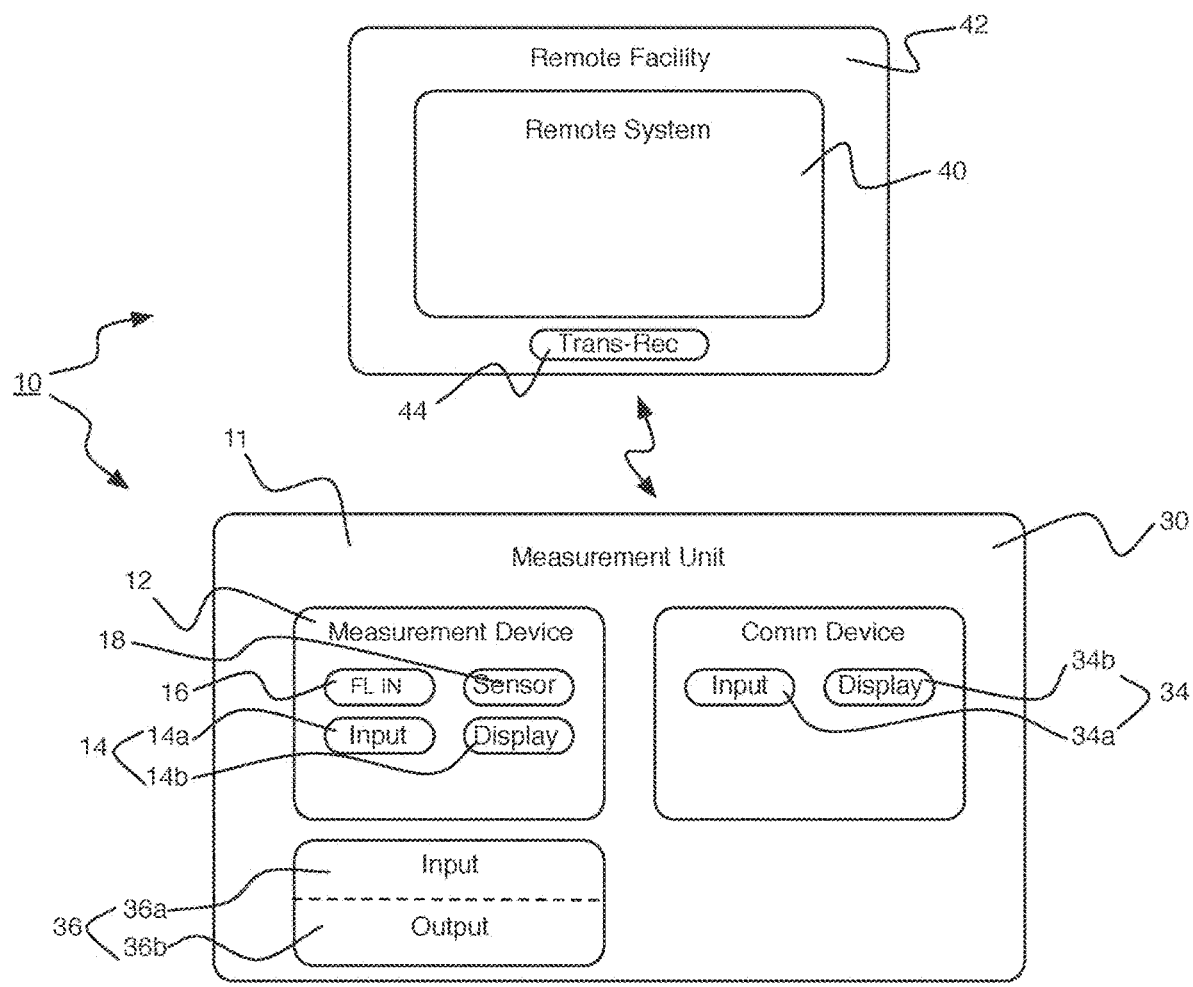
FIG. 1 is a block diagram of a system according to a presently preferred embodiment of the invention according to an aspect.

Reference will now be made in detail to the presently preferred embodiments and methods of the present disclosure as described herein below and as illustrated in the accompanying drawings, in which like reference characters designate like or corresponding parts throughout the drawings. It should be noted, however, that the present disclosure in its broader aspects is not limited to the specific details, representative devices and methods, and illustrative examples shown and described in this section in connection with the preferred embodiments and methods. The present disclosure according to its various aspects is particularly pointed out and distinctly claimed in the attached claims read in view of this specification, and appropriate equivalents.

Ketones are useful to track and trend progress on a fat loss program. Ketone concentrations in the body and in body fluids (e.g., blood, urine, breath, or some combination of these) are correlated with fat metabolism. In the body, three main "ketone bodies" are generated: acetoacetic acid, β-hydroxybutyric acid, and acetone. In the case of acetone, because it is volatile, it is released into alveolar air when the blood brings it in contact with the lungs.

Generally, ketone levels increase in relation to increases in the body's fat metabolism. Higher ketone concentrations indicate greater metabolism of fat. During a net caloric deficit, greater fat metabolism portends increased fat loss (e.g., a primary objective in weight reduction). Measurement of ketones offers the potential to be a powerful and accurate measure of fat metabolism, and therefore provides many advantages in the management of metabolic conditions and obesity management.

Another instance in which breath acetone is useful is monitoring adherence to and efficacy of a low carbohydrate diet for disease management. In the case of diabetes management, individuals with Type 2 diabetes can manage their condition with insulin or they can choose to reduce carbohydrate intake (via a low carbohydrate diet), thereby reducing or eliminating the need for insulin. Taking insulin or various other medications has its own disadvantages and side effects. However, managing Type 2 diabetes via a low carbohydrate diet requires that the patient be compliant and that the diabetes be under control. Measurement of ketones helps to determine the efficacy of a low carbohydrate treatment program and a patient's adherence to it.

Another instance in which measurement of breath acetone is useful is for the management and treatment of Type 1 diabetics. In Type 1 diabetics, where there is insufficient intracellular sugar or where sugar metabolism is impaired, the body resorts to metabolizing fat. This increase in fat metabolism can result in substantial and, in this case, unwanted increases in ketone production. Because ketones are acidic, their build-up in the blood stream can cause a downward shift in blood pH, assuming that the body's ability to buffer pH is compromised or overwhelmed. This can result in a condition called diabetic ketoacidosis. In addressing this phenomenon, the objective is to monitor ketone levels to detect its onset and to aid in its management.

In using breath acetone analysis as a management tool for these and other like applications, it is important that the ketone measurement be reliable. Ideally, ketone concentrations in the blood and in the breath are highly correlated with fat metabolism and correspondingly ketone generation in the liver, so that breath acetone measured in exhaled breath is an accurate proxy.

The present inventor(s) has discovered that a certain level of variability not infrequently arises in making breath ketone measurements and in related analyses. A number of variables can affect the correlation between the breath-measured ketone levels and fat metabolism.

Another concern is patient or user compliance with the weight management program, and the related concern that ketone measurements may be a reflection of patient non-compliance with the program rather than with actual metabolic phenomena.

Traditional compliance with a weight management program has been monitored through the patient's or user's maintenance of a journal. Each day over the course of the program, the user records in the journal the details of food and beverage consumption, including, for example, what was eaten, when, how much, and/or the like.

This journaling approach, however, is unreliable and otherwise problematic, for example, in that it imposes a requirement on the user for his or her timely and accurate recordation. In some cases there also may be a risk of intentional concealment of non-compliance (colloquially called "cheating").

Accordingly, there is a need for ketone measurement devices, systems and methods that accurately measure and report metabolic processes relating to fat, that decrease the vulnerability to user non-compliance and other aberrant factors, and that decrease the likelihood of intentional or willing user non-compliance.

The present disclosure comprises methods, systems, and devices that use ketone, such as ketones found in bodily fluids (e.g., blood, urine, breath, combinations of these, etc.) or detected via permeation or measurement through the skin, in conjunction with novel software, algorithms, and processes to improve measurement results and correspondingly weight management program results. These methods, systems, and devices can facilitate user compliance, provide more lucid and relevant measurement information and feedback to the user and supportive third parties, and limit or prevent unwanted masking of data. Improved health outcomes can be achieved by incorporating a ketone measurement system that affords a robust novel method for tracking user behavior, correlating behavior with the ketone levels to generate user-specific feedback, and reporting this feedback to the user and/or his or her healthcare provider in a novel, highly-useful and less ambiguous fashion.

For simplicity, the ketone measurement system is described herein as a breath acetone measurement system that includes a breath acetone measurement device that measures acetone in breath. The breath acetone measurement system may further include a mobile communications device that executes an application and communicates with the breath acetone measurement device to provide the functionality described below. However, this is not meant to be limiting. The ketone measurement system described herein can include a ketone measurement device that measures any number of different types of ketones (including, for example, acetone) in any number of different types of body fluids (including, for example, blood, urine, breath, and/or any combination of these) or via permeation through the skin. The ketone measurement device may interact with the mobile communications device in the same or similar manner as described herein with respect to the breath acetone measurement device.

The methods, systems, and devices described herein can be used to motivate favorable behavioral changes related to weight loss in a user on a treatment program. Various treatment programs may be used with these methods. Examples include calorie-restricted diets, diets with fixed macronutrient composition (e.g., low carbohydrate diets or high protein diets), cardiovascular exercise, weight bearing or resistance exercise, administering pro-lipolytic medications, administering weight loss drugs, and combinations thereof.

When attempting to control a user's diet or weight (e.g., for weight management, diabetic ketoacidosis ("DKA") monitoring or prevention, etc.), it may be common for certain rules to be set regarding the user's activities. The rules may be set by a third party using a browser (e.g., a web browser) executing on an electronic device, a network-accessible application (e.g., an application executing on a server), and/or the like. For example, the third party may use the browser to log into a network or web-based application or server (e.g., via a content page) that allows the third party to view, create, select, and/or set rules. Some of these rules may relate to the user's diet. Others may relate to the breath acetone measurement regime. In each instance and for each subject matter, there may be favored, disfavored, and prohibited items. Examples of dietary rules are provided in Table 1, and examples of acetone measurement-related rules are provided in Table 2.

TABLE 1

| Examples of Dietary Rules | | | |
|---|---|---|---|
| Subject Matter | Permitted | Disfavored | Prohibited |
| Foods | | | |
| Carbohydrates | | More than 50 grams per day | |
| Protein | | More than 100 grams per day | |
| Beverages | | | |
| Water | Unlimited | | |
| Soft Drinks | | | No soft drinks |

TABLE 1-continued

Examples of Dietary Rules

| Subject Matter | Permitted | Disfavored | Prohibited |
|---|---|---|---|
| Alcoholic Beverages | | | No alcoholic beverages |
| Energy Drinks | | One 12 oz. energy drink per week | |
| Meal or Eating Times | | | |
| Eating after 7 pm | | | No eating after 7 pm |

TABLE 2

Examples of Acetone Measurement-Related Rules

| Subject Matter | Permitted | Disfavored | Prohibited |
|---|---|---|---|
| Time of Day | Test each morning before food or beverages other than water; and each afternoon between 4 pm and 5 pm, no food of beverages other than water for two hours before the test. | | |
| Medication | Perform measurement reading at least two hours before medication. | | |
| Exercise | | Perform measurement reading at least two hours before exercise. | |

The effectiveness of a program can be significantly impacted by the extent to which the user complies with the program rules. Infrequent or poorly controlled compliance with acetone measurement rules or protocols can create interpretation challenges regarding measurement results, which in turn detracts from straightforward and simple use by the user himself or herself. Conversely, where the user faithfully complies with these rules, valuable data and feedback can be provided throughout the program and program success can be greatly improved.

The benefits of ketone measurement in addressing weight management, and in managing such concerns as diabetic acidosis, are highlighted herein above. The benefits can be even more pronounced when the measurement is of breath acetone, as opposed to measurement of blood or urine ketone concentration. Breath measurement avoids the often unpleasant need to draw a blood sample or collect a urine sample, and of handling the samples. The relative ease, speed, and convenience of breath acetone measurement also facilitates user compliance. Ketone measurement in general, and breath acetone measurement in particular, can provide important progress updates and encouragement to a user during the course of a program, which in turn can help to motivate the user not only to adhere to or comply with the program, but also to the ketone monitoring regime.

Even with breath acetone measurement, however, motivating behavioral changes in a user, especially regarding adherence to a program, often poses a significant challenge. With users who are severely overweight, for example, certain adverse behaviors that are causally related to their weight challenges may have become habitual and difficult to change. This is not to say that all overweight users can control weight via behavior modification, but rather that, for a large subset of users, certain events and/or foods trigger behavior that lends itself to weight gain. Examples of such behavior include eating high caloric food, eating unhealthy food, overeating, night eating, etc.

The challenges, but also the potential benefits, of motivating and measuring user compliance with a program and with the associated breath acetone measurement regime are particularly pronounced given the move in the field to private or home administration, as opposed to treatment in a clinical setting. Much of the information available about breath acetone measurements and their interpretation has been obtained in clinical settings, in which the circumstances were controlled. The present applicant believes it is one of the first, if not the first entity, to test ketone measurement, or at least to conduct systematic testing (other than an isolated test or set of tests), in a non-clinical setting, most notably in the user's home or environment, where ketone-impacting variables were not tightly controlled.

As a result of this testing, together with her research and involvement in the field, the present inventor(s) has learned the following:

(1) The timeliness of ketone measurements and the faithfulness of user compliance with certain program rules regarding breath acetone measurement are particularly important to the success of many programs. Specifically pre-calculated reminders and interactions with the user can greatly increase program success.

(2) Certain recurring events or conditions, referred to herein as "acetone tags," arise during the course of a typical program that can confound tracking of the progress on the weight loss program (or other objective such as fitness progress) that is sought to be monitored. If these recurring factors are properly identified and accommodated, their undesirable masking effects can be mitigated or eliminated.

(3) User-specific "trigger points" create unduly high risks of program non-compliance. If these trigger points are identified and managed, the probability and extent of program success is greatly increased.

(4) Computing and making accessible the user's "baseline" acetone levels helps the user create individual-specific goals, ranges, and trends.

Thus, in summary, in the process of monitoring breath acetone levels to assess the effectiveness of a weight management, ketogenic diet, or DKA monitoring or prevention program, the success of this monitoring effort can be greatly improved if one develops a system, method, or device that employs one or more, and preferably all, of the following technologies:

(1) Use selective and interactive reminders and prompts to increase the likelihood of faithful user compliance with the breath acetone measurement regime;

(2) Use acetone tags to limit or prevent certain recurring events from masking true, compliant underlying ketone measurements;

(3) Use one or more trigger points to identify and accommodate non-compliant user activity, and to discourage it; and/or (4) Display or otherwise make accessible user baseline information to promote user-specific progress and to aid in counseling.

Presently preferred embodiments and method implementations according to various aspects of the present disclosure provide these features, in some instances individually and in others collectively, using systems that comprise a breath acetone measurement device and an electronic or communications device in operative communication with the measurement device, operating under the control of or otherwise in conjunction with a software application or "App," that bring these improvements and associated benefits to bear.

System Embodiments

One such system, such as a system 10 as shown in FIG. 1, is provided for measuring a ketone in the breath of a user. System 10, which represents a presently preferred embodiment of the present disclosure, more specifically is designed to conduct multiple measurements over time, and to report those results as more fully described herein below.

System 10 comprises a portable integrated measurement unit 11 that in use would be in the possession of or co-located with a user at a first location.

Measurement unit 11 and the associated electronic or communications device (described herein below) are designed to be used and operated by a "user" (e.g., a dieting person, athlete, patient, etc.) whose ketone concentrations are being measured. It is amenable to home or office use by the user alone, for example, without the presence or assistance of a friend, aid, nurse or clinical staff, etc. Measurement unit 11 and the communications device also are amenable, however, to use by a person other than the user whose ketones are being measured, for example, such as a coach, trainer, doctor, nurse, clinical technician, family member, friend and/or the like, and rather than the user's home or workplace, measurement unit 11 and the communications device may be located at other locations (e.g., a gym, a diet treatment center, a treating physician's office, a clinic, a laboratory, hospital, and/or the like). Thus, although the user is the person whose ketone levels are being measured, the "user" may or may not also be the person who performs the manual commands and operations using unit 11 and/or the electronic or communications device. For simplicity and ease of illustration, throughout the detailed description section in this document, the user is assumed to be both the person whose ketones are measured and the operator of the measurement unit and communications device are the same, even though this may not be and need not be the case in a given instance or application of the system, unless indicated otherwise.

The "first location" preferably comprises a location at which a user of the system, such as the user whose ketone levels are being measured, is located. Given the fact that the user-based unit 11 is portable, it typically would be located with the user or users, or at a location that is readily available to the user or users, such as the user's or users' home or workplace. Unit 11 could, however, be kept in the user's or users' vehicle, purse, backpack, and/or the like. This first location also could comprise a treatment facility, such as a treating physician's office, hospital, outpatient clinic, and/or the like.

Unit 11 comprises a breath ketone measurement device 12 that measures the concentration of the ketone or ketones of interest within the user's breath sample. Ketones of interest in breath typically are limited to acetone, which usually is the only ketone that has a sufficiently low molecular weight to exist in the gas phase or is sufficiently volatile at both standard temperature and pressure and at those found in the pulmonary tissues, alveolar spaces, upper airways, and exhaled breath. In other embodiments, this unit 11 may be or comprise a blood or urine ketone measurement device, such as those disclosed in U.S. patent application Ser. No. 14/690,756, filed Apr. 20, 2015, which is hereby incorporated by reference in its entirety as if fully set forth herein.

Sensor system 18 is designed to analyze the fluid and measure the concentration of the ketone or ketones of interest in the fluid, and to generate a measurement signal that is representative or indicative of the measurement result (e.g., here the ketone concentration in the fluid). Appropriate sensor systems include, without limitation, colorimetric sensors, enzymatic and electrochemical sensors, thermal and thermoelectric sensors (e.g., thermopile sensors), nanoparticle or metal oxide-based sensors, and so on. Examples of colorimetric sensors are provided in U.S. Provisional Application No. 61/800,081, filed Mar. 15, 2013, which is hereby incorporated by reference in its entirety as if fully set forth herein. Examples of metal oxide or nanoparticle sensors are provided in U.S. patent application Ser. No. 13/052,963, filed Mar. 21, 2011, which is hereby incorporated by reference in its entirety as if fully set forth herein. Other examples of sensors are provided in U.S. Pat. No. 6,609,068, filed Mar. 5, 2001, and U.S. Pat. No. 7,364,551, filed Apr. 15, 2004, which are hereby incorporated by reference in their entirety as if fully set forth herein. Another example of sensors is provided in U.S. Patent Application No. 62/290,632, filed Feb. 3, 2016, which is hereby incorporated by reference in its entirety as if fully set forth herein.

Measurement device 12 receives a sample of the user's breath and measures acetone in the breath sample to ascertain the presence and preferably the concentration or concentration range of the acetone in that sample. The term "measure" or, equivalently, "sense," as used herein, may comprise analysis to ascertain or detect a specific concentration of the acetone in the breath sample, or to detect the presence of the acetone above a specified threshold concentration, or to detect whether the concentration of the acetone is within a particular range or ranges, and/or the like.

Measurement device 12 is capable of measuring the concentration of acetone in a breath sample of the system user at concentration ranges, and thus with sensitivity, at which the acetone is present in the breath sample or samples as normally encountered in breath under circumstances for which the measurement is intended to address (e.g., weight management, acidosis monitoring and management, and so on). For measurements in healthy users, for example, the sensitivity range of the measurement device for acetone is within the range of normal acetone levels for healthy users and, for measurements of users with a particular condition (e.g., obesity, with diabetes, metabolic syndrome, etc.), the device sensitivity is within ranges expected to be encountered under those circumstances. Exemplary ranges for weight management programs include 0 parts per million ("ppm") to 10 ppm, 0 ppm to 20 ppm or 0 ppm to 60 ppm, depending on the type of the program. In general, the more the weight management encourages fat metabolism as the primary source of fuel, the higher the range. For DKA prevention or monitoring programs, an exemplary range is 0 ppm to 200 ppm.

Measurement device 12 optionally may comprise an input device 14*a* for inputting data or information into measurement device 12. Input device 14*a* may comprise a keyboard, mouse, tracking device or another touch-sensitive device, or other device capable of inputting data and information as further described herein. Measurement device 12 also optionally may comprise an output device 14*b* (e.g., a display) for presenting user information and outputting measurement results. Preferably, input device 14*a* and output device 14*b* of unit 11 are integrated in the form of a touch screen display 14. Measurement device may also communicate wirelessly (e.g., via Bluetooth, IEEE 802.11x, etc.) or via a wired connection with the user's portable electronic device (e.g., a wired telecommunications device, a wireless telecommunications device, or a mobile communications device, such as a smart phone, tablet, and/or the like).

Measurement device 12 also comprises a breath sample input 16 and a sensing system 18. Breath sample input 16 is designed to receive a sample of the breath to be analyzed. It typically will differ in design depending on the expected concentration range for the acetone and other factors, for example, as described in U.S. Provisional Application No. 61/800,081, filed Mar. 15, 2013, which is hereby incorporated by reference in its entirety as if fully set forth herein.

Sensing system 18 is designed to analyze the fluid and measure the concentration of the ketone or ketones of interest in the fluid, and to generate a measurement signal that is representative or indicative of the measurement result (e.g., here the ketone concentration in the fluid). Appropriate sensing systems include, without limitation, colorimetric sensors, enzymatic and electrochemical sensors, thermal and thermoelectric sensors such as thermopile sensors, nanoparticle or metal oxide-based sensors, and so on. Examples of colorimetric sensors are provided in U.S. Provisional Application No. 61/800,081, filed Mar. 15, 2013, which is hereby incorporated by reference in its entirety as if fully set forth herein. Examples of metal oxide or nanoparticle sensors are provided in U.S. patent application Ser. No. 13/052,963, filed Mar. 21, 2011, which is hereby incorporated by reference in its entirety as if fully set forth herein. Other examples of sensing systems are provided in U.S. Pat. No. 6,609,068, filed Mar. 5, 2001, and U.S. Pat. No. 7,364,551, filed Apr. 15, 2004, which are hereby incorporated by reference in their entirety as if fully set forth herein.

Unit 11 also comprises an electronic device or, equivalently, a communications device 30. Electronic device 30 is in operative communication with measurement device 12 and is adapted or configured to receive the measurement signal from measurement device 12, or from an associated processor or processing means (described more fully herein below).

Measurement device 12 and electronic device 30 are in operative communication in the sense that they are configured to communicate information in the form of digital data at least from one device to the other and preferably bi-directionally between the two devices, directly or indirectly (e.g., via an intermediate processor). This operative communication may be enabled through a direct connector (such as printed circuit board connector or slot), a docking station, a cable, or wirelessly, as further described herein below. In unit 11, the communication between these devices is via a direct connection (e.g., by being affixed on a common circuit board or adjacent circuit boards with ohmic connection, via a cable, and/or the like).

Electronic device 30 also comprises a capability to transmit the measurement signal, in its raw form or in modified form as further described herein, outwardly from unit 11. Preferably, this outward or external communications capability comprises data receiving capabilities so that electronic device 30 can transmit and receive data bi-directionally, both to and from unit 11, via a wired or wireless connection. Presently preferred embodiments of this outward or external communications feature of electronic device 30 comprise a data modem, a wireless transceiver, or combinations of these. Presently preferred examples of suitable wireless technology include the transmission circuitry and associated software of commercially-available cell phones or "smartphones," Bluetooth transceiver technology, and/or the like.

Alternatively or in addition, however, the communication may comprise a wired connection to a network like the Internet (e.g., via a cable modem) or to another device like the measurement device 12 (e.g., via a USB connection, an Ethernet connection, etc.). Electronic device 30 optionally also may comprise an input device 34a such as a keyboard, keypad, mouse, track ball, touchpad, touch screen, and/or the like, for inputting information or data, and a display 34b (e.g., for displaying user information, data, and/or measurement results). Presently preferred input and display devices may comprise or be combined or associated with a touch screen 34.

In system 10, unit 11 comprises both measurement device 12 and communications device 30, and thus, it is generally preferred that a single input device 36a and a single display 36b are used for both device 12 and device 30. This obviates the need to provide separate input and display devices for each of them, thereby potentially lowering complexity and unit cost. More preferably, and as in unit 11, input device 36a and display 36b are combined in the form of a touch screen 36 that serves both devices 12 and 30.

Unit 11 also optionally may comprise a clock, calendar, and a locating device such as a Global Positioning Satellite (GPS) receiver.

Figure 2:
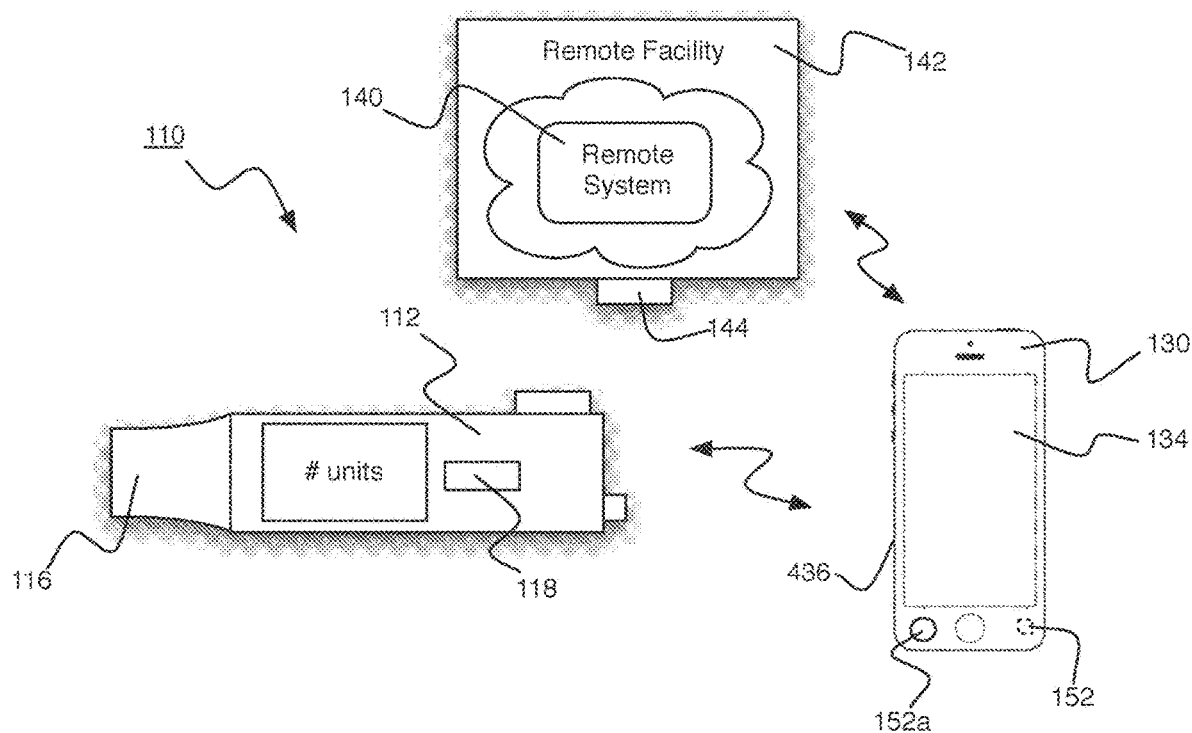
FIG. 2 is a pictorial diagram of another system according to a presently preferred embodiment of the present disclosure according to an aspect.
Figure 3:
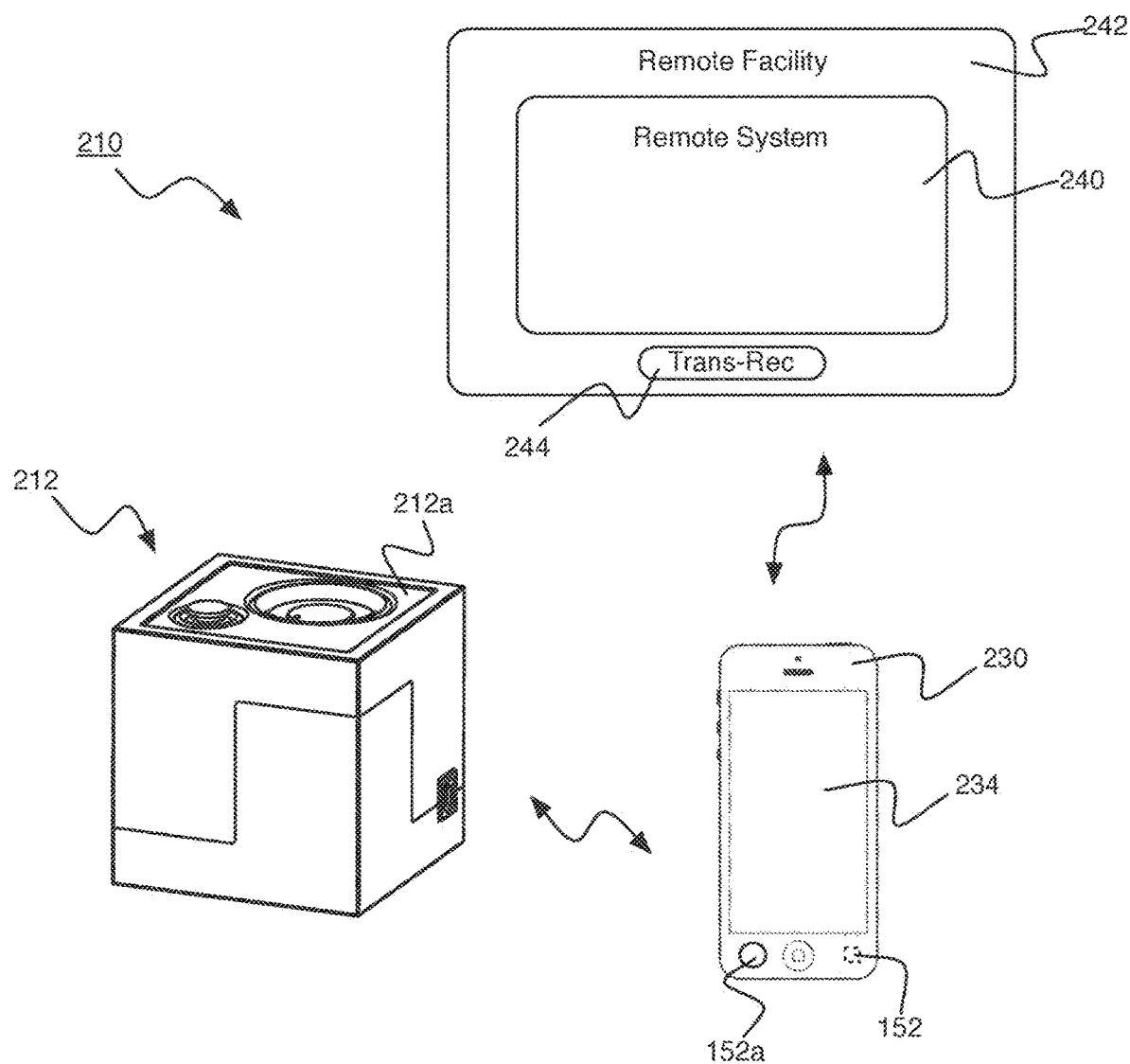
FIG. 3 is a pictorial diagram of another system according to a presently preferred embodiment of the present disclosure according to an aspect.

While unit 11 is depicted as including both the measurement device 12 and the electronic device 30, this is not meant to be limiting. For example, the measurement device 12 and the electronic device 30 may be separate devices and the measurement device 12 and the electronic device 30 may maintain communication with each other via a wired or wireless connection. FIGS. 2-3 depict examples in which the measurement device 12 and the electronic device 30 are separate devices.

System 10 further comprises a remote system 40 disposed at or within a remote facility 42 (also referred to herein as a "center facility 42") at a second location remote from the first location. The distance between the first and second locations may be substantial (e.g., in separate cities, states, provinces, regions, etc.). This is not, however, necessarily the case. In a clinical setting, for example, the first location where unit 11 is located may be in an examination room and remote system 40 may be in a separate room in the same facility.

Remote system 40 may comprise any computer, or system or network of computers, that processes, stores and/or communicates information remotely from any of unit 11, measurement device 12 or communications device 30, as generally described herein. Remote system 40 preferably comprises a general purpose or commercially-available server with appropriate server software and preferably known or commercially-available database software capable of performing the tasks and functions as described herein. Remote system 40 may transmit current information, previous information, information that has been acquired subsequent to the measurement or data of interest, or combinations of these.

Remote system 40 also comprises a transceiver device 44 suitable and appropriate for communications, preferably bi-directional or duplex communications, with communications device 30 of unit 11. Transceiver 44 may comprise any of the technologies described herein above with respect to communications device 30.

Remote facility 42 may comprise a data center, health care facility such as a hospital, clinic, or doctor's office, and/or the like. The location of remote system 40 and remote facility 42, however, need not be fixed, and remote system 40 may be moved to a new location or locations (e.g., from time to time). Remote system 40 also may comprise a distributed network. In presently preferred system designs, remote facility 42 comprises a data center that comprises one or more servers (remote system 40) for storing, managing and inputting and outputting or distributing data as described more fully herein below. This is not, however, limiting. Remote facility 42 may, for example, comprise a set of regional facilities, a distributed data management system with multiple facilities, and the like. Additionally, remote system 40 may either be under the operational control of the user of the system (e.g., system 10), or it may be under the control of a third-party (e.g., a service provider).

In presently preferred embodiments, remote facility 42 comprises a network service or cloud provider that services various customers, and which serves as a portal or repository for the facilities that also may comprise part of the remote facility 42 (e.g., a hospital, clinic, doctor's office, and/or the like).

Remote system 40 comprises a database, for example, such as any one of the several commercially-available database application systems that is configured to store and transmit or receive data as described herein. An example would comprise the types of commercially-available databases that are used to house and manage health records.

With this system 10 as herein described, communications device 30 of unit 11 and remote system 40 are configured to communicate data, preferably but optionally bi-directionally, preferably including the measurement signal and additionally parameter data and population data as described more fully herein below. This communications link, indicated by reference numeral 32, preferably is at least partially wireless and preferably includes an Internet connection or access.

A system 110 according to another presently preferred embodiment of the present disclosure is shown in FIG. 2. System 110 also is configured to measure acetone in the breath of a user, typically in the form of a breath sample.

System 110 comprises a breath analysis or measurement device 112. Presently preferred breath acetone measurement devices are those shown and described in U.S. Provisional Application No. 61/800,081, filed Mar. 15, 2013, U.S. patent application Ser. No. 13/052,963, filed Mar. 21, 2011, and U.S. Pat. No. 6,609,068, filed Mar. 5, 2001, and U.S. Pat. No. 7,364,551, filed Apr. 15, 2004, which are hereby incorporated by reference in their entirety as if fully set forth herein.

Measurement device 112 comprises a breath sample input in the form of a mouthpiece 116, into which the user may blow or exhale directly to input a breath sample. It further comprises a sensing system 118 in fluid communication with input 116 so that the breath sample contacts or interacts with the sensing system, whereupon sensing system 118 measures the concentration of the acetone in the breath sample and generates a measurement signal representative of that acetone concentration. The sensing system may be as described herein above.

Sensing system 118 preferably comprises a metal-oxide nanoparticle-based sensing system, such as those described in U.S. patent application Ser. No. 13/052,963, filed Mar. 21, 2011, which is hereby incorporated by reference in its entirety as if fully set forth herein.

System 110 also comprises an electronic or communications device 130 in operative communication with measurement device 112. In system 110, electronic device 130 comprises a computing device with a wireless link, such as those described in U.S. Provisional Application No. 61/981, 457, which is hereby incorporated by reference in its entirety as if fully set forth herein. Electronic device 130 includes a touch screen 134 for input of data or information and presentation of displays. The electronic device 130 also comprises a processor 152 and storage 152*a*. Moreover, the electronic device 130 is loaded with the App (e.g., instructions that can be executed by a processor that instruct the electronic device 130 to perform processes described herein). Electronic device 130 includes the same communications equipment and features as described herein above with respect to device 130, and is adapted to receive the measurement signal from measurement device 112, preferably wirelessly. Examples of additional computing devices and/or software systems for such computing devices are described in U.S. patent application Ser. No. 14/807,818, filed Jul. 23, 2015, and Ser. No. 15/588,414, filed May 5, 2017, which are hereby incorporated by reference in their entirety as if fully set forth herein.

In other embodiments of the system 110, the measurement device 112 includes a touch screen or other display capable of displaying an interactive user interface. In such embodiments, some or all of the user interface displays described herein (such as those of the App) may instead be provided on the measurement device 112. Further, in these embodiments, the App may run entirely on the measurement device 112 (which may communicated directly with the remote system 140), and the electronic device 130 (e.g., smartphone) may be omitted.

Both measurement device 112 and electronic device 130 are located at a first location which, as previously described, preferably comprises a location at which a user of the system, such as the user whose acetone levels are being measured is located (e.g., at the user's home or workplace).

System 110 further comprises a remote system 140 disposed within a remote facility or center facility 142 at a second location remote from the first location. In system 110, remote system 140 and remote facility 142 are fully equivalent to remote system 40 and remote facility 42 of system 10, shown in FIG. 1 and described herein above.

With connections or communication links as described herein above with respect to breath analysis device 112, electronic device 130 and remote system 140, system 110 is configured to communicate data, preferably but optionally bi-directionally, preferably including the measurement signal and additionally parameter data as described more fully herein.

Figure 4:
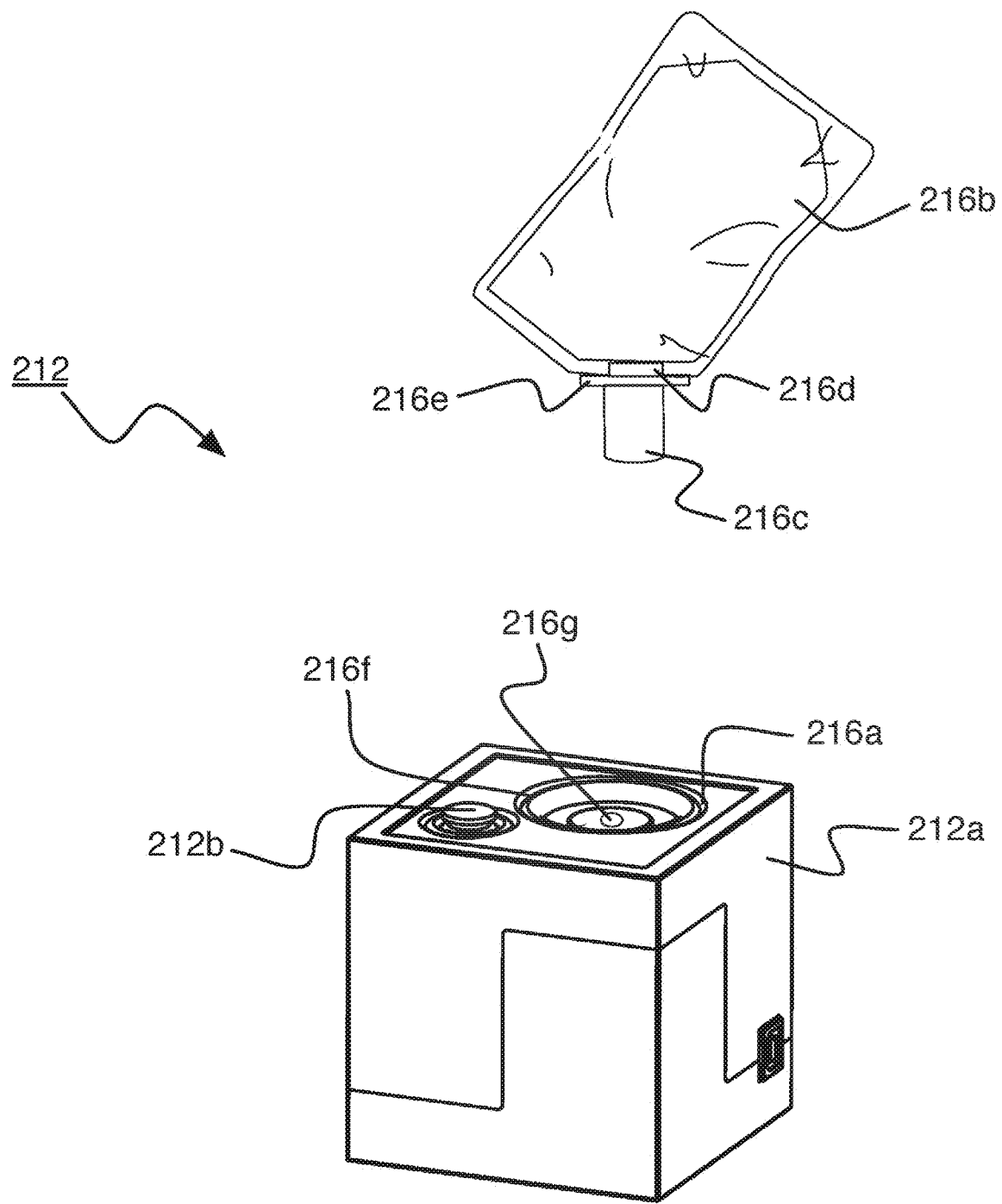
FIG. 4 is an elevated perspective view of a base and breath bag for the system of FIG. 3.
Figure 5:
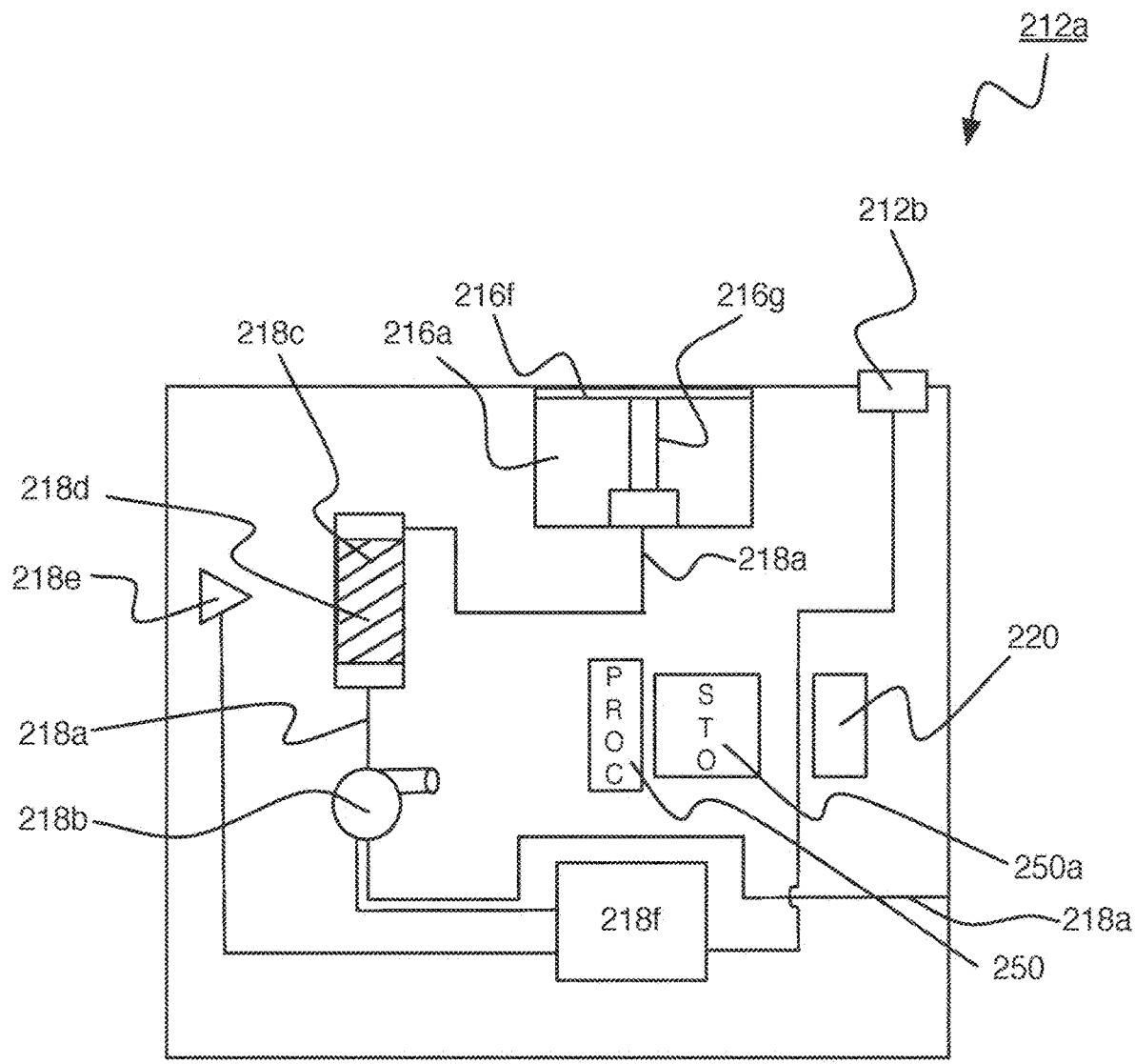
FIG. 5 is a cross sectional cutaway side view of the base shown in FIG. 4.
Figure 6:
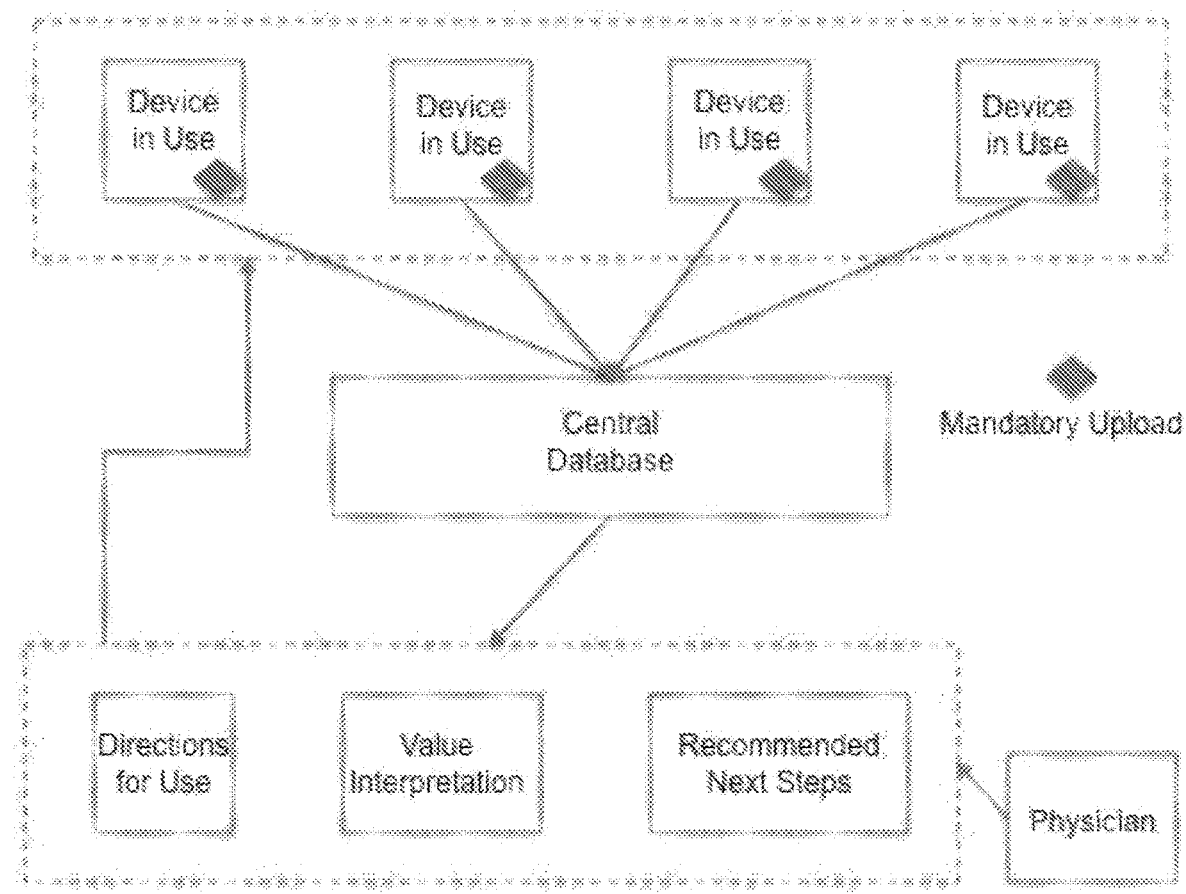
FIG. 6 is a network diagram for the systems of FIGS. 1-3.

A system 210 according to still another presently preferred embodiment of the present disclosure is shown in FIGS. 3-5. System 210 also is configured for measuring acetone in the breath of a user. With reference to FIG. 3, system 210 comprises a breath ketone measurement device 212, an electronic or communications device 230, which in this embodiment comprises the same electronic device as electronic device 130 in system 110 of FIG. 2, and a remote system 240 identical to remote system 140 of system 110 in FIG. 2. The related components and communications links as shown in previous drawing figures and described herein may apply to this system as well, as indicated by the same or like reference numerals. Other than the substitution of a different acetone measurement device, system 210 actually is similar to or exactly the same as system 110 of FIG. 2.

As shown in FIG. 4, breath acetone measurement device 212 of system 210 comprises a base or base unit 212*a*. Base 212*a* comprises a power button 212*b* and an input port 216*a*.

Device 212 further comprises a breath sample bag or breath bag 216*b* that includes a bag mouthpiece and ferrule 216*c* and one-way valve 216*d*. Breath bag 216*b* is a physically separate component relative to base 212a, but is adapted to detachably couple to base 212a by coupling breath bag ferrule 216c into base input port 216a so that they seal in a fluid-tight manner. This coupling preferably is confirmed by a switch that is electrically coupled to a microprocessor. In some embodiments, the breath bag 216b may be omitted; in these embodiments, the user may blow through a cartridge (e.g., using a cartridge holding device or mouthpiece), and then insert the cartridge into the base unit 212a for analysis.

In use, initially breath bag 216b is detached from base 212a and is fully deflated. The user places his or her mouth at the bag mouthpiece 216c and blows into bag 216b to inflate it with a sample of the user's breath. One-way valve 216d allows the breath sample to enter bag 216b, but prevents the breath sample from escaping back out mouthpiece 216c, thus retaining the breath sample in the bag.

The user then places the inflated breath bag 216b onto base 212a by inserting ferrule 216c into base input port 216a. As this mating occurs, one-way valve 216d is pressed onto a post 216g disposed in base input port 216a, which biases a flap in the one-way valve and opens it so that the breath sample is released from the bag 216b and can freely enter base input port 216a.

With reference to FIG. 5, which shows a cross-sectional cutaway side view of base 216a, the breath sample from breath bag 216b, upon entering base 212b through input port 216a, is directed along a flow path 218a under the influence of a pump 218b to the sensing system 218. Sensing system 218 comprises a detachable cartridge 218c that in turn comprises a chemical interactant 218d that reacts with acetone in the breath sample to cause a color or chromatic change in the cartridge that is representative of the concentration of acetone in the breath sample. A camera 218e that is sensitive to the colorimetric or chromatic change senses the change present in the cartridge as a result of the breath sample exposure, and communicates that sensed change as a measurement signal to a sensing system circuit board 218f. Circuit board 218f performs routine signal conditioning and formatting on the measurement signal and communicates it to processor 250, which stores it in storage 250a. Processor 250 then transmits the measurement signal to communications device 230 using transceiver 220 (which is identical to or the equivalent of transceiver 120 in system 110).

Systems 10, 110 and 210 can be used according to presently preferred method implementations to measure the breath acetone levels of a user as illustrated in the following examples. It will be appreciated, however, that the methods are not necessarily limited to conduct using these specific systems, and that variations on those systems and indeed other systems may be used to perform the methods.

Insertion of Detachable Components

In an embodiment, breath analysis devices, such as the breath acetone measurement device 212, include components, referred to herein as presence sensors, that identify or recognize when a detachable, disposable, and/or replaceable accessory component (e.g., breath bag, cartridge, test strip, etc.) is correctly mated with the breath acetone measurement device. Examples of presence sensors may include bump switches, magnetic switches, piezoelectric sensors, proximity sensors (which may include a photodiode), software-coupled image sensors (e.g., a camera that periodically captures an image of a region of interest and processes the image to determine if the detachable component is correctly mated and in place), and/or the like. The presence sensors may also include an electrically conductive material (e.g., a piece of conductive copper tape) that is coupled to the detachable component and that is also embedded within the base unit of the breath acetone measurement device such that when the electrically conductive material and the detachable component are in physical contact with one another, they complete an electrical circuit. The presence sensors may also be a plurality of presence sensors that, alone or in combination, provide more specific guidance to a user (e.g., via a user interface on a mobile application, via a display on a breath acetone measurement device, etc.) on what steps or actions the user may need to perform to correctly couple or insert a detachable component.

The breath acetone measurement devices may also use various sensor systems to generate readings. Sensor systems include, without limitation, colorimetric sensors, enzymatic and electrochemical sensors, thermal and thermoelectric sensors (e.g., thermopile sensors), nanoparticle or metal oxide-based sensors, and/or the like. Examples of colorimetric sensors are provided in U.S. Provisional Application No. 61/800,081, filed Mar. 15, 2013, which is hereby incorporated by reference in its entirety as if fully set forth herein. Examples of metal oxide or nanoparticle sensors are provided in U.S. patent application Ser. No. 13/052,963, filed Mar. 21, 2011, which is hereby incorporated by reference in its entirety as if fully set forth herein. Examples of electrochemical enzyme sensors are provided in U.S. Pat. No. 7,364,551, filed Apr. 15, 2004, and U.S. patent application Ser. No. 12/228,046, filed Aug. 8, 2008, and Ser. No. 13/194,564, filed Jul. 29, 2011, which are hereby incorporated by reference in their entirety as if fully set forth herein. Other examples of sensors are provided in U.S. Pat. No. 6,609,068, filed Mar. 5, 2001, and U.S. Pat. No. 7,364,551, filed Apr. 15, 2004, which are hereby incorporated by reference in their entirety as if fully set forth herein.

Figure 23:
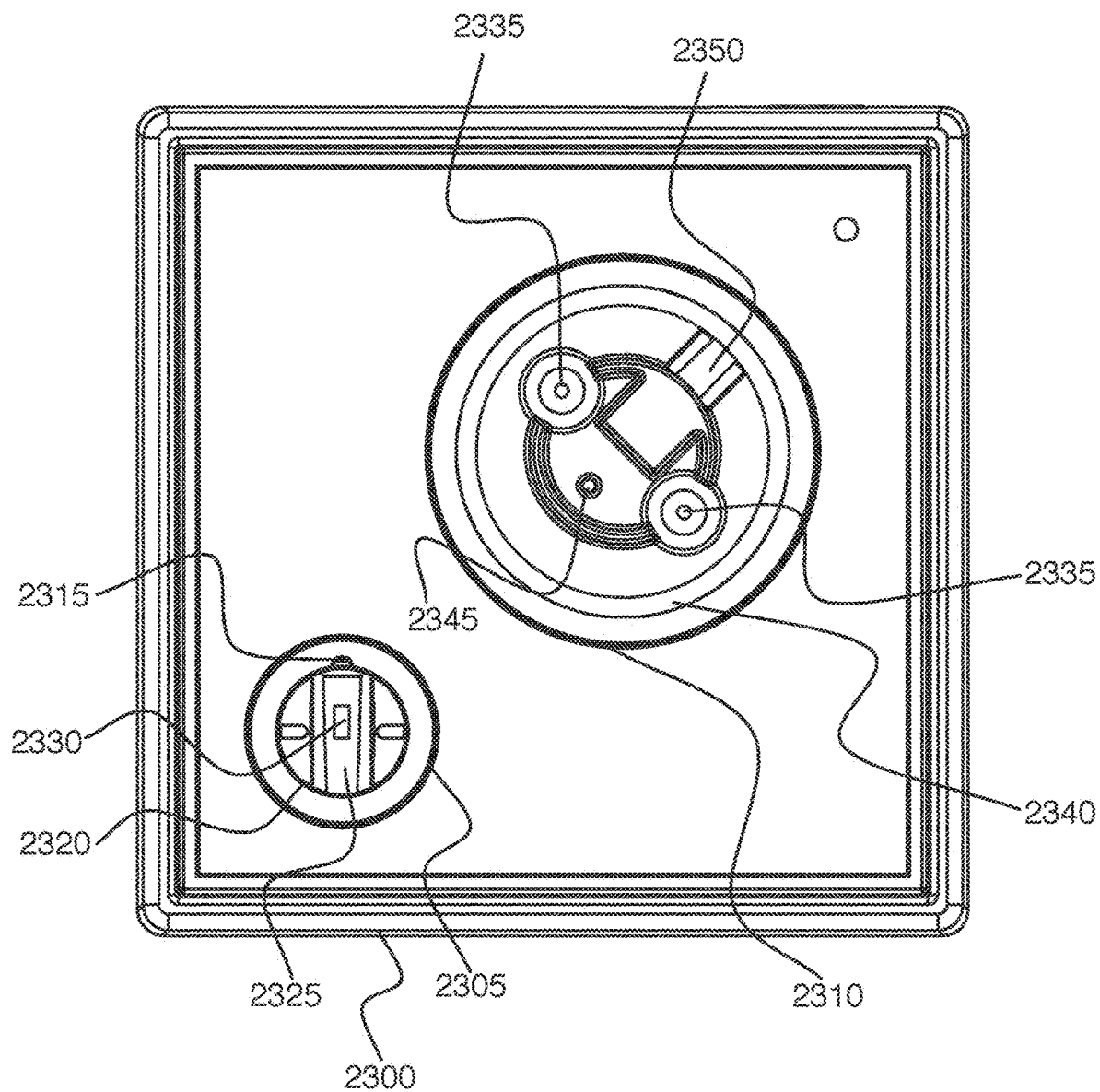
FIG. 23 illustrates a breath acetone measurement device base unit.

FIG. 23 illustrates a breath acetone measurement device base unit 2300. Certain embodiments of breath acetone measurement devices utilize colorimetric sensors, where the color-generating reagents are contained within detachable cartridges, such as within those cartridges disclosed in U.S. patent application Ser. No. 14/206,347, filed Mar. 12, 2014, which is hereby incorporated by reference in its entirety as if fully set forth herein.

In an embodiment, the base unit 2300 includes a cartridge insertion area 2305 and a breath bag insertion area 2310. The cartridge insertion area 2305 may be configured to receive a detachable cartridge. In this embodiment, the cartridge insertion area 2305 includes a key 2315 that may ensure that the cartridge is oriented in a specific physical orientation when inserted into the base unit 2300. The existence of a key may also help ensure that the user positions the cartridge correctly into the base unit 2300.

The cartridge insertion area 2305 may further comprise a presence sensor 2325. For example, the presence sensor 2325 may be a bump switch. The presence sensor 2325 may be disposed such that the protruding portion of switch 2330 is depressed when the cartridge is pressed into position. Thus, the presence sensor 2325 may sense when the mechanical placement of the cartridge or a portion of the cartridge in the cartridge insertion area 2305 is such that the switch 2330 is depressed (e.g., the presence sensor 2325 may sense when the cartridge or a portion of the cartridge fits completely or nearly completely and properly in the cartridge insertion area 2305). The processing unit of the breath acetone measurement device (not shown) may monitor the state of the switch 2330 to determine when the switch 2330 is depressed. Likewise, if the switch 2330 transitions from a depressed state to an undepressed state, the processing unit may detect that the switch 2330 is undepressed. To ensure a strong seal in the flow path of the breath sample, it may be important for the user to press the cartridge all the way into the cartridge insertion area 2305.

It may also be desirable that the presence sensor 2325 be fluidically sealed within the cartridge insertion area 2305 such that the breath sample does not leak or seep into openings between the enclosing plastics of the breath acetone measurement device and the switch 2330. A gasket 2320 may further facilitate the fluidic sealing.

The breath bag insertion area 2310 may be configured to receive a replaceable breath bag. The base unit 2300 may include two prongs 2335 that protrude into the one-way valve of the breath bag when the breath bag is inserted. A gasket 2340 may ensure that the breath sample does not leak or leak above a threshold value. The breath sample may be directed substantially through hole 2345 in the breath bag insertion area 2310. Once the breath bag is in place, bump switch 2350 may be activated (e.g., by being depressed due to the insertion of the breath bag). Thus, the bump switch 2350 serves as a breath bag presence sensor and may sense when the mechanical placement of the breath bag or a portion of the breath bag in the breath bag insertion area 2310 is such that the two prongs 2335 protrude into the one-way valve of the breath bag (e.g., the bump switch 2350 may sense when the breath bag or a portion of the breath bag fits completely or nearly completely and properly in the breath bag insertion area 2310). The bump switch 2350 may also sense when the breath bag is fluidically coupled to the hole 2345 (e.g., fluid may flow between the breath bag and the hole 2345 or other part of the flow path without leaking or substantially leaking into another part of the breath acetone measurement device) based on, for example, the mechanical placement of the breath bag. The processing unit of the breath acetone measurement device may monitor the state of the bump switch 2350. Activation of the bump switch 2350 may cause the processing unit (not shown) to sense that the bump switch 2350 of the breath acetone measurement device is active and that the breath bag is in place. Likewise, if the breath bag is initially in place, but then slips out of place, the bump switch 2350 may be deactivated. The bump switch 2350 thus serves as a breath bag presence sensor. Deactivation of the bump switch 2350 may cause the processing unit to sense that the bump switch 2350 is deactivated and that the breath bag is not in place.

Figure 24:
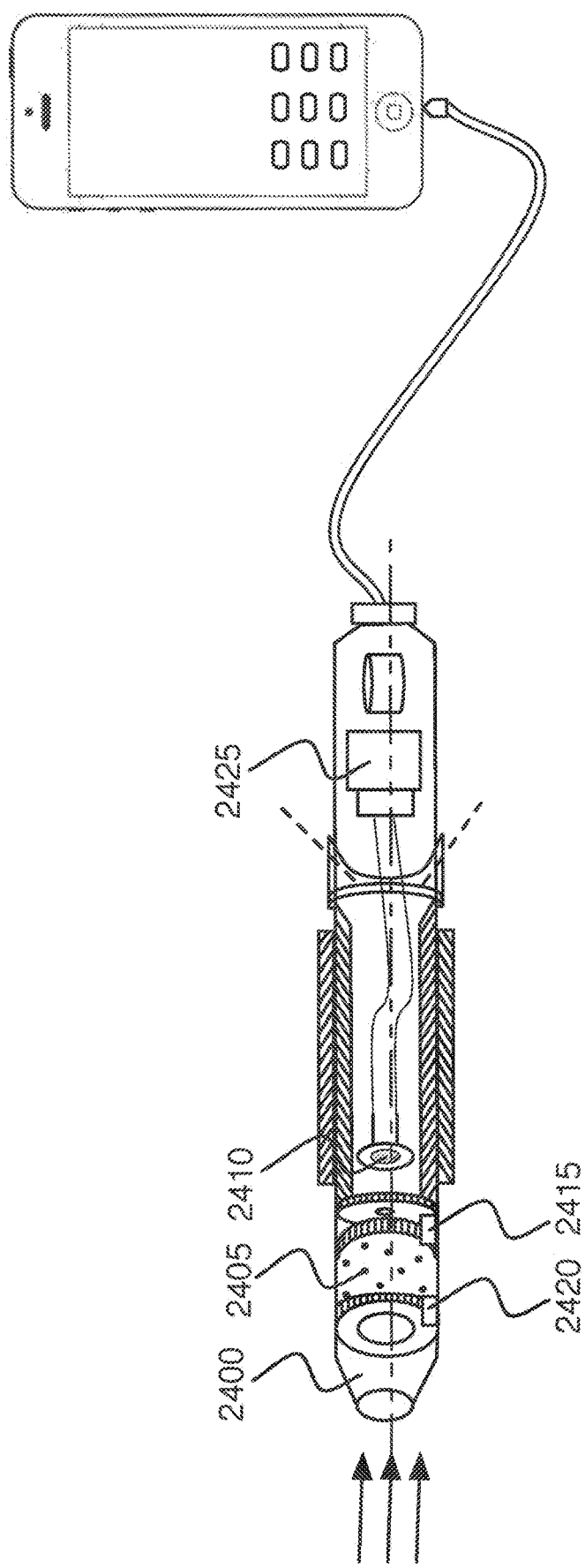
FIG. 24 illustrates a breath acetone measurement device that uses nanoparticle-based sensors.

FIG. 24 illustrates a breath acetone measurement device that uses nanoparticle-based sensors. In embodiments disclosed in U.S. Provisional Patent Application No. 62/161,872, filed May 14, 2015, which is hereby incorporated by reference in its entirety as if fully set forth herein, a user may attach a mouthpiece 2400 and/or a conditioning device (e.g., a desiccant-containing ampoule) 2405 to the inlet of a breath acetone measurement device, where the breath acetone measurement device includes a nanoparticle-based sensor 2410. Inserting the mouthpiece correctly may activate a switch 2420, which may be monitored by processing unit 2425 and cause the processing unit 2425 to sense that the switch 2420 has been activated and that the mouthpiece is correctly inserted. Likewise, removal or a partial removal of the mouthpiece may deactivate the switch 2420, which may cause the processing unit 2425 to sense that the switch 2420 has been deactivated and that the mouthpiece is not correctly inserted.

Similarly, inserting the conditioning device correctly may activate a switch 2415, which may be monitored by the processing unit 2425. Activation of the switch 2415 may cause the processing unit 2425 to sense that the switch 2415 has been activated and that the conditioning device is correctly inserted. Likewise, removal or partial removal of the conditioning device may deactivate the switch 2415, which may cause the processing unit 2425 to sense that the switch 2415 has been deactivated and that the conditioning device is not correctly inserted.

Figure 25:
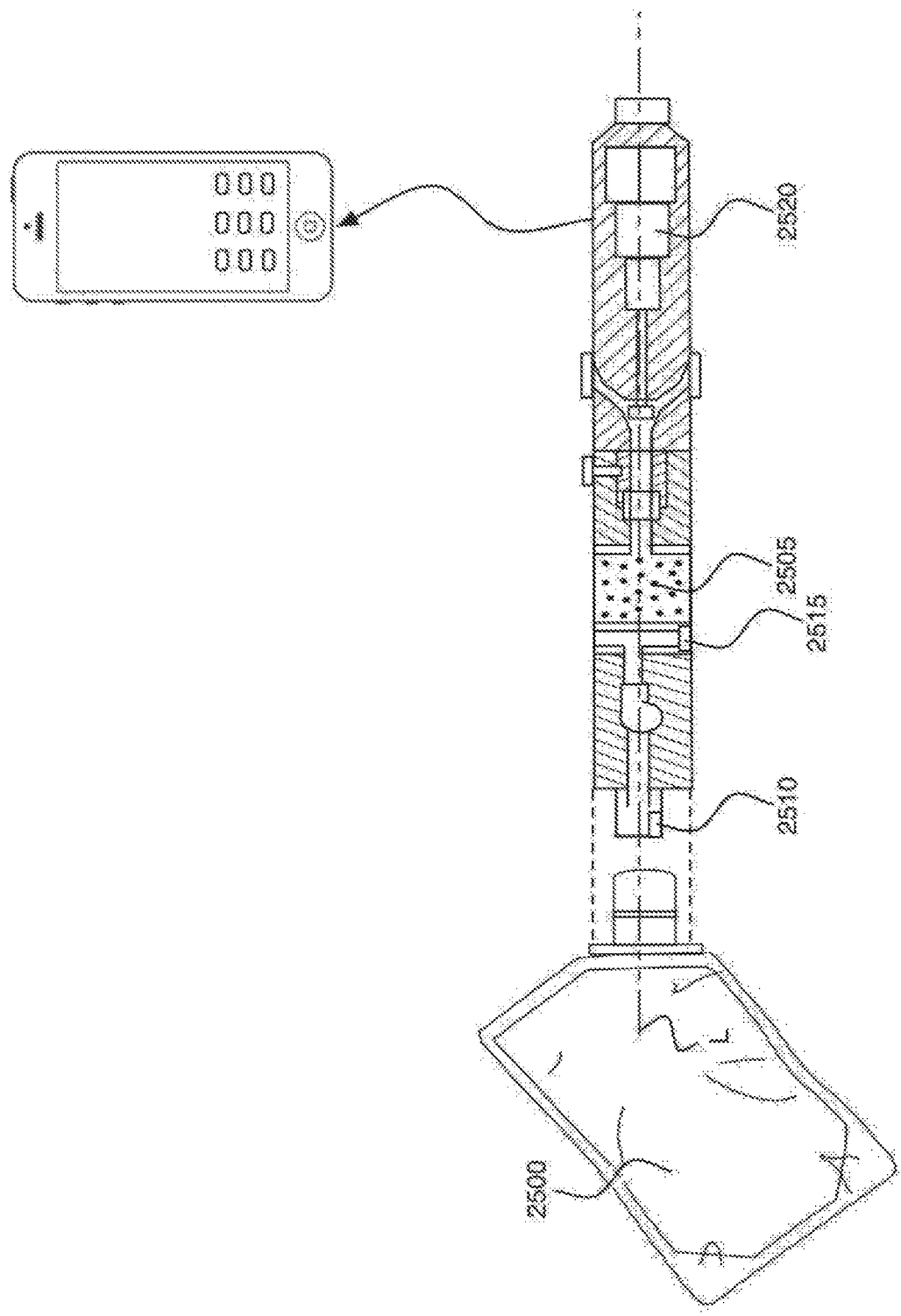
FIG. 25 illustrates a breath acetone measurement device that uses nanoparticle-based sensors and a breath bag instead of a mouthpiece.

FIG. 25 illustrates a breath acetone measurement device that uses nanoparticle-based sensors and a breath bag 2500 instead of a mouthpiece. The breath bag may ensure that a controlled volume of breath is exposed into the nanoparticle-based sensor. When the breath bag is inserted, the tips of the bag may press down on a bump switch 2510. Processing unit 2520 may monitor the state of the bump switch 2510. Pressing down on the bump switch 2510 may cause the processing unit 2520 to sense that the bump switch 2510 is activated and that the breath bag is inserted. Likewise, if the breath bag is removed or partially removed such that the tip of the bag no longer presses down on the bump switch 2510, the processing unit 2520 may sense that the bump switch 2510 is no longer activated and that the breath bag is not inserted properly.

Unlike the embodiment shown in FIG. 24, conditioning device 2505 (e.g., a desiccant) may be located further downstream from the inlet and may also be recognized by a switch 2515. The processing unit 2520 may monitor the state of the switch 2515. Activation of the switch 2515 by the conditioning device 2505 may cause the processing unit 2520 to sense that the switch 2515 has been activated and that the conditioning device 2505 is properly inserted. Likewise, removal or partial removal of the conditioning device may deactivate the switch 2515, which may cause the processing unit 2520 to sense that the switch 2515 has been deactivated and that the conditioning device 2505 is not properly inserted.

Figure 26:
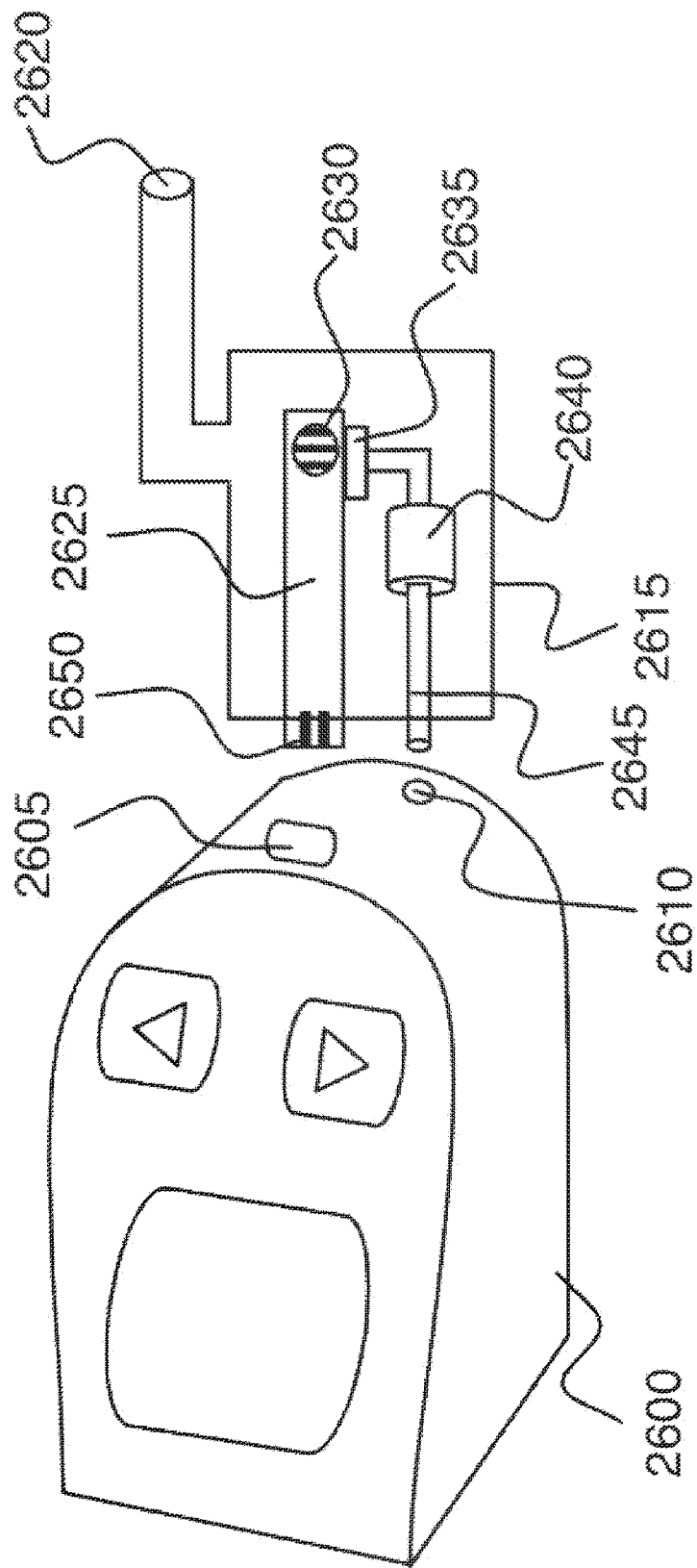
FIG. 26 is an embodiment of an integrated mouthpiece for use in conjunction with an electrochemical breath acetone measurement device.

Other breath acetone measurement devices may use electrochemical sensors that are coupled to enzyme systems. FIG. 26 is an embodiment of an integrated mouthpiece 2615 for use in conjunction with an electrochemical breath acetone measurement device 2600. The breath acetone measurement device 2600 may include an electrode insertion area 2605 and a hydration system insertion area 2610.

In an embodiment, the integrated mouthpiece 2615 includes a mouthpiece 2620 into which a user exhales. In alternative embodiments, the mouthpiece 2620 is connected to a detachable and/or disposable breath bag (not shown), such as those described in conjunction with other embodiments described herein.

The integrated mouthpiece 2615 may further include a test strip 2625 on which an enzyme 2630 is disposed. The test strip 2625 may further include an electrode 2650. A wicking material 2635 may be disposed below the test strip 2625. When a plunger 2645 is inserted into the breath acetone measurement device 2600 via the hydration system insertion area 2610, hydration liquid housed within a liquid container 2640 may be released through the wicking material 2635. The hydration liquid may then be exposed to the enzyme. The interaction of the enzyme, the hydration liquid, and the analyte in the breath may result in an electrochemically active reaction.

For this type of sensor, the proper insertion of the test strip 2525 and the plunger 2645 may be critical. Both may be coupled to a presence sensor monitored by a processing unit (not shown) of the breath acetone measurement device 2600. Thus, the proper insertion of the test strip 2625 may cause the processing unit to sense that the test strip 2625 is properly inserted. Likewise, an improper insertion or the removal or partial removal of the test strip 2625 may cause the processing unit to sense that the test strip 2625 is not properly inserted.

Similarly, the proper insertion of the plunger 2645 may cause the processing unit to sense that the plunger 2645 is properly inserted. Likewise, an improper insertion or the removal or partial removal of the plunger 2645 may cause the processing unit to sense that the plunger 2645 is not properly inserted.

Detachable Component Detection State Diagram and User Interface

As described herein, an electronic device or mobile communications device (e.g., a smartphone), such as the communication or electronic device 30 in FIG. 1, the electronic device 130 in FIG. 2, or the electronic device 230 in FIG. 3, may execute a mobile application that includes executable program code that directs the smartphone to communicate with a breath acetone measurement device and/or a server, such as the remote system 40, 140, or 240. For example, a user can use the mobile application to verify that a detachable component has been properly mated with the breath acetone measurement device, to start a test, and/or to view readings (e.g., test results). As used herein, the mobile application may be referred to as a software application or software "App." Similarly, the remote systems 40, 140, or 240 may execute a network-accessible software application that includes some or all of the functionality of the software application described herein. The features of the network-accessible software application (e.g., allowing the user to start a test, allowing a user to view readings, etc.) may be accessible by a user via the electronic device 30, 130, or 230. For example, the electronic device 30, 130, or 230 may execute a browser that the user can use to access and view a page (e.g., a content page) generated by the network-accessible software application, where the page provides the user with access to such features.

Figure 27:
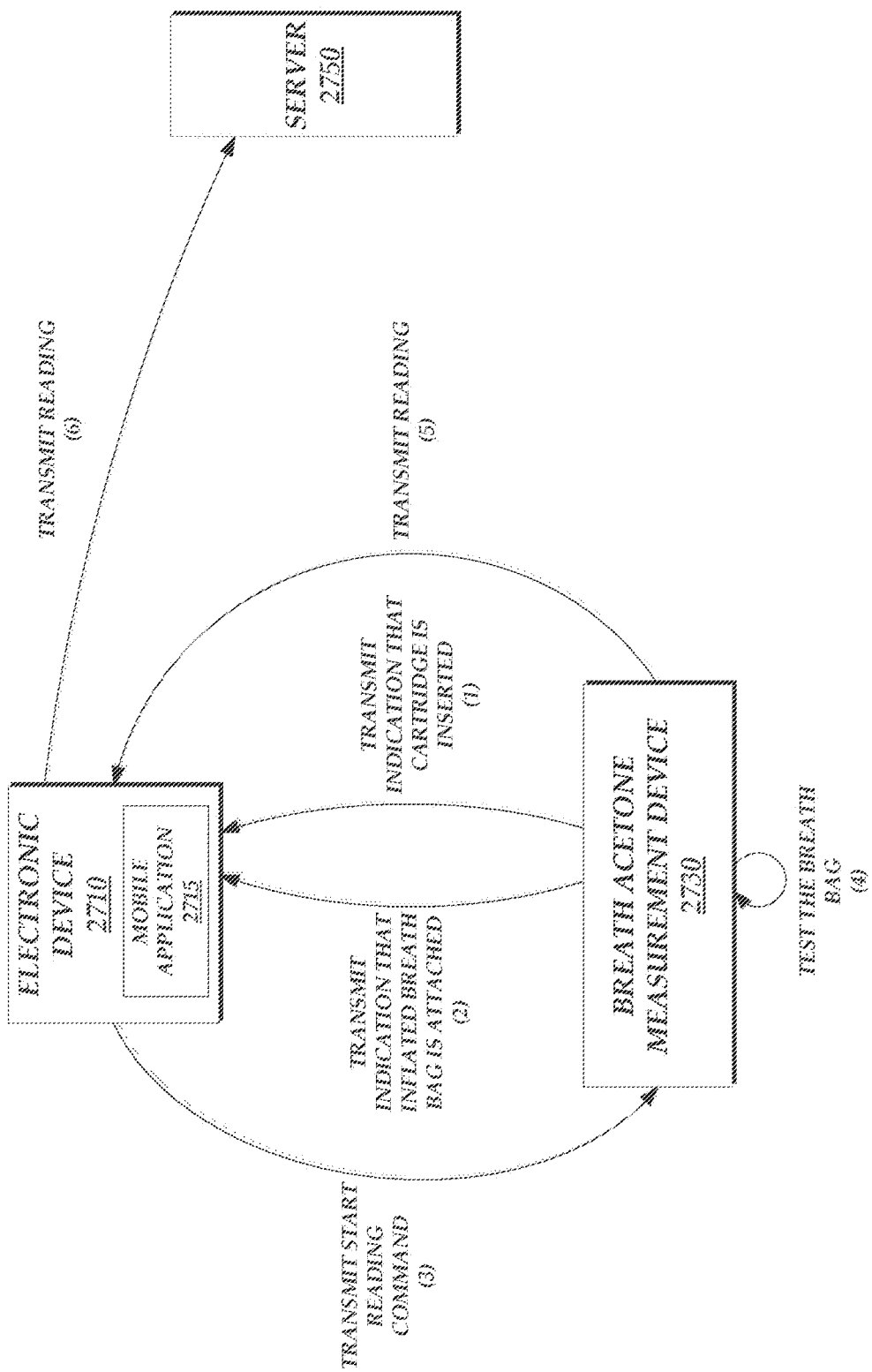
FIG. 27 illustrates a detachable component detection state diagram, according to one embodiment.

FIG. 27 illustrates a detachable component detection state diagram, according to one embodiment. As illustrated in FIG. 27, the state diagram includes an electronic device 2710, a breath acetone measurement device 2730, and a server 2750. The electronic device 2710 may be similar or identical to the electronic device 130, the breath acetone measurement device 2730 may be similar or identical to the breath acetone measurement device 212, and the server 2750 may be similar or identical to the remote system 40. The electronic device 2710 may further include a mobile application 2715 that includes executable program code that directs the electronic device 2710 to communicate with the breath acetone measurement device 2730 and/or the server 2750. In such embodiments, the electronic device 2710 may be a smartphone of the end user.

In an embodiment, the breath acetone measurement device 2730 is configured to accept a breath bag and a cartridge. However, this is not meant to be limiting. In other embodiments involving other types of measurement devices (such as a ketone measurement device that analyzes ketones in a blood or urine sample, a ketone measurement device that detects ketones that have permeated through the skin, etc.), the user interface may instead indicate whether another type of detachable component, such as a test strip, is properly coupled and/or may only provide a notification if the detachable component is improperly coupled. Examples of disposable or detachable components and how these components interact with blood or urine measurement devices can be found in U.S. patent application Ser. No. 14/690,756, filed Apr. 20, 2015, which is hereby incorporated by reference in its entirety as if fully set forth herein.

As described above, the breath acetone measurement device 2730 may include a processing unit that monitors states of presence sensors, such as bump switches. Such monitored states may indicate when a detachable component is properly coupled or inserted and when a detachable component is not properly coupled or inserted or not present. If the processing unit senses (e.g., by monitoring the state of a presence sensor) that the cartridge is properly inserted (e.g., that the mechanical placement of the cartridge or a portion of the cartridge in the breath acetone measurement device 2730 is such that the cartridge or a portion of the cartridge fits completely or nearly completely in an opening provided by the breath acetone measurement device 2730 for the cartridge, such as the cartridge insertion area 2305), then the breath acetone measurement device 2730 may transmit a message to the electronic device 2710 indicating that the cartridge is inserted or coupled (1). Likewise, if the processing unit senses that the breath bag is properly inserted (e.g., that the mechanical placement of the breath bag or a portion of the breath bag in the breath acetone measurement device 2730 is such that the breath bag or a portion of the breath bag fits completely or nearly completely in an opening provided by the breath acetone measurement device 2730 for the breath bag, such as the breath bag insertion area 2310), then the breath acetone measurement device 2730 may transmit a message to the electronic device 2710 indicating that the inflated breath bag is attached or coupled (2).

In an embodiment, the breath acetone measurement device 2730 communicates with the electronic device 2710 via a wireless or wired protocol, such as the IEEE 802.15.1 protocol (e.g., Bluetooth), the IEEE 802.11.x protocol, Ethernet, and/or the like. The breath acetone measurement device 2730 may periodically send transmissions to the electronic device 2710 to confirm that the cartridge is still inserted and that the breath bag is still attached. Such periodic transmissions may occur multiple times per second, such that the mobile application monitors the states of the presence sensors substantially in real time. As described above, the processing unit may also sense if a detachable component that was once properly inserted is no longer properly inserted. If the processing unit senses that a detachable component is no longer properly inserted, a parameter corresponding to the detachable component in the periodic messages may be updated to indicate that the detachable component is no longer properly inserted. The breath acetone measurement device 2730 may continue transmitting the updated periodic message until the state of insertion of a detachable component again changes. In other embodiments, the breath acetone measurement device 2730 may only notify the electronic device 2710 of detected changes in the state of the presence sensors.

Once the electronic device 2710 receives messages (1) and (2) in FIG. 27 (indicating that a cartridge and a breath bag, respectively, are properly coupled), the mobile application 2715 may allow a user to request a new reading by starting a new test. However, the mobile application 2715 may not allow the user to request the new reading if, for example, transmission (2) is received before transmission (1) (e.g., the detachable components are inserted out of a requested order) or if a later message is received indicating that a detachable component is no longer properly inserted. The user may be prevented from requesting a new reading if the detachable components are inserted or coupled in an incorrect order or if a detachable component is not properly inserted; this feature reduces the likelihood that a test will be conducted using a breath sample that is contaminated or lost.

Example user interface screens showing the user experience during this process are shown in FIGS. 28A-28C and 29A-29B and described below. If the user requests a new reading, the electronic device 2710 may transmit a Start Reading command (3) to the breath acetone measurement device 2730.

As further shown in FIG. 27, the breath acetone measurement device 2730 may test the contents of the breath bag (4) in response to receiving the Start Reading command. The test may result in a reading that is then transmitted (5) to the electronic device 2710. Automatically, without any user interaction, the electronic device 2710 may transmit the reading (6) to the server 2750 for storage; this desirably prevents the user from being able to selectively block some readings from being reported to the server 2750.

Figure 28A:
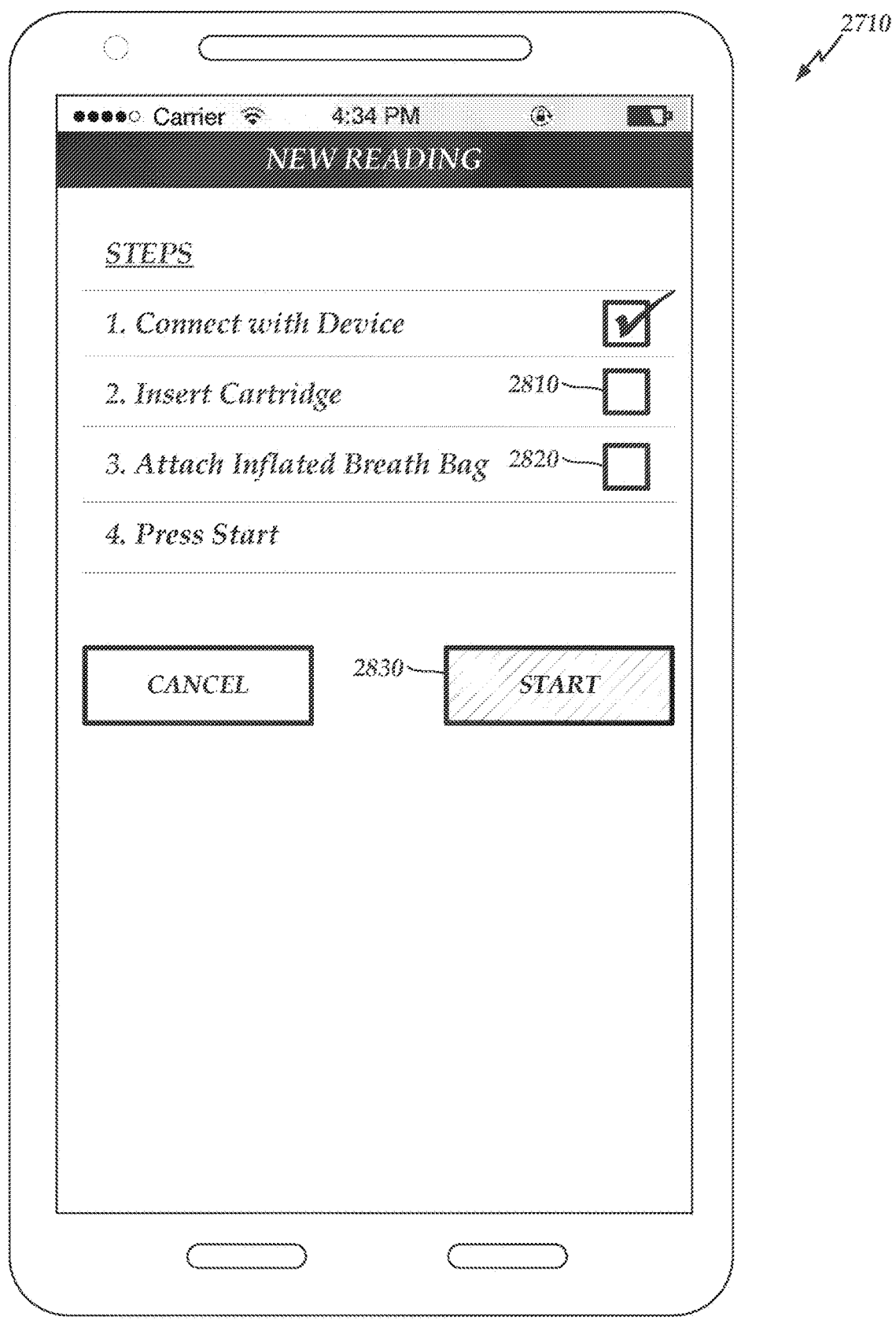
FIGS. 28A-28C illustrate a user interface displayed by the electronic device that depicts a status of the insertion of detachable components.
Figure 28B:
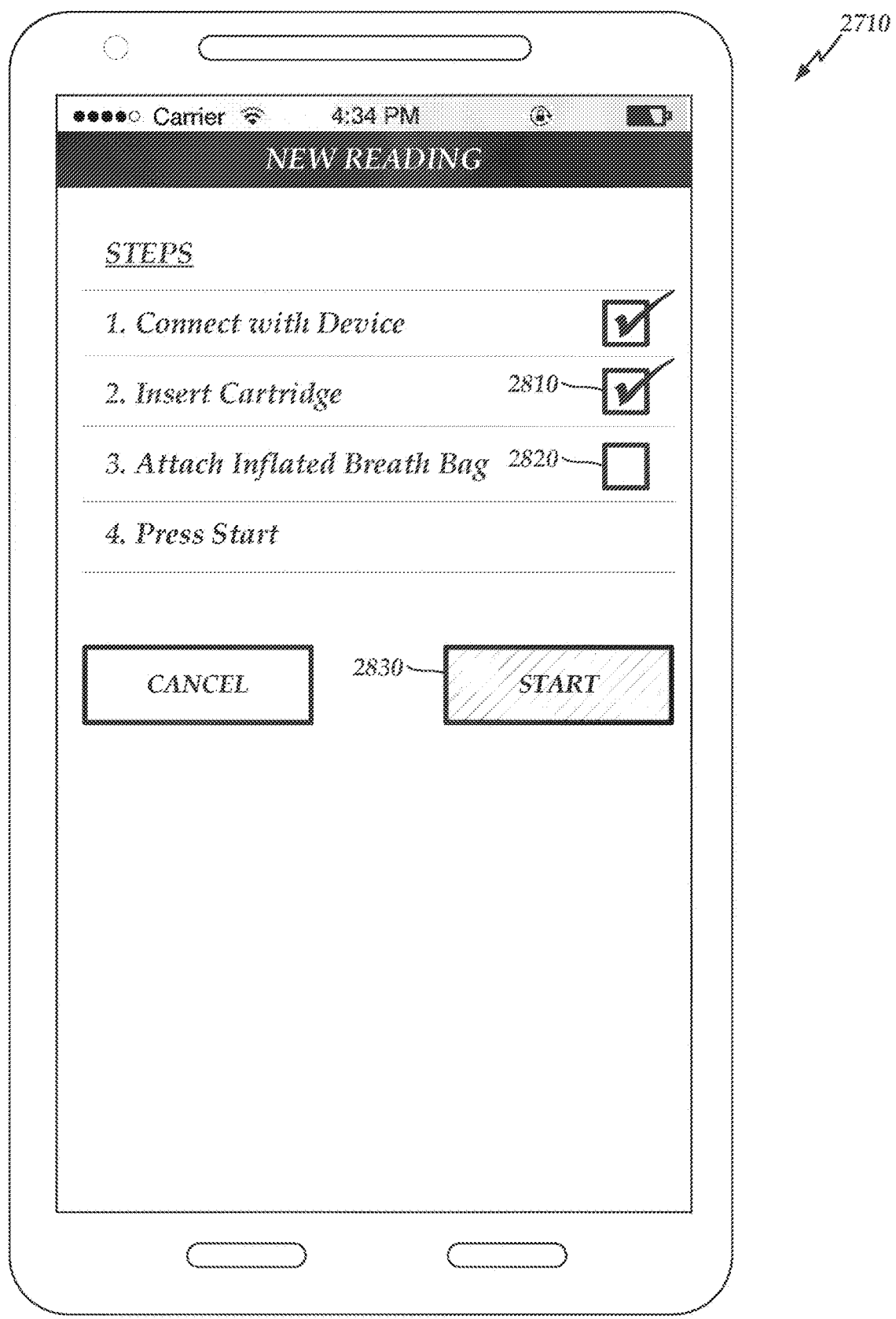
Figure 28C:
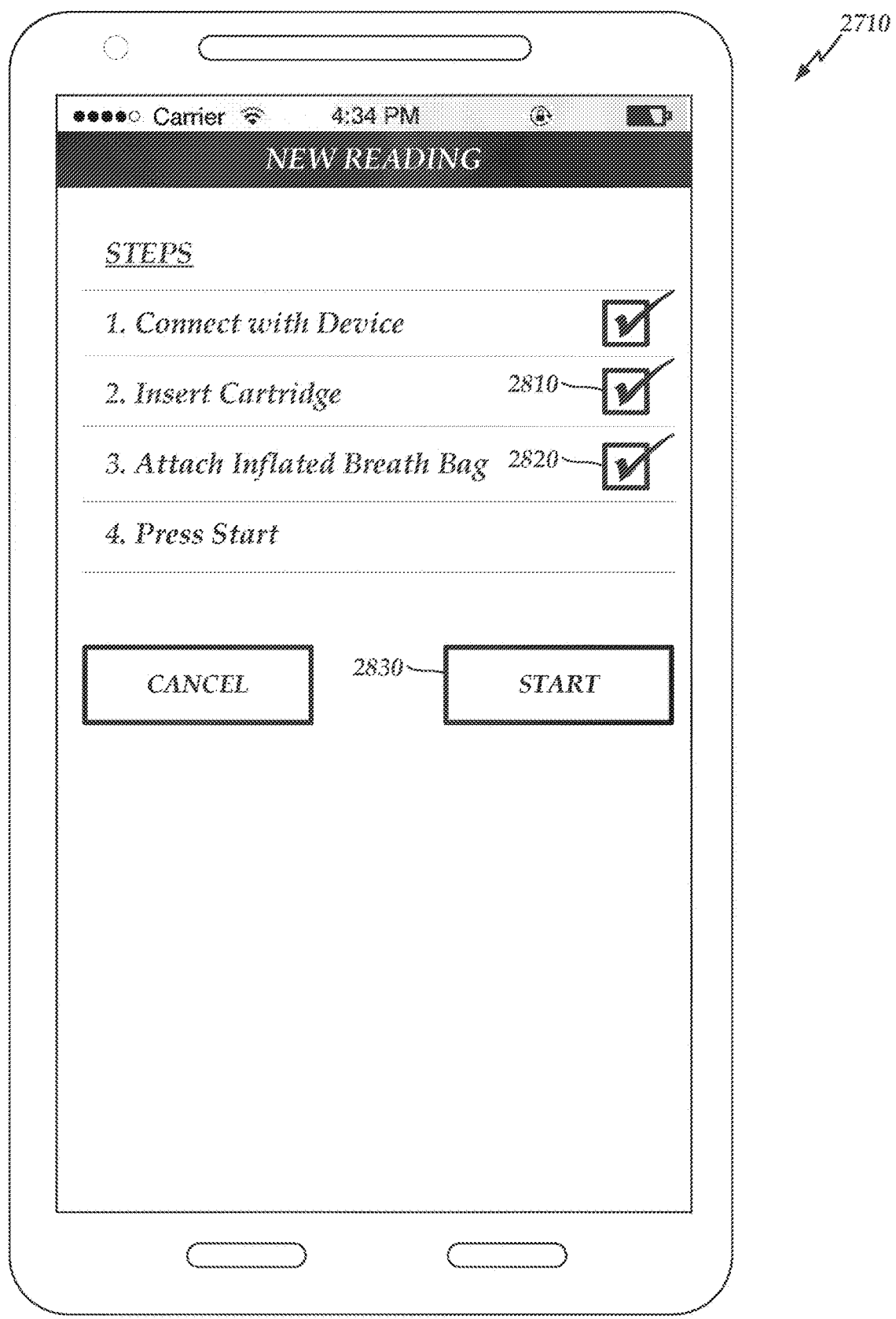

FIGS. 28A-28C illustrate a user interface displayed by the electronic device 2710 (e.g., a user interface of the mobile application 2715) that depicts a status of the insertion of detachable components. As illustrated in FIG. 28A, the user interface presents a user with a list of steps to complete to generate a new reading. In this example, the user interface indicates steps that are being automatically performed (or that have already been performed during prior tests, such as pairing in some embodiments), steps for the user to perform, and/or which of these steps have been completed. The steps include the following: (1) connect with the breath acetone measurement device 2730 (e.g., via a pairing procedure as described below), (2) insert a cartridge into the breath acetone measurement device 2730, and (3) attach the inflated breath bag to the breath acetone measurement device 2730. Once these steps have been completed in order, the "start" button 7630 is enabled or displayed, enabling the user to instruct the breath acetone measurement device 2730 to start a new reading. For simplicity and illustrative purposes, the user interface indicates that the electronic device 2710 is already successfully connected with the breath acetone measurement device 2730.

Boxes 2810 and 2820 indicate a status of the insertion or attachment of the cartridge and the inflated breath bag, respectively. For example, as illustrated in FIG. 28A, neither the cartridge nor the inflated breath bag are inserted into the breath acetone measurement device 2730. Thus, the start button 2830 is shaded out, which indicates that the start button 2830 is disabled and that the user cannot initiate a new reading.

As illustrated in FIG. 28B, the box 2810 may include a checkmark or other symbol to indicate that the cartridge is inserted. However, the status of the box 2820 is unchanged, indicating that the inflated breath bag is still not attached. Because the inflated breath bag is still not attached, the start button 2830 is still shaded out.

As illustrated in FIG. 28C, both boxes 2810 and 2820 may include a checkmark or other symbol to indicate that the cartridge is inserted and that the inflated breath bag is attached. Thus, the start button 2830 is no longer shaded out, which indicates that the start button 2830 is enabled and that the user can initiate a new reading by selecting the start button 2830. However, the start button 2830 may once again become disabled if, for example, the cartridge or the inflated breath bag is removed or partially removed such that the presence sensor no longer detects the detachable component as being inserted.

In other embodiments, not shown, the user interface displayed by the electronic device 2710 may not display an indication of whether the breath bag and/or the cartridge are inserted or coupled properly to the breath acetone measurement device 2730. Rather, the user interface may only display a notification if the breath bag and/or the cartridge are inserted or coupled improperly.

Figure 29A:
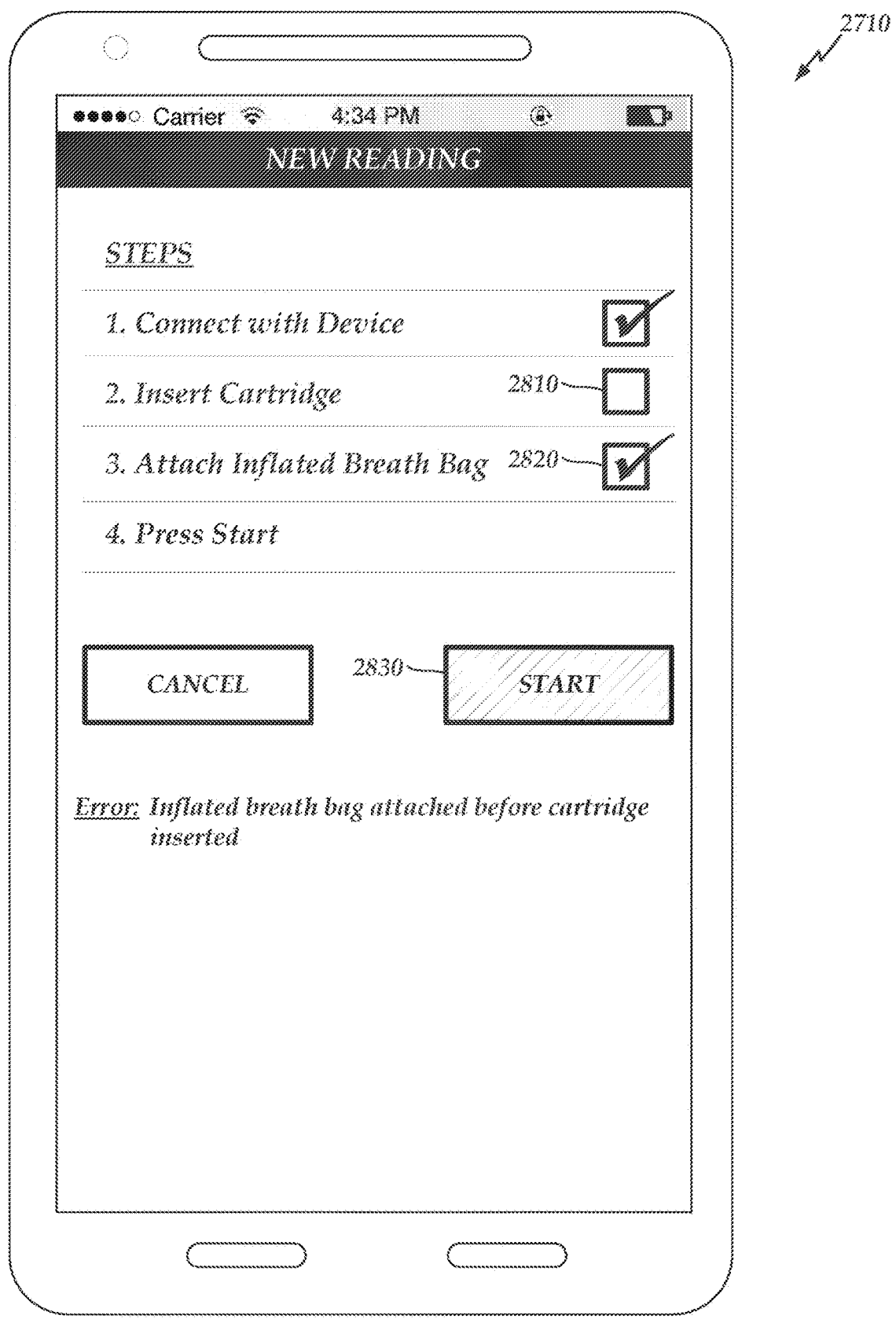
FIGS. 29A-29B illustrate another example in which the detachable components are inserted in a different (and incorrect) order.
Figure 29B:
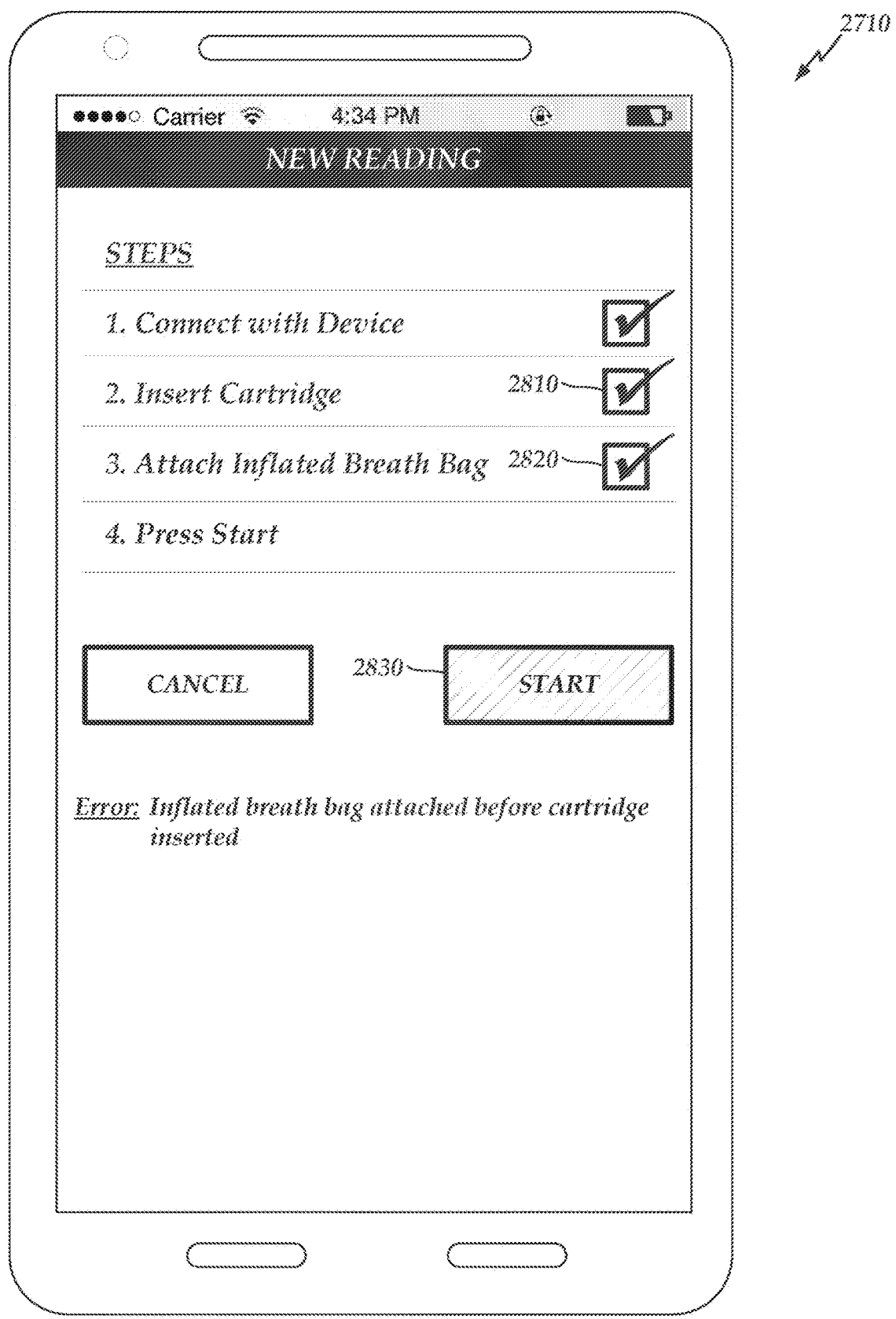

FIGS. 29A-29B illustrate another example in which the detachable components are inserted in a different (and incorrect) order. As illustrated in FIG. 29A, the box 2820 indicates that the inflated breath bag is attached. However, the box 2810 indicates that the cartridge is not inserted. Thus, the start button 2830 is shaded out and disabled.

In some embodiments, an error message is displayed to indicate a reason why the start button 2830 will not be enabled even if the cartridge is inserted. The user interface may also convey to the user steps to correct the error. For example, if a breath bag is attached while no cartridge is present (as in FIG. 29A), an error message may be displayed indicating that, because the breath bag was attached while no cartridge was detected, the breath bag must be removed and a new breath sample obtained. An error message may also be displayed if, for example, the user does not insert a detachable component into the breath acetone measurement device 2730 (or perform some other action) within a threshold period of time. The threshold period of time may start once the electronic device 2710 and the breath acetone measurement device 2730 have completed connecting, once a first detachable component is inserted or partially inserted into the breath acetone measurement device 2730, once a user indicates that he or she would like to begin performing the steps for generating a new reading (e.g., explicitly via an input or indirectly by accessing a certain user interface, window, or page in the mobile application 2715, such as the user interface illustrated in FIG. 27), and/or the like. As one example, once a cartridge and breath bag have been coupled in the proper order, the mobile application 2715 may enable the start button 2830, but thereafter disable the start button 2830 if the test is not started within a threshold amount of time (e.g., 3 minutes). The mobile application 2715 may also disable the start button 2830 if the wireless connection is lost before the test is started. The logic for determining whether the breath bag and cartridge were inserted in the proper order (and/or for determining whether any timing constraints were satisfied) is preferably embodied in the mobile application 2715, but may alternatively be embodied partly or wholly in the program code that runs on the breath acetone measurement device 2730.

As illustrated in FIG. 29B, the box 2810 indicates that the cartridge is inserted. However, the start button 2830 is still shaded out and disabled despite the fact that both the cartridge and the inflated breath bag are inserted. The start button 2830 may still be shaded out (disabled) because the insertions occurred in an order other than the order specified by the steps listed in the user interface.

The user interfaces with boxes 2810 and 2820 can be adapted for use with other types of devices (e.g., devices that measure ketones in blood, urine, or other body fluids other than breath, devices that measure ketones that have permeated through the skin, glucose sensors, blood analysis sensors, etc.) in which the user needs to complete a sequence of steps. For example, presence sensors or other types of sensors can be monitored by a processing unit of an analysis system to determine whether specified steps are followed. Such information can be transmitted to the electronic device for display to the user (e.g., via the mobile application 2715). In the case of a portable blood ketone measurement device, presence sensor(s) may determine when a test strip that includes an absorbed blood droplet is inserted by the user and the user interface may indicate whether the test strip is inserted and/or may only provide a notification if the test strip is improperly inserted. Additionally, a sensor may be attached to the lancet so that the time of the blood prick is matched against the time of the strip insertion, such as described in U.S. patent application Ser. No. 14/690,756, filed Apr. 20, 2015, which is hereby incorporated by reference in its entirety as if fully set forth herein. In the case of a portable urine ketone measurement device, presence sensor(s) may determine when a test strip that includes an absorbed urine sample is inserted by the user and the user interface may indicate whether the test strip is inserted and/or may only provide a notification if the test strip is improperly inserted. In the case of a glucose sensor, presence sensor(s) may determine whether an electrode is inserted by the user and the user interface may indicate whether the electrode is inserted and/or may only provide a notification if the electrode is improperly inserted.

Additional Features of the Software Application and Related Methods

In each of the presently preferred system embodiments described herein above, and in accordance with preferred method implementations according to aspects of the present disclosure, the acetone measurement process and other process as described herein are carried out using software, including in the form of the mobile application (e.g., the software application or software "App"). The terms "App" and "software application" are used interchangeably herein. In system 10, the software App may be executed by ketone measurement unit 11, and more specifically by electronic or communications device 30. The software App may alternatively or in addition be executed by the remote system 40 and the remote system 40 may generate a page (e.g., a content page) to provide access to the functions of the software App. In system 110, the software App may be executed by the electronic device 130 and/or the remote system 140, and in system 210, the software App may be executed by the electronic device 230 and/or the remote system 240. In general, any of the software-implemented functions described herein (e.g., functions described herein as being performed by the App) could be implemented on any of the disclosed devices or systems (e.g., the electronic devices, the measurement devices, the remote systems, etc.). To illustrate these aspects of the disclosure, a method is described. The software App may include executable program code that directs the electronic device 230 to implement the method.

Figure 7:
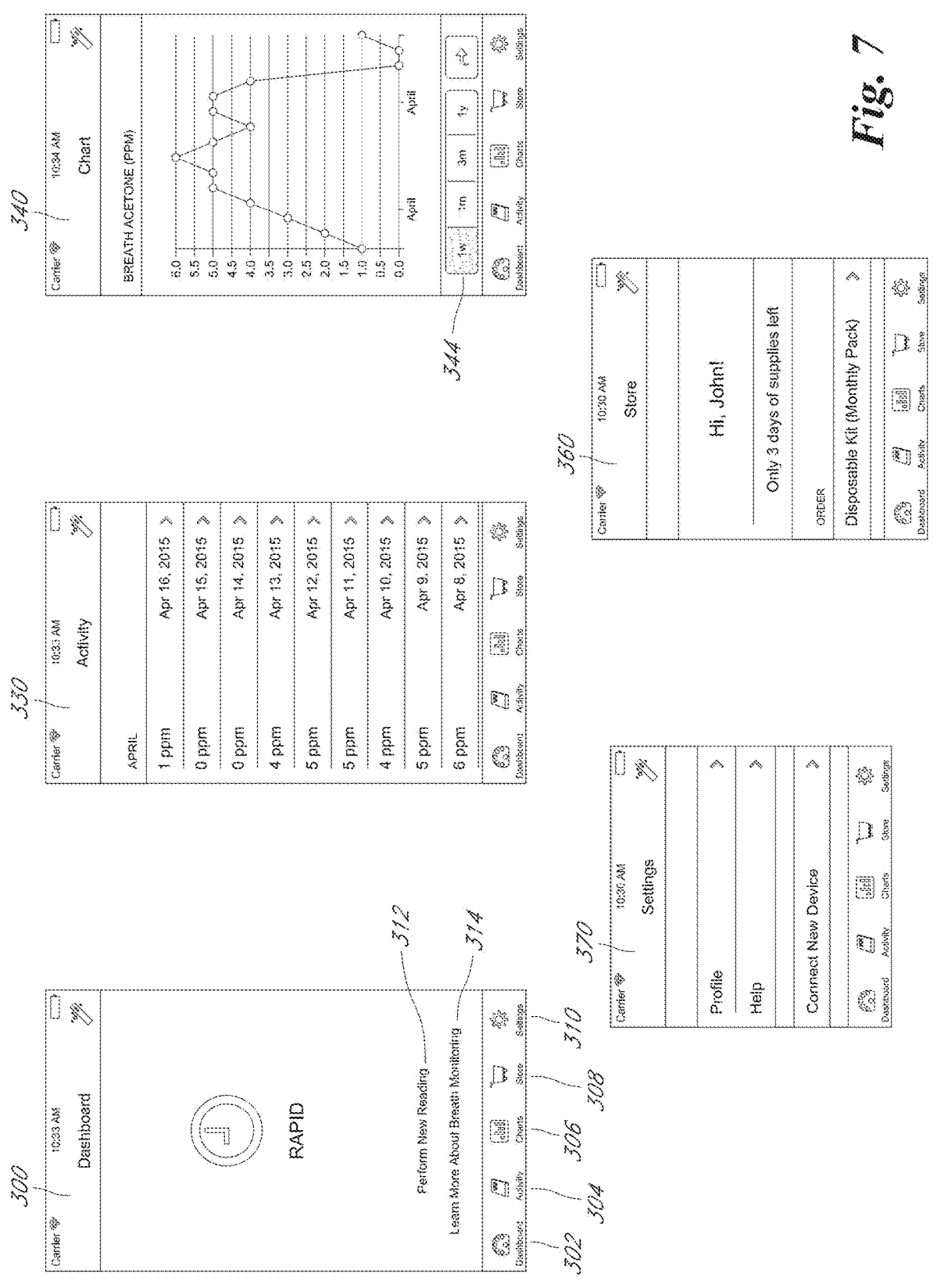

The user calls or launches the App on electronic device 230, whereupon the App's opening panel 300 is presented on touchpad display 234 as shown in FIG. 7. This opening panel 300 presents the user with the date and time and a number of options. As shown at the bottom of panel 300, these options include a Dashboard button 302, an Activity button 304, a Charts button 306, a Store button 308 and a Settings button 310. The center of the opening panel 300 prominently features two larger button options. One is a "Perform Measurement" button 312, and the other is a button 314 entitled "Learn About Breath Monitoring."

It may be noted that, in each of the subsequent panels as described herein below, buttons 302, 304, 306, 308 and 310 may continue to be displayed at the bottom of display 234.

Selection of the Dashboard button 302 may cause the App to display the Dashboard panel. Dashboard panel allows the user to begin a breath acetone test or, equivalently, measurement.

Upon selection of Activity button 304, the App displays an Activity panel 330 as shown in FIG. 7. The Activity panel or tab 330 allows the user to view his or her historical breath analysis results. This tab further allows the user to "categorize" or "tag" data or annotate results. In the main frame of Activity panel 330 as shown in FIG. 7, the results of the most recent breath acetone measurements are shown, using a format of one measurement result per horizontal line. The measurement entries are positioned under category headings of "Recent Readings," "Yesterday," and "Monday." Each entry includes the date and time at which the measurement result was obtained. The breath acetone measurement results in this illustrative example are provided in parts per million (ppm) of acetone in the breath sample. Tagging may also occur automatically by the App, such as in the event that the user identifies computer-determinable rules (e.g., "AM test is between 7 am and 9 am" versus "PM test is between 7 pm and 9 pm"). These rules may be inputted through the App or through a companion content page accessible over a network (e.g., a web site).

Upon selection of the Charts button 306, a Charts panel 340 is presented on display 236. Charts panel or tab 340 allows the user to view his or her historical results in one of several graphical formats. Charts panel 340 offers the user a variety of charting formats for presenting breath acetone measurement results over time. The default chart in this illustrative embodiment presents measurement results over the most recent week, in a connected point format. The horizontal or x-axis represents the day of the measurement result and the vertical or y-axis represents the breath acetone concentration for the respective days in units of ppm. The y-axis alternatively or in addition may comprise units of a Fat Burn Number ("FBN") value or some other user-friendly scale. A series of buttons 344 at the bottom of Chart panel 340 gives the user the option of presenting breath acetone measurement results over different periods of time. In this illustrative example, the options are for one week (1 w), one month (1 m), three months (3 m), and one year (1 y).

In certain instances, it is useful for a dieter to have a user-friendly scale, as described above. Instead of reporting in units such as parts-per-million (ppm), a Fat Burn Number (FBN) value or other similar term may be used. A FBN value may be and preferably is the same as the ppm value, but with a set number of decimal points for reporting (e.g., tenth of a unit) and no "ppm" units. As an example, a level of 2 ppm would be a FBN value=2. Other relationships may be used and preferably are explained in either a user manual or a professional manual associated with the measurement device.

Figure 8:
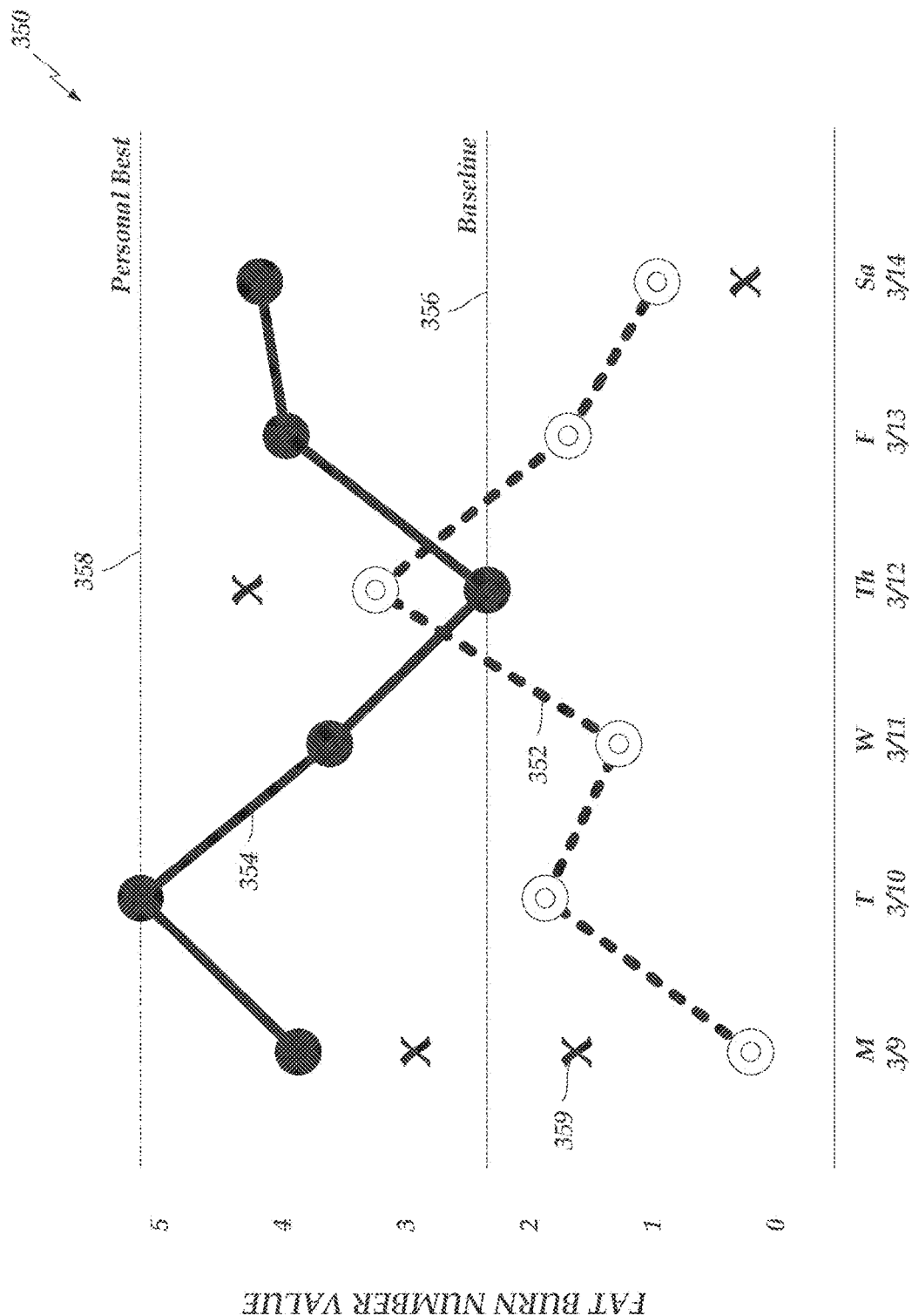
FIG. 8 shows a scatter plot display output of breath acetone measurement data provided by the software application, display panels for which are shown in FIG. 7.

As an illustrative alternative to the histogram-type chart 342 shown in Charts panel 340 in FIG. 7, a time-based point plot or scatter plot 350 can be displayed by the App as shown in FIG. 8. In the point plot or scatter plot 350, the horizontal or x-axis represents time, which in this example is demarcated in days with a corresponding date (e.g., here Monday, March 9 through Sunday, March 14). The vertical or y-axis represents a Fat Burn Number value as described above. This point plot or scatter plot 350 will be discussed in further detail herein below, but it may be noted here that the point plot or scatter plot 350 comprises two sets of measurement results with two measurement results per day being displayed: (a) one for a morning or AM measurement result; and (b) another for an afternoon or PM measurement result. Each measurement result is represented by a point or dot on the chart.

Under the Charts tab 340 of FIG. 7, the user may view his or her results according to "tag" or "category," as will be explained more fully herein below. Tab 340 also allows the user to select one of several algorithms that present the data. Examples of algorithms in this preferred implementation include: (a) baseline subtracted from current result, (b) three day running average of results, and (c) three day running average subtracted from current result. Other algorithms also may be used.

Selection of the Store button 308 causes the App to display a Store panel 360. The Store allows the user to purchase products related to the breath measurement or analysis device, such as the detachable, replaceable, and/or disposable cartridges and detachable, replaceable, and/or disposable breath bags. It is not uncommon for the ketone measurement device or devices to use a replaceable or consumable component in the course of its operation. In system 210 as described herein above, for example, base 212a uses a detachable cartridge 218c that functions as part of the sensing subsystem 218 to measure the concentration of the acetone in the breath sample. Although not necessarily limiting, presently preferred embodiments of this cartridge 218c may be used for a single breath acetone measurement, and may be replaced with a fresh cartridge after each measurement. Similarly, as with many generally- or commercially-available apps on commercially-available smartphones, the user may shop an app store and buy or otherwise acquire apps, plugins, software features and the like to supplement those already on electronic device 230 and included in the App. Store panel 360 includes functionality to track the user's stores (e.g., his or her inventory of cartridge, charts, features and/or the like), and enables the user to make additional acquisitions as needed or desired. Store panel 360, for example, optionally includes an automatic ordering feature in which, when the number of breath acetone measurement results stored in the App are at a pre-determined threshold level, the App automatically goes online to the Store and orders a replenishment stock.

The Store in this App displays the number of days left until supplies are needed. This would be based, for example, on the user's last purchase and the user's inputted frequency of desired measurement (from the Settings tab).

If the device registers that there was an internal failure, a prompt is generated that notifies the user that he or she will receive a discount related to the number of failures during his or her next purchase. This information is transmitted to the Store and used to compute the price of the next set of disposable purchases.

Selection of the Settings button 310 causes the App to display a Settings panel 370 as shown in FIG. 7. The Settings panel or tab 370 allows the user to recognize new devices (e.g., via Bluetooth or other means) and store individualized information (e.g., user height, age, weight, gender, frequency of desired measurement, and other user-specific characteristics). Under the Settings tab, a user profile may be created. An example of the type of information that would be useful in a user profile for weight management is shown in FIG. 9. Such information may include electronic mail address, name, date of birth, current weight, AM window start, PM window start, gender, exercise frequency, baseline breath acetone, goal weight, lifestyle, and/or exercise intensity. This information is included in the Settings tab of the App or in a companion content page accessible over a network that is linked to the App.

Variations in the Measurement Results

As was explained herein above, ketone concentrations are generally correlated with fat metabolism. In practice, however, the complex multi-step and multi-pathway processes between fat metabolism, ketone generation, and ketone clearance results in many variables that can impact this relationship. Some of those variables are physiological with respect to the user. Others relate to the acetone measurement itself, including, for example, the device used to make the measurement, the measurement protocols and procedures, the environmental conditions at the time and place of measurement, and so on. Each of these variables or factors can impact the measurement results and obscure accuracy or reliability.

In some instances, it may be best to merely discard measurement results that have been adversely impacted by such variables as aberrant. In others, where amenable, it may be possible to compensate or adjust the measurement results to account for the variable or variables. In many cases, however, one preferably anticipates the variable or variables and avoids them or their impact all together, or attempts to isolate the impact of such variable or variables and separately identifies and reports the variable or variables.

An example of a variable that can adversely impact measurement results and a method for accommodating it according to an aspect of the present disclosure is found in the time of day at which the breath acetone measurement is made. On average, breath acetone levels when measured first thing in the morning, prior to eating or drinking beverages other than water, are lower than acetone levels measured in the afternoon or evening. Thus, if one merely directly compares breath acetone levels measured at random times throughout the day, a relatively high variability in the measurement results will be observed. By reconfiguring the measurement results data, (e.g., by segregating morning measurement results from afternoon results), that data may become much more comparable and useful, and may limit if not eliminate time-of-day variability that is unrelated to true or major changes in fat metabolism. This is illustrated in FIG. 8, wherein the sequential daily morning or "AM" measurement results are connected by a dashed line 352, and the sequential daily afternoon measurement results are connected by a solid line 354. The crossed out points may be measurements that either the App or the user identified as "aberrant" or not complying with pre-set rules. As an example, consider the following: the user is told to perform breath acetone measurements between 7 am and 9 am. The user, however, fails to perform a measurement within this window and instead performs a measurement at 10 am. This data point is an example of an "aberrant" measurement.

Incidentally, a "baseline" horizontal line 356 and a "personal best" horizontal line 358 can be superposed on the data. These will be discussed further herein below.

Figure 10:
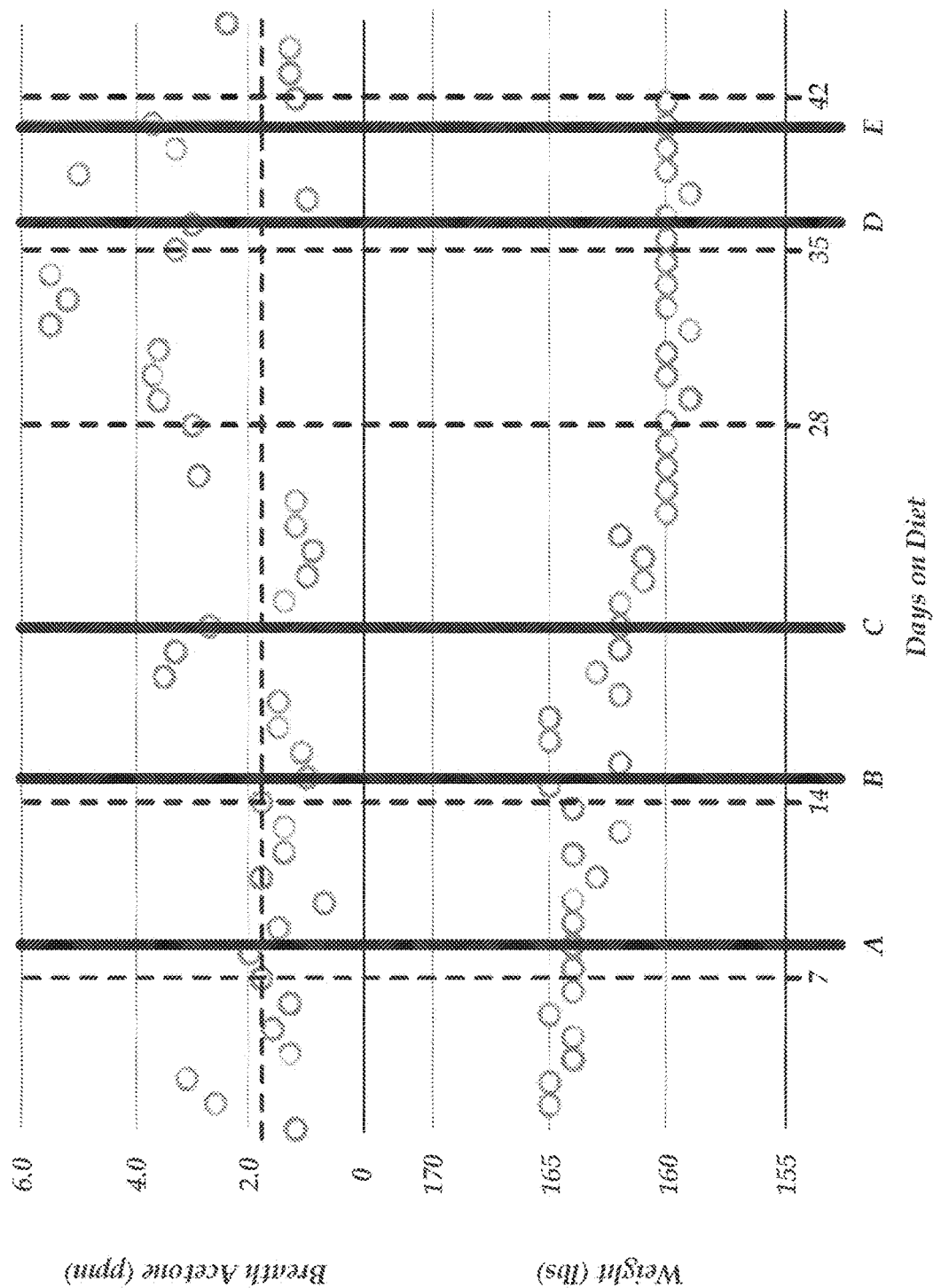
FIG. 10 shows a graphical chart displaying breath acetone levels and various events.

The measurement results data and variability, however, are not always as amenable to identification and modified presentation as the time-of-day example illustrated in FIG. 8. A more complex, and more commonly encountered, type of measurement results data set is shown in FIG. 10. FIG. 10 presents a plot of breath acetone measurement results for a user on a program diet. The horizontal or x-axis represents time, and more specifically the number of days the user has been on the diet. The upper portion of the vertical or y-axis represents the user's breath acetone concentration (in ppm) as measured using a system as depicted in FIGS. 3-5 on the day corresponding to the associated position on the x-axis. The lower portion of the vertical or y-axis represents the user's body weight (in pounds or "lbs.") measured at the time of acetone measurement (e.g., using a standard weight scale). The breath acetone measurements are taken each morning, so each data point in the upper portion of the plot represents a one-day measurement.

For the first eight days, the acetone concentration is relatively spread, but after the first three days shows a reasonably steady trend upward, indicating that fat metabolism is stable and increasing. At about day nine, just before the point demarcated as line A in FIG. 10, the acetone concentration makes a local peak and, for the following two days, sharply declines in a steep downward trend. At day 11, the measured acetone concentration returns to near its prior local peak levels and continues in this range through day 14. On day 15, demarcated in FIG. 10 at line B, the acetone concentration drops modestly relative to the day 10-14 trend, but promptly begins trending upwardly, jumping significantly on day 19 and remaining at this elevated level on day 20. Beginning on day 21, demarcated at line C, the acetone concentration once again drops substantially, and it remains at its relatively low level for the following four days, returning to its previously higher levels on day 27, and proceeding even higher on days 32-34. Beginning on day 35 and continuing for the next two days (generally demarcated at line D), the acetone concentration drops precipitously. It recovers on day 38, drops modestly on days 39-40, and again drops precipitously on days 41-43.

Viewing this raw data without further explanation, it appears quite erratic and inconclusive. Taken in context and with knowledge of the user's activities, however, it provides useful information. The events demarcated as lines A, C, D and E in FIG. 10 are non-compliance events, in which the user deviated from the treatment program. Line B is when the user saw the weight loss coach, which resulted in a temporarily positive increase in breath acetone levels.

Baselines and Normal State

In some preferred embodiments and method implementations according to aspects of the present disclosure, it is desirable to establish an initial reference point, condition, or set of conditions against which actual ketone measurement results can be compared to identify or evaluate changes (e.g., over time). This initial reference point, condition or set of conditions may comprise or reflect a "baseline" (e.g., a normal state), an expected value or set of values, a selected starting point, and/or the like, from which ketone measurements according to various aspects of the present disclosure may be measured or compared. The baseline in general terms may be a standard value or set of values for a factor relevant to analyte measurement (including the measurement of multiple analytes), that is expected to change for a given user from time to time or measurement to measurement, or for a given user relative to a population of users (e.g., from a statistical norm). If a user is about to commence a new weight loss program, for example, the user's ketone levels for a period of time immediately prior to commencing the program may serve as a baseline. As the program is undertaken and progresses, the App can compare ketone measurement results to the baseline to provide a better understanding of the subsequent ketone measurement results and thus to provide information on the effectiveness of the program, the user's compliance with the program, and/or the like. In another example, this one involving evaluation of a drug regimen, if one were to measure the concentration of a particular analyte before and after administration of a drug, for example, the baseline generally would be the analyte concentration before the drug was administered. If one were to measure analyte concentration as part of monitoring a physician-prescribed diet, the baseline generally would be the analyte concentration just before the diet began. As an illustrative example, in FIG. 10, a baseline may be established by taking the average of the breath acetone measurement results for the first seven days. This baseline, which for this data is approximately 1.9 ppm, is shown in FIG. 10 as a horizontal dashed line 356*a*.

A user baseline is preferably determined by the App at a pre-selected physiological state. Examples of such physiological states would include, for example, fasting or not-fasting, dieting or non-dieting, with or without exercise, and others. A user baseline may be computed by the App, for example, using an average breath acetone measurement value obtained over a fixed or set number of measurements. As an example, the App can average breath acetone measurement results over a five consecutive day period. Depending on the particular application (e.g., the user's lifestyle), in some instances it will be preferable to establish the baseline under tightly controlled circumstances. For other individuals and in other applications, the baseline may incorporate factors that may be expected to change for that individual and the planned program. For instance, if the individual does not exercise every day, but does exercise two times a week, the baseline may be taken by the App over two weeks and encompass four workout events.

A baseline in a general sense of the term may represent a logically- or arbitrarily-designated starting point from which to judge or evaluate other measurement results, usually subsequent to the baseline. An example of a particular baseline, and often a relatively useful and potentially important one, involves a "normal state" of the user. Although the "normal state" of the user typically is a relative term or factor that can depend on various factors as well the specific analyte being measured, it is generally understood to reflect a long term desired state of health and wellness. A "normal" weight for a user, for example, might be a weight that is suitable, appropriate or even ideal for a person of the user's height and frame. Although a normal state can serve as a baseline, it need not be a state or condition that the user actually was in at any particular time. It may, for example, merely represent a goal or target. A "normal" state can be defined or selected by the user or user of the ketone measurement device (e.g., via the App) or, for example, the physician prescribing the ketone measurement and overseeing the use of the measurement or analysis device.

A "baseline" can be, but need not be, a "normal state." In the context of a weight management program, for example, the weight at the beginning of the program may be selected as the baseline, and the "normal state" of the user may be the target weight to be achieved during the program. Alternatively, the baseline may be the weight at the beginning of the program, and the target weight for the completion of the program may be well above what might be considered a "normal" weight for that user. A series of programs, in that illustrative case, may be required to achieve the "normal" state.

It is also useful in some contexts and embodiments to include a demarcation for the user's "personal best." As the name implies, this personal best is a measurement result or other measure that reflects the best result or results achieved by that user in the course of the program or time of acetone measurement. With reference to FIG. 8, the user's personal best acetone measurement result, measured as a Fat Burn Number value, was a 5, and was achieved on Tuesday, March 10. To demarcate and highlight this, the App may display a marker, such as horizontal line 358, identified as representing the personal best. This line provides the user with an ongoing indication of how well the program objectives are being met relative to the personal best, or similarly, with respect to what the user is capable of achieving based on his or her own prior results. Preferably, the "personal best" does not account for any measurements that were marked or identified as aberrant.

To illustrate the use of a baseline to improve breath acetone measurement, consider the following presently preferred method implementation. For simplicity and ease of illustration, this preferred method is described as being implemented using system 110 (e.g., the electronic device 130 or the remote system 140) of FIG. 2 and the App described herein, although this is not necessarily limiting.

The method comprises specifying a physiological state at which breath acetone levels of the user should be determined. In this preferred but merely illustrative method, this is accomplished by a person planning the program, who may be the user, a treating physician, nutritionist or other clinician, and/or the like. This planner considers the user, the planned program, the objectives of the program, etc., and selects or otherwise specifies, for example in the App, the physiological state of the user at which the breath acetone measurements are to take place. As an example, given known variations in breath acetone levels when the measurement is made first thing in the morning as opposed to measurements made in the afternoon, the planner may determine that two measurements will be made each day, one in the morning and one in the afternoon. The planner also may build into the program a specified light lunch, and a daily exercise regime to be undertaken immediately before lunch. Thus, the physiological states specified by the planner at which the breath acetone levels will be measured or determined have been set and correspond to the user's physiological states resulting from those two measurement regimes. As the description of this method proceeds, focus will be on the morning measurement regime to simplify the description. It will be appreciated, however, that the same approach and method steps can be applied to both the morning and afternoon tests and associated physiological states.

The method also comprises determining the breath acetone level of the user at the physiological state for a period of seven days or until the baseline is stable for 4-5 days in a row to determine a user baseline. This aspect of the method is carried out using system 110, under the control of the App as described herein above, to take a morning breath acetone measurement for the user each day for five consecutive days. The measurement results are displayed on the scatter plot as shown with curve 352 in FIG. 8. The App may take the average of the five breath acetone measurement results and plot that average as a baseline (e.g., as a horizontal line 356 on the scatter plot 350).

The method then comprises determining one or more subsequent breath acetone levels, comparing the subsequent breath acetone level against the user baseline to generate a comparison, and outputting the comparison. This may be carried out by having the user use system 110 each morning to measure his or her breath acetone level, which value is inputted into electronic device 130 under the control of the App. The App then compares each of the measured values to the baseline.

The comparison to the baseline can occur in a number of different ways, including simple subtraction. For example, statistical results or relationships, such as those presented in the legends of FIGS. 18A-E, FIG. 19, FIG. 20, and/or FIG. 21, can be displayed by the App. These statistical results or relationships are described in greater detail below. The method may further comprise allowing the user to track events, and associating the events with the results.

As described herein, the App may determine a user baseline, compare ketone measurement results to the baseline, display the comparison, and/or provide other functionality related to the determined user baseline. For example, when the App is executed by the electronic device 130, the App may cause the electronic device 130 to generate a user interface that displays the comparison and/or to provide other functionality described above. As another example, when the App is executed by the remote system 140, a user may use a browser running on the electronic device 130 to access and view a page generated by the App. The page may be interactive such that the user can view the comparison and access the other functionality described above.

Reminders and Interactive Reminders

As has been noted herein above, the present inventors have discovered that the timeliness of ketone measurements and the faithfulness of user compliance with certain program rules regarding breath acetone measurement are particularly important to the success of many programs, and that specifically pre-determined or pre-calculated reminders and interactions with the user can greatly increase program success. Accordingly, the present disclosure according to one aspect comprises systems, devices, and methods for measuring a ketone in the user's breath that comprise, inter alia, the provision of reminders, and interactive reminders.

As explained above, in the relatively inchoate field of breath analysis, most of the data and information available on such topics as patient or user compliance—which has been relatively sparse—have been obtained in clinical settings, where clinical staff was present and patient or user compliance was not a significant issue. More generally, in the general area of diet program compliance, the traditional approach to monitoring patient or user compliance has been for the user to record daily dietary activity in a journal. This approach has been highly deficient in monitoring compliance, and has been vulnerable to intentional non-compliant behaviors. Moreover, these deficiencies normally are discovered, if at all, only after the fact, when they are more difficult to correct or address.

In accordance with this aspect of the present disclosure, a method is provided that uses a system (e.g., one of those described herein above) that includes memory that has stored therein data representing one or more rules relating to a program (e.g., those outlined in Tables 1 and 2) and a reminder set associated with the respective rule or rules. The system may provide the user with at least one reminder in relation to the rule or rules via a user interface. These features can be employed using a software application that is operatively disposed in the system (e.g., the electronic device or the remote system as described in the previously-described system embodiments) to generate the at least one reminder. For example, the reminders may be presented via a mobile application that runs on a smartphone, tablet, smart watch, or other mobile communications device of the user.

The following example, presently in connection with use of system 110 for illustrative purposes, provides a presently preferred but merely illustrative method implementation according to this aspect of the present disclosure.

The App as described herein is loaded into electronic device 130 of system 110, and has been launched by the user. As an example, the following program rules have been selected for the user by the user and/or his or her treating nutritionist or healthcare professional:

Rule 1: Morning Breath Acetone Test: The user will test breath acetone first thing each morning, between a specified time (e.g., 7 am and 9 am), prior to eating any food or drinking any beverages other than water, and before any exercise is performed.

Rule 2: Breakfast: Breakfast may be eaten after the morning breath acetone test, but no later than a specified time (e.g., 10 am).

Rule 3: Prescription Medication: Given the fact that the user takes a prescription medication daily, and in view of the requirements and restrictions of the medication itself, the user will take the medication after the morning breath acetone test, but no later than a specified time (e.g., 11 am).

Rule 4: Resistance Exercise: Each Monday, Wednesday, and Friday, between a specified time (e.g., 12 pm and 2 pm), the user will engage in 20 to 30 minutes of weight or resistance exercise.

Rule 5: Cardiovascular Exercise: Each Tuesday and Thursday, between a specified time (e.g., 12 pm and 2 pm), the user will engage in 20 to 30 minutes of aerobic cardiovascular exercise.

Rule 6: Evening Breath Acetone Measurement: Each evening between a specified time (e.g., 5 pm and 8 pm), the user will take another breath acetone test or measurement. The user may not have eaten any food or consumed any beverage other than water for at least two hours prior to taking the test. The user also shall not have undertaken any exercise exceeding ten minutes in duration within one hour of taking the test.

As described above, the rules may be set by the user and/or his or her treating healthcare professional using a browser (e.g., a web browser) executing on an electronic device, a network-accessible application (e.g., an application executing on a server, such as the remote system 140), an application running locally on the electronic device 130, and/or the like. For example, the user and/or his or her treating healthcare professional may use the browser to log into a content page that allows the third party to view, create, select, and/or set rules. The rules may be stored in memory of the electronic device 130 and/or available via a network connection (e.g., the rules may be stored on a server, such as the remote system 140, and accessible by the electronic device 130). As another example, the user and/or his or her treating healthcare professional may use a user interface generated by the application running locally on the electronic device 130 to view, create, select, and/or set rules and store the rules in the memory of the electronic device 130.

With these six rules stored in memory of the electronic device 130 (or stored remotely in the remote system 140), shortly after waking on Day x of the program, the user may launch the App on electronic device 130, whereupon opening panel 300 of the App (FIG. 7) may be displayed. The user may select the Perform Measurement button 312. Processing of the App from this point forward is illustrated by the flow diagram 400 shown in FIG. 11. Based on the internal clock of electronic device 130, the App (at 402) uses the time of day input to ascertain whether the current time of day is within the permissible 7 am to 9 am morning time window (Rule 1) or the 5 pm to 8 pm evening time window (Rule 6). (Likewise, if a rule is based on location of the user, the electronic device 130 can use an internal GPS or data from an external GPS to determine whether the user is in the proper location.) If not within either, the App (at 404) may display a message indicating that the current time of day is not within the morning time window or evening time window and stop. Alternately, if not within either, the App (at 404) may display the message indicating that the current time of day is not within the morning time window or evening time window, but may allow the user to continue with the measurement. The measurement may be marked as non-compliant and the measurement, along with a notice identifying the data as non-compliant, may be stored in the App and/or transmitted by the App to the remote system 140. The measurement, when displayed to the user or a third party via a user interface, may be marked (e.g., as an X, such as icon 359 in FIG. 8) or annotated as non-compliant to indicate that the measurement did not fall within the Rule 1 or Rule 6 time window. The measurement may also not be used when performing computations, such as computations based on the algorithms described below with respect to FIGS. 18A-22.

If the time of day is within the morning time window, the App may present the user with a pre-test Rule 1 confirmation panel 406, which asks the user to confirm compliance with each of the requirements and restrictions of Rule 1. If the user, via the App, confirms compliance with each of the requirements and restrictions of Rule 1, the App may log compliance confirmations (and other related data or events) and instruct the electronic device 130 to transmit a message to the measurement device 112 that includes confirmation of the compliance and/or an instruction to begin the measurement. The App and/or the measurement device 112 may also transmit the compliance confirmation to the remote system 140 for storage. The measurement may be marked as compliant and the measurement, along with a notice identifying the data as compliant, may be stored in the App and/or transmitted by the App to the remote system 140. Likewise, if the user, via the App, confirms non-compliance with one or more of the requirements and restrictions of Rule 1, the App may log the non-compliance confirmation(s) and any compliance confirmations and/or transmit a message to the measurement device 112 that includes the non-compliance and/or compliance confirmations. The App and/or the measurement device 112 may also transmit the non-compliance and/or compliance confirmations to the remote system 140 for storage.

Figure 11:
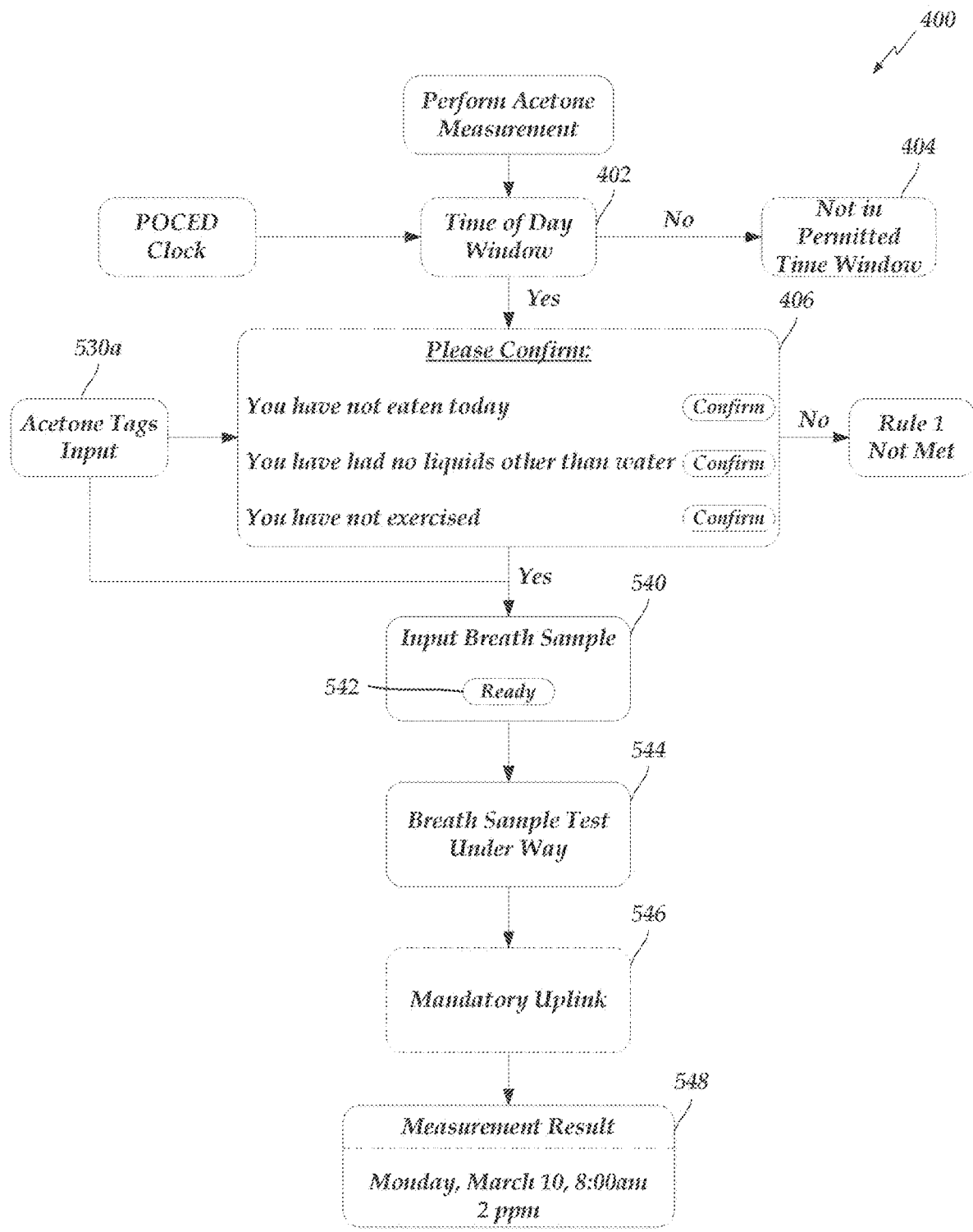
FIG. 11 is a flow chart or diagram that illustrates process flows and displays for the software application, display panels of which are shown in FIG. 7.
Figure 12:
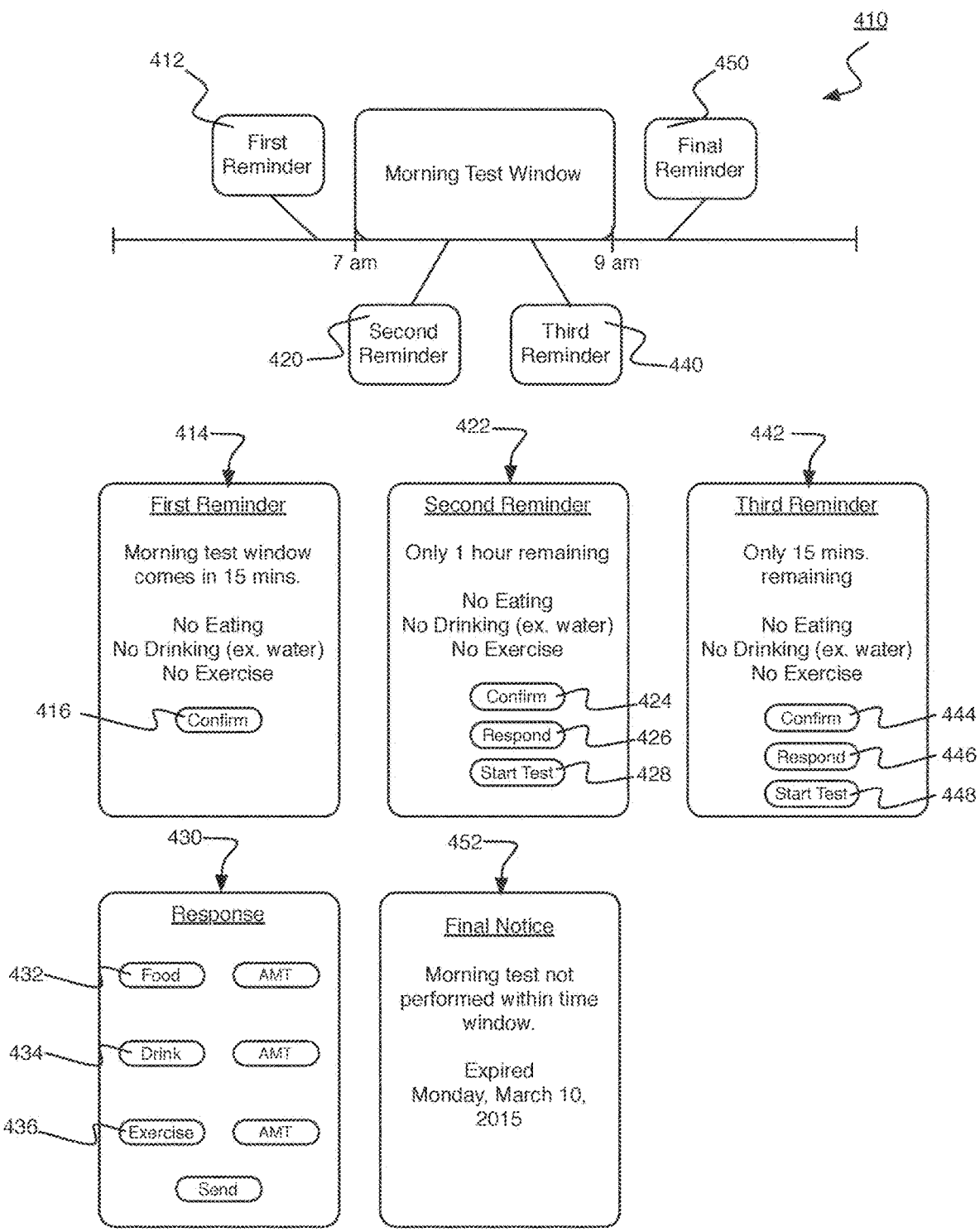
FIG. 12 is a pictorial view of a timing diagram and associated software display panels for providing interactive reminders according to a presently preferred implementation of the present disclosure using the software application, display panels for which are shown in FIG. 7.

The method implementation for the morning breath acetone test embodying Rule 1 as outlined in FIG. 11 can be improved by providing one or more selective reminders that aid in user compliance. An example is illustrated in FIG. 12. Referring to the time line 410 at the top of FIG. 12, the horizontal axis represents time, and the morning test window is shown in block form encompassing the 7 am to 9 am window according to Rule 1. At a predetermined time before commencement of the window (e.g., 15 minutes before the 7 am commencement), electronic device 130, based on input from its clock, provides an audible and/or visual notice perceptible by the user and display a first reminder 412 in the form of a panel 414 providing a first reminder. The first reminder may include a notice or reminder that the morning test window will commence in 15 minutes (in this example), and a reminder to the user that he or she should not eat or drink any liquids besides water prior to conducting the test, and that no exercise is permitted prior to the test. The panel 414 may include a confirmation button 416 for the user to select to confirm receipt of the notice. If confirmation button 416 is selected, the App may time-tag the confirmation and record or store information indicating that the confirmation button 416 was selected. If the user does not select confirmation button 416 within a pre-determined time (e.g., 2 minutes), the App may record and store this non-response.

At a predetermined time within the morning test window (e.g., one hour or, equivalently, half way through), if the morning test has not been commenced pursuant to FIG. 11, the App causes a second reminder 420 to issue, as illustrated in FIG. 12. This second reminder 420 may include an audible and/or visual notice and a second reminder panel 422. Panel 422 may include a notification to the user that only one hour remains in the morning test window and may include a reminder of the other Rule 1 requirements and limitations regarding eating, drinking, and/or exercise. At the bottom of panel 422, the user is presented with a "confirmation" button 424 to confirm receipt of the second reminder, a Respond button 426 to affirmatively respond to the notice, and a "Start Test" button 428 to initiate the test. If confirmation button 424 is selected, this selection is time-stamped and stored in the memory of the electronic device 130. If Start Test button 428 is selected, the App may initiate the morning acetone test as illustrated in the blocks and panels of FIG. 11.

If Respond button 426 is selected, the App presents a Response panel 430, as shown in FIG. 12. The response panel 430 may enable the user to affirmatively respond to the reminder or notice. The response may be in the form of a set of response options, an affirmative numerical response, an affirmative textual response, etc., and/or combinations of these. This response option may be presented in a single panel (e.g., panel 430) or through a series of panels that allow the user to input increasingly detailed information. As shown illustratively in panel 430, the App presents the user in this Rule 1 example with option buttons for food, drink, and exercise (432, 434, and 436, respectively). Associated with each is a button or similar graphic that enables the user to input the amount of food and/or beverage that has been consumed or exercise that has been done. The App also may include one or more additional panels below each of the food, drink, and exercise button options that enable the user to input additional information (e.g., the specific food or beverage consumed, the amount, the time of consumption, etc.). The App may screen these inputs and determine whether the breath acetone test should be canceled, whether the time window for the test should be extended or changed, and/or the like. The App may then indicate the result of the screening. In addition to or as an alternative to this user response and screening functionality of the App, some or all of the features of the App described above may be performed by remote system 140. In this event, the App executed by electronic device 130, which is in communication with remote system 140, can provide the user interface for the communications to and from the user (e.g., the user can access a content page generated by the remote system 140 using the electronic device 130).

At another predetermined time within the morning test window (e.g., 15 minutes prior to the expiration of the window, which in this example, 8:45 am), if the morning test has not been commenced pursuant to the blocks and panels of FIG. 11, the App may cause a third reminder 440 to issue. The third reminder 440 may include another audible and/or visual notice and a third reminder panel 442. Panel 442 may include a notification to the user of the remaining time within the morning test window and again may include a reminder of the other Rule 1 requirements and limitations regarding eating, drinking, and exercise. As with panel 422, at the bottom of panel 442, the user may be presented with a "confirmation" button 444 to confirm receipt of the second reminder, a Response button 446, and a "Start Test" button 448 to initiate the test.

Upon expiration of the morning time window (e.g., at 9:05 am, if the morning test still has not been commenced pursuant to FIG. 11), the App may cause a final notice 450 to issue in the form of panel 452. The final notice 450 may indicate that the morning test was not performed during the morning test window and that the time window has elapsed. The final notice 450 may also provide the day and date so that the user is clearly notified of which test was missed. The final notice 450 may request that the user perform a test even though the time window has expired. If a test is performed in response to the final notice 450, the measurement may be marked as non-compliant in a manner as described above and not used in any future computations by the App or the remote system 140. The App may also provide this information to the user through the Activity panel 330 (FIG. 7).

The App could use a machine-learning algorithm to learn, based on a given user's behaviors, what types of non-compliance events are the most likely (or are most likely in certain circumstances, such as when traveling), and could modify/personalize the reminders accordingly (such as by sending additional or preemptive reminders when the computed likelihood of a non-compliance event is high).

Optionally, as some or all of these reminders and notices are issued, data representing the reminders and/or notices may also be automatically or mandatorily transmitted to remote system 140 (e.g., for storage and/or viewing by a third party). Some or all of the reminders could alternatively (or additionally) be sent as text messages, instant messages, or some other type of message from a server, such as the remote system 140.

In an embodiment, the App varies the timing and/or content of the reminders based on sensed conditions, such as the GPS location and/or physical speed of the mobile device running the App or the usage of other applications on the mobile device. For example, a reminder may be delayed if the App senses that the user is driving, is on a phone call, or is in a location that is not well suited for testing.

Similar reminders, notices, confirmations, and/or responses may be provided by the App for the other program rules. In a reminder prior to the afternoon breath acetone measurement, for example, the user may be reminded of the requirements, limitations, and restrictions of Rules 2-6, and confirmation sought from the user that he or she is in compliance. As with the morning test, failure to confirm the requirements, etc. prior to the test will be noted, failure to commence the test within the evening test window will preclude the test, and so on.

Acetone or Ketone Tags

As described herein, the present inventors have discovered that certain recurring events or conditions, referred to herein as "acetone tags," arise during the course of a typical program that can significantly mask the correlation of the breath acetone measurements with the underlying intracellular fat metabolism and physiological ketone production the measurements are intended to identify. It was also noted above that if these recurring factors are properly identified and accommodated, their undesirable masking effects can be mitigated or eliminated. For the purposes of this disclosure, the term "acetone tag" and the term "ketone tag" may be used interchangeably. In general, an acetone tag may describe a tag used when measuring acetone levels in breath and a ketone tag may describe a tag used when measuring ketone levels in a bodily fluid other than breath (e.g., blood, urine, saliva, etc.) or in an area surrounding a portion of the skin in which ketones have permeated into the open air.

An "acetone tag" is a common or recurring activity or condition relating to the user that may impact the user's breath acetone levels, but which may do so on a relatively consistent basis and is planned or expected, and that lends itself to a separate or segregated data set for the ketone measurement. Acetone tags are used for things, events, conditions, etc. that impact the breath acetone measurement, but which occur on a regular or periodic basis, or at least not uncommonly, so that they can be anticipated and addressed. Examples of acetone tags include: (a) the time of day at which the breath acetone measurement is made (e.g., morning or evening), (b) food or beverage intake within a window of time prior to and/or after the breath acetone measurement test, (c) daily or periodic intake of a specific food or beverage, (d) daily or periodic administration of prescription medication (e.g., before or after the breath acetone measurement test), (e) daily or periodic physical activity, such as a cardiovascular or weight bearing exercise work out (e.g., before or after the breath acetone measurement test), (f) cortisol-impacting factors (e.g., after a good night's sleep or after disrupted sleep), (g) travel, and/or (h) stressful situation.

A particular acetone tag may apply to some or all users. Breath acetone levels generally change for any given user or person depending on when the measurement is made. For example, breath acetone levels may be different if the measurement is made on an empty stomach than if the measurement is made shortly after consuming a sugar or carbohydrate-rich meal.

Not all acetone tags, however, may apply to a given user, or apply prominently or significantly to a given user, particularly in the context of a given weight management or DKA monitoring or prevention program. Some users, for example, commonly exercise daily or periodically and others do not. Similarly, some users have sleep issues and others do not. Therefore, the user, alone or together with a third party, such as a third party support person, typically identifies acetone tags that are expected to apply in a significant way to the user and the selected program. Stated differently, the user and/or the third party selects acetone tags that they wish to address during the course of the program, based on whatever criteria they believe warrants its inclusion.

Once the user and/or third party have selected the one or more acetone tags that are to be addressed, data representing these acetone tags are stored in the breath ketone measurement system. This may be accomplished in a number of ways. With respect to presently preferred systems 10, 110, and 210, data identifying the acetone tags may be stored in the electronic or communications device (e.g., in the memory of the electronic device 130 of system 110 (FIG. 2)) or in the remote system, preferably using a software application such as the App described herein above.

To provide a presently preferred but merely illustrative example, system 110 can be used to demonstrate the storage and use of acetone tags according to this aspect of the present disclosure. It will be recognized, of course, that system 110 is merely an example for purposes of illustrating systems and methods according to this aspect of the present disclosure, but is not necessarily limiting.

Figure 13:
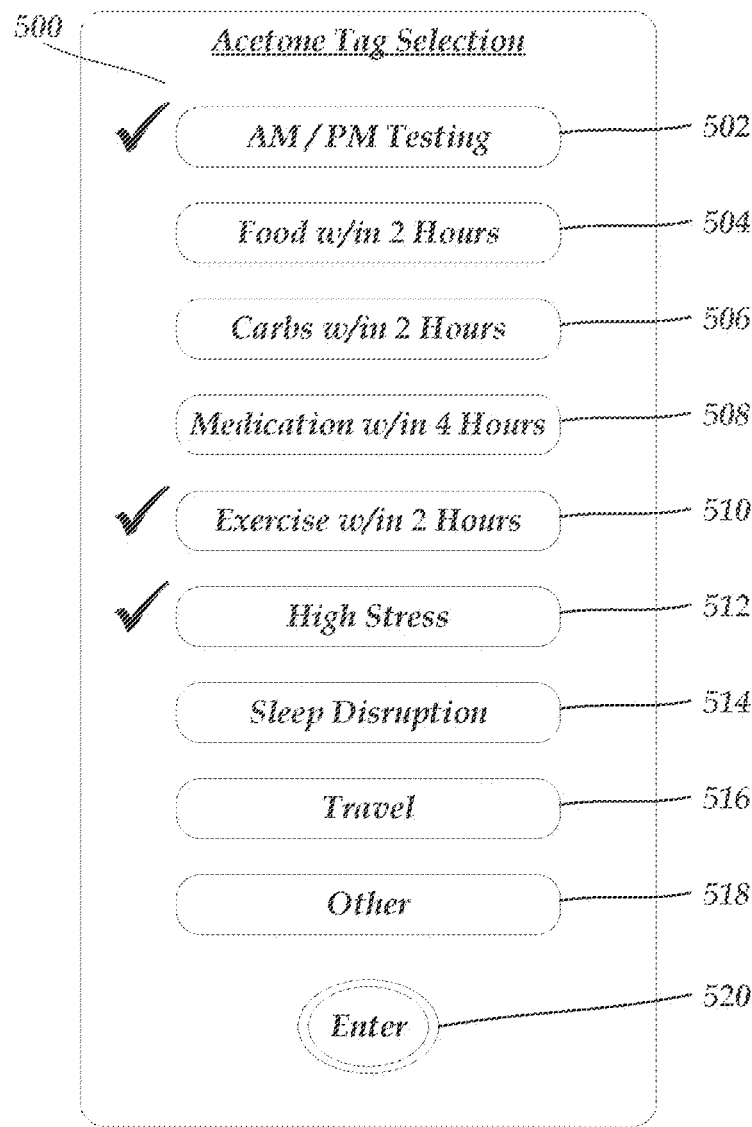
FIG. 13 is a display panel for an electronic device used to select acetone factors according to a presently preferred embodiment of the present disclosure according to another aspect.

The user is presumed to be at a first location with breath ketone measurement device 112 and electronic device 130, the latter of which is loaded with the App as previously described herein and as further described herein below. The acetone tags preferably are entered by the user or a third party support person into electronic device 130 via an option on the Charts panel 340 or the Settings panel 360 (FIG. 7). Alternatively, the acetone tags may be entered by the user on a content page generated by the remote system that is associated with the user and that is accessible over a network. If the user enters the acetone tags on the content page, the remote system may transmit the entered acetone tags to the electronic device 130 via the network. In this illustrative example, the Settings panel 360 is used. With reference to FIG. 7, the user launches the App, which presents opening panel 300. The user then selects Settings button 310 at the bottom of the opening panel 300, which causes the Settings panel 370 to open. One of the options on Settings panel 360 is an Acetone Tag Selection tab (not shown). Upon selection of that tab, an Acetone Tag Selection panel 500 as shown in FIG. 13 is presented. Acetone Tag Selection panel 500 provides several (e.g., nine) pre-stored options for available acetone tags: an AM/PM Testing button 502, a Food w/in 2 Hours button 504, a Carbs w/in 2 hours button 506, a Medication w/in 4 hours button 508, an Exercise w/in 2 hours button 510, a High Stress button 512, a Sleep Disruption button 514, a Travel button 516, and an Other button 518. AM/PM Testing button 502 allows the user to select morning versus afternoon testing as an acetone tag. When this button 502 is selected, the App may segregate ketone measurements made in AM hours from those made in PM hours. Food w/in 2 Hours button 504 permits the user to select as an acetone tag whether or not the user has eaten food within the two hours preceding a ketone test. Similarly, Carbs w/in 2 hours button 506 permits the user to select as an acetone tag whether the user has eaten carbohydrates within the two hours prior to a ketone measurement. Medication w/in 4 hours button 508 allows the user to select as an acetone tag whether he or she has administered medication within the four hours preceding a ketone test. Exercise w/in 2 hours button 510 allows the user to select as an acetone tag whether the user has engaged in exercise in the two hours preceding the ketone measurement. High Stress button 512 allows the user to select as an acetone tag whether or not the user has been in a high stress condition prior to the ketone test. Sleep Disruption button 514 permits the user to select as an acetone tag whether he or she has experienced sleep disruption during the night preceding a ketone test. Travel button 516 allows the user to select as an acetone tag whether the user has been traveling immediately prior to or at the time of the ketone test. Finally in this example, Other button 518 allows the user to designate a general acetone tag or to designate an acetone tag or category different from those presented in FIG. 13. Upon selecting any one of these buttons, the App may present further panels and/or further options for more specifically identifying or designating the respective acetone tags. At various times (e.g., when setting up a new weight management or DKA monitoring or prevention program), the user, alone or with a third party support person, may review panel 500 and make the appropriate selection or selections from the available acetone tag options and select the Enter button 520, whereupon the App saves these selections and returns to opening panel 300.

In the example illustrated in FIG. 13, the user selects three acetone tags from the available options (AM/PM Testing button 502, Exercise w/in 2 hours button 510, and High Stress button 512), as indicated by the check marks in FIG. 13.

It should be noted that there are other ways to enter or select acetone tags, and the foregoing example is illustrative but not necessarily limiting. Acetone tags also may be entered at remote system 140, for example, in a manner as described for their entry into electronic device 130, and downloaded to electronic device 130 for use by the App as further described herein below.

After the acetone tag or tags have been selected, entered, and stored, the system may be ready to be used in its normal operation to measure breath acetone levels in the user's breath samples, for example, in support of a weight management or DKA monitoring or prevention program, albeit while employing the acetone tags features. This operation will now be described as a continuation of the use of system 110 and this preferred method implementation.

Figure 14:
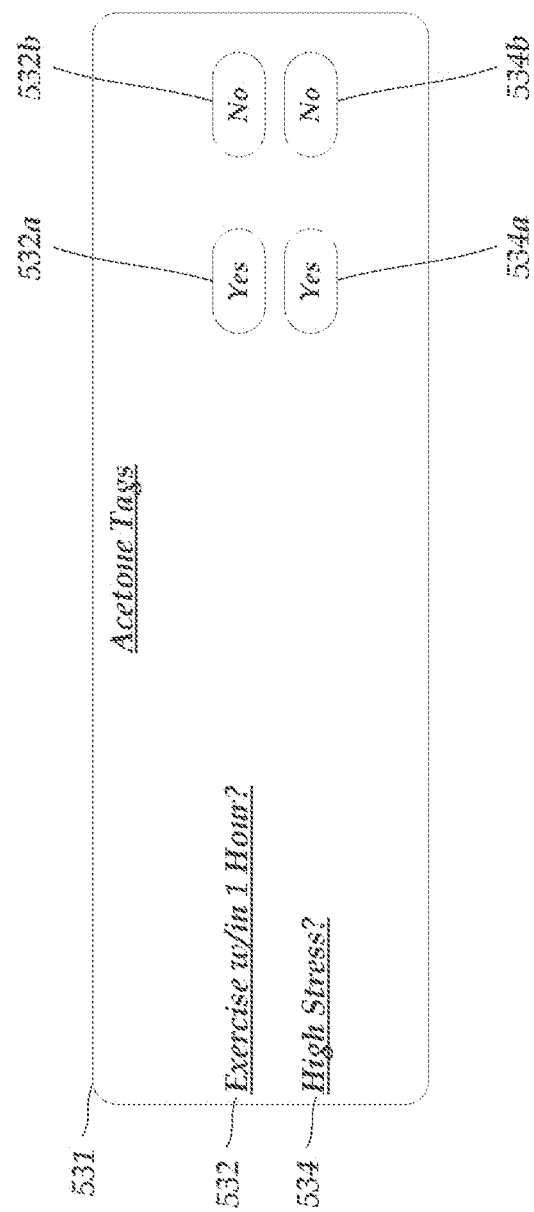
FIG. 14 is a display panel for presenting selected acetone tags in the preferred method implementation associated with the display of FIG. 14.

With reference to FIGS. 2 and 11, the user launches the App on electronic device 130 and, upon presentation of opening panel 300, selects Perform Measurement button 312. As shown in FIG. 11, the App receives the time of day from the electronic device clock, and automatically registers that the ketone measurement (at 402) is an AM test (or a PM test) for purposes of the AM/PM acetone tag. The App then (at 530*a* in FIG. 11) may present an Acetone Tags panel 531 (FIG. 14), which lists the Exercise w/in 2 hours 532 and High Stress 534 acetone tags and for each provides a Yes button (532*a*, 534*a*) and a No button (532*b*, 534*b*). For each such acetone tag, the user may select the Yes or No button, where Yes indicates that the user has engaged in the acetone tag or that the acetone tag otherwise applies, and where No indicates that the user has not engaged in the acetone tag or that the acetone tag otherwise does not apply. In an embodiment, only the acetone tags selected by or for a particular user are presented as options at measurement time (e.g., after the Perform Measurement button 312 is selected) in the Acetone Tags panel 531. Thus, the burden placed on the user in categorizing the measurements may be minimized as the user may not have to select a state for each possible acetone tag. This may also reduce the storage burden on the App, the measurement device 112, and/or the remote server 140 because only the states associated with the acetone tags selected by or for the particular user would be stored. By presenting as options only the acetone tags selected by or for the particular user, the likelihood of capturing the most relevant activity or condition information for the particular user may be significantly increased.

The acetone tags as described herein above are such that they generally can be presumed to take one of only two possible states (e.g., yes or no). This is not, however, limiting. More than two states are possible. Moreover, even where there are only two states, they need not be simply yes or no, and may assume other forms (e.g., high and low, 0 or 1, and so on). Accordingly, for a given acetone tag, the selection of the state of the acetone tag may vary depending on the possible states. These various states or options for an acetone tag are referred to as an "acetone tag state." In the preceding illustrations, for example, a "Yes" is an acetone tag state, as is a "No."

Upon selection of the Yes and/or No buttons for the acetone tags, the App may then proceed to the Input Breath Sample panel 540 as shown in FIG. 11. The user may input the breath sample in system 110 by exhaling into mouthpiece 116 and selecting the Ready button 542 on touch screen 134, whereupon measurement device 112 measures the breath acetone concentration, generates a measurement signal indicative of that acetone concentration, and communicates it to electronic device 130 and correspondingly to the App. During the operations performed by the measurement device 112, the App may display the "Breath Acetone Test Under Way" message (at 544). Optionally, this measurement signal may be automatically and mandatorily transferred in an uplink transmission to remote system 140 (at 546). The measurement result may also be displayed to the user in a user interface generated by the electronic device 130 (or the measurement device 112 in alternate embodiments) (at 548).

As the user continues with the program, this process may be repeated so that a plurality of the user's breath samples are measured sequentially over time and a corresponding plurality of ketone measurement results are obtained and stored in electronic device 130 and/or remote system 140. Each of the breath acetone measurement results as stored may include a reference or identification number, a date and time, a corresponding indication of AM versus PM testing, and/or an indication of the acetone tag state for each applicable acetone tag.

Figure 15:
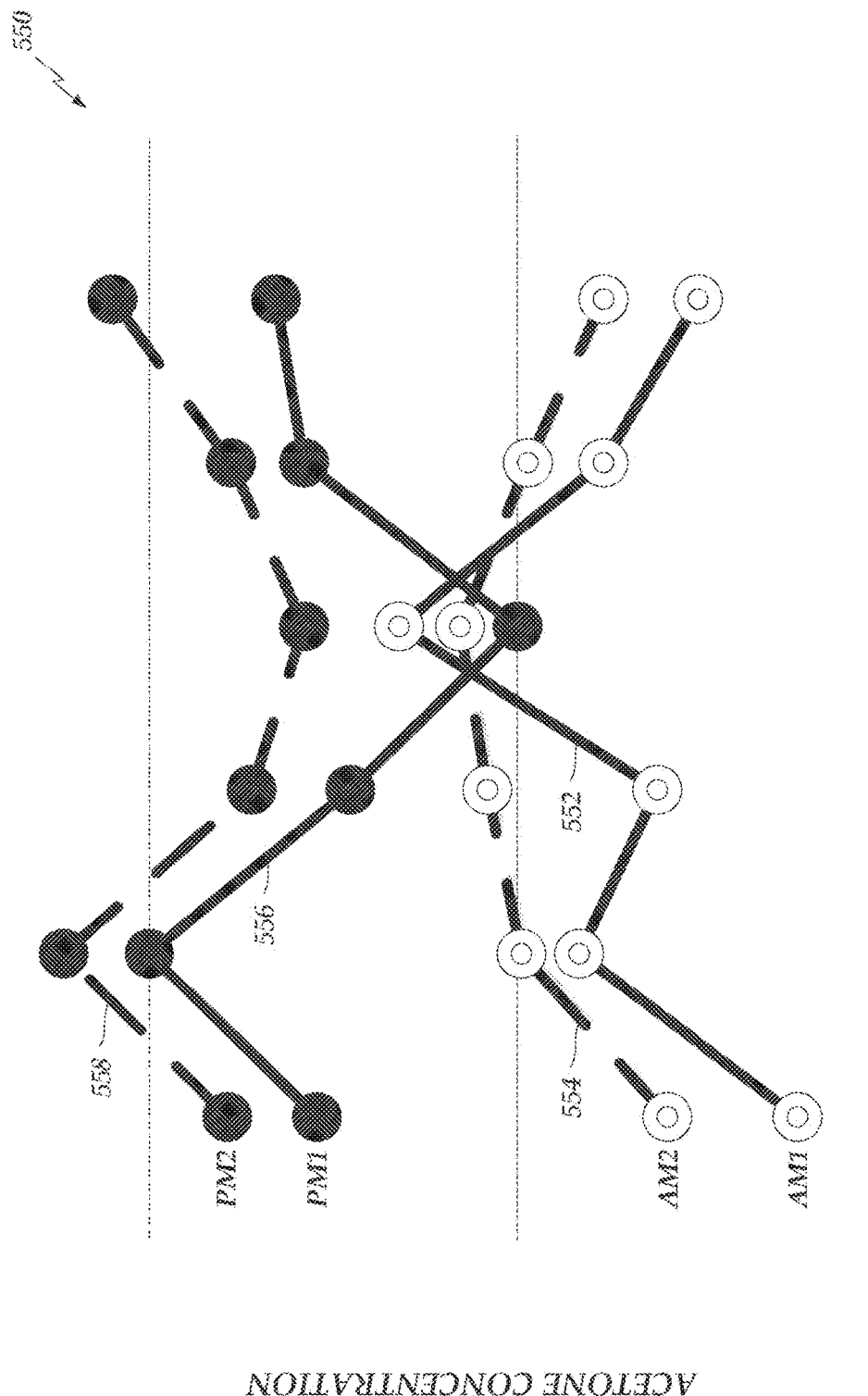
FIG. 15 a scatter plot display output of breath acetone measurement data provided by the software application, display panels for which are shown in FIG. 7, and displaying the data according to acetone tags of FIG. 14.

Upon displaying the measurement data, the App—automatically or under the control of the user—can display the data segregated by acetone tag states or categories. An example is provided by the data plot 550 in FIG. 15. As in FIG. 8, the horizontal or x-axis represents the day of the program and the vertical or y-axis represents the measured acetone concentration. Four curves or plots (552, 554, 556, and 558) are presented. The bottom curve, designated as "AM1" (552) represents morning measurements made with no exercise for the two hours prior to the tests. The "AM2" curve (554) also represents morning measurements, but with exercise within the two-hour period preceding measurement. Similarly, the "PM1" curve (556) represents afternoon measurements made with no exercise during the two hours prior to the tests, and the "PM2" curve (558) represents afternoon measurements, but with exercise within the two-hour period preceding measurement. Given that, in this example, the acetone tag of "high stress" also has been recorded, a similar graph to that of FIG. 15 could easily be generated from the data, or the additional curves associated with the stress data could be overlain on the curves in FIG. 15. The curves in the graph may be color-coded or visually marked in some other way and displayed with a key that associates each color or visual marker with the corresponding acetone tag such that the curves associated with the different acetone tags are easily identifiable.

Trigger Points

The present inventors also have discovered, as described herein, that user-specific "trigger points" often create unduly high risks of program non-compliance. If these trigger points are identified and managed, the probability and extent of program success can be greatly increased.

Based in part on user interviews and the present inventor's extensive research and development in the field, it has been discovered that most users are able to identify a relatively small number of unplanned activities, events or things, referred to herein as "trigger points," that most commonly cause the user to break these rules or engage in disfavored actions.

A "trigger point," in the context of weight management applications, is an event, activity, behavior, or item that may trigger or cause behavior that is adverse with respect to a weight management objective of the user. The trigger point may or may not be planned or expected, but the undesirable or disfavored response by the user is unplanned and generally unexpected. Examples of events that may represent a trigger point include festive events such as a party, anniversary, weekends, travel, and/or the like.

Examples of activities that may represent a trigger point include stressful tasks (e.g., a difficult work task, giving a public presentation, attending a job interview, watching an action movie or sporting event, entertaining with friends, night eating, and so on). Examples of items that may represent a trigger point include certain types of foods (e.g., high caloric, sugary or otherwise unhealthy foods, alcoholic beverages, tobacco, snacks), certain medications (e.g., medications that promote hunger, pain, stressful mental states, such as depression, loneliness, and anxiety, and so on), and/or the like. Examples of adverse behaviors that a trigger point may threaten include eating prohibited or disfavored foods, eating at prohibited or disfavored times (e.g., at night), drinking prohibited or disfavored beverages, drinking at prohibited or disfavored times, eating or drinking excessive amounts, and so on.

A "trigger point state" may be a state or condition that is often associated with a particular trigger point. An example of a trigger point state may be in the morning on the way to work (the state), which gives rise to the trigger point of drinking sugar-laden coffee.

A trigger point, in the context of weight management, may be thought of in more colloquial terms as something that presents a high-risk temptation to a specific user to "cheat" on a weight management or DKA monitoring or prevention program or violate the rules of that program. A good example, although certainly among many, would be an event such as a party, at which the various participants are drinking high-calorie beverages, eating high-caloric or sugar or carbohydrate-rich foods. In these surroundings and under these circumstances, even a user that has reasonably good discipline might be tempted to consume those high-calorie foods and beverages in violation of the user's dietary rules.

Somewhat in contrast to acetone tags, the occurrence of which generally are fairly foreseeable and predictable, the identification of specific trigger points often may not be difficult but their occurrence (e.g., specifically when the user will encounter a trigger point) may be relatively unpredictable, at least in the context of planning a program.

The trigger point feature described herein may be applicable to other types of programs that are susceptible to non-compliance events. For example, such programs may include exercise regimens and certain types of diets that do not seek to achieve weight loss.

Figure 16:
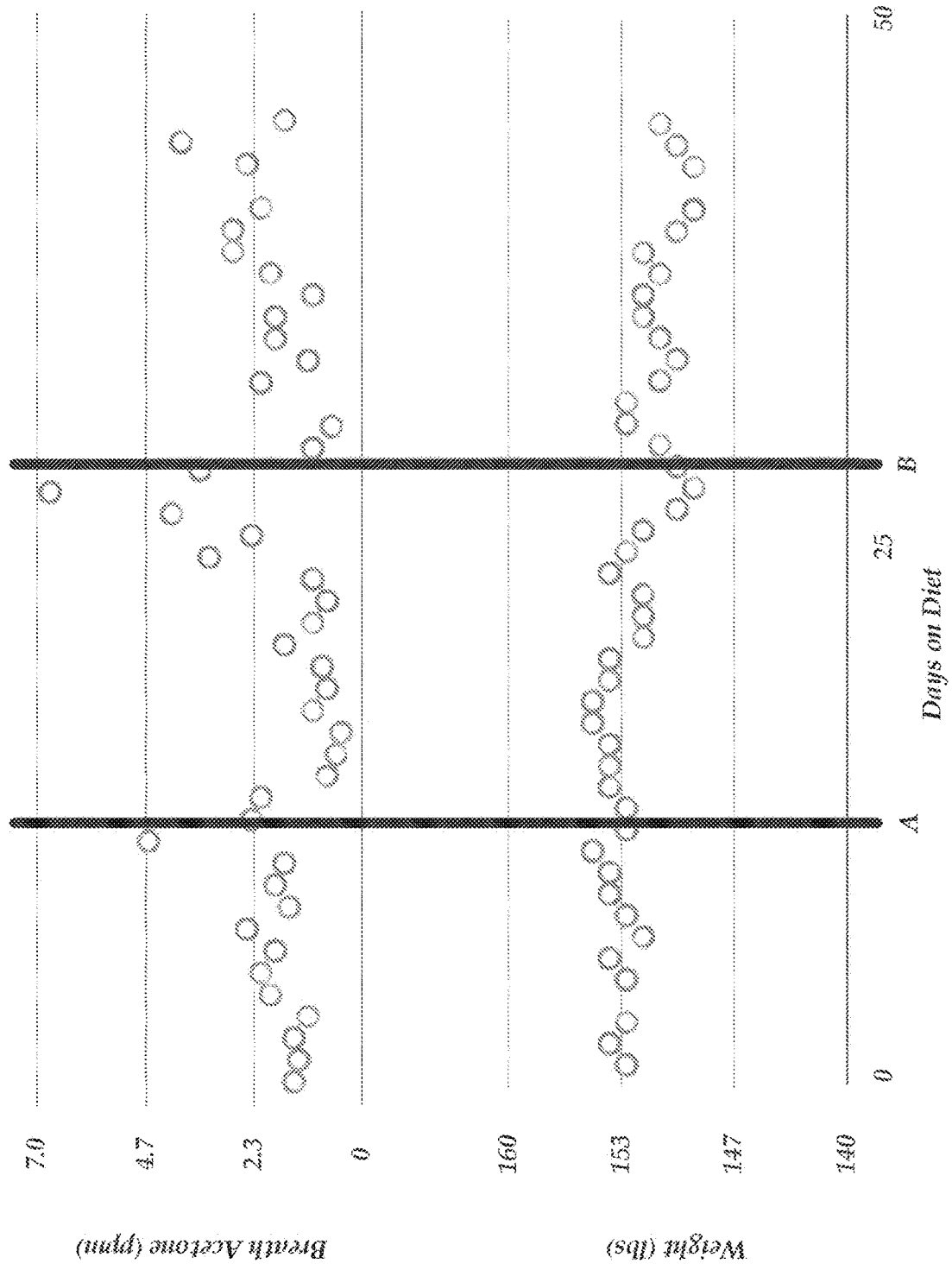
FIG. 16 shows a graphical chart displaying breath acetone levels and various events.

To illustrate the effect of these trigger points, consider the breath acetone measurement results data shown in FIG. 16. The events demarcated with "A" and "B" are both non-compliance events. Event "A" was centered around a holiday and event "B" was the user's birthday. Between the time periods of "A" and "B," the user was showing an increase in breath acetone levels, which may suggest that the treatment program at those points was effective. When the user's trigger points of a holiday and birthday were encountered, though, non-compliance and setback resulted. Thus, by clearly identifying and managing these trigger point events, the user can benefit from decreasing the frequency of these non-compliance events.

Accordingly, in preferred method implementations according to this aspect of the present disclosure, data identifying one or more trigger points and associated ketone states may be stored in memory of an electronic device or in the remote system. For example, the user or a third party may enter one or more trigger points via the App executed by the electronic device. As another example, the user or a third party may enter one or more trigger points on a content page generated by the remote system that is associated with a particular user. If the trigger points are entered on the content page, the trigger points may be transmitted to the electronic device by the remote system over a network. A user may then use a portable measurement device to analyze one or more of the user's breath samples and to obtain corresponding ketone measurement results. An application (e.g., the App) executed by the electronic device, the portable measurement device, or the remote system may then process the ketone measurement results and the ketone state to determine whether the trigger point occurred.

A "ketone state" may comprise an acetone concentration level, a set of acetone concentration levels, a pattern of such levels or data points, and/or the like, that are associated with the trigger point. For example, if the trigger point involves eating rich foods at a party, the ketone state associated with that trigger point may comprise a pattern of acetone concentration measurement results that show a drop in acetone concentration levels. The ketone state may be determined based on a prior analysis of acetone concentration levels when a known trigger point occurred.

The processing of the ketone measurement results and the ketone state may comprise comparing the acetone or ketone measurement results against the ketone state. For example, the values of the acetone or ketone measurement results may be compared with the pattern identified by the ketone state to see if the values match or closely match the pattern (e.g., within a threshold value). If there is a match or a substantially close match (e.g., a match within a threshold value or percentage), the measurement device or the electronic device may determine that the trigger point occurred. The measurement device or the electronic device can report this determination to the user and/or to a remote system. The measurement device or the electronic device can also generate an inquiry to be presented to the user such that the user can confirm or explain the determination, and so on.

The following is one example of how the above-described trigger points feature may be set up and used in the context of a weight loss program. Initially, a weight loss coach interviews a program participant and uses a web-based or other portal (which may be hosted by the remote system) to set up an account profile for the participant. During this process, the weight loss coach identifies a limited number of trigger points (e.g., 3 or 4) associated with the participant, and specifies these trigger points via the portal (such as by selecting from a predefined list of possible trigger points). In the example shown in FIG. 17, three such trigger points are specified: "drink soda," "eat chocolate" and "drink coffee." The weight loss coach may also be able to associate each such trigger point with a corresponding trigger point state (e.g., "at work"), as shown in FIG. 17. The trigger point states may, for example, specify when, where, and/or under what conditions the trigger points typically occur for the participant.

The program participant would also be provided with the portable measurement device, and with instructions for downloading the associated mobile application to the participant's smartphone or other mobile communications device (tablet, smart watch, etc.). Upon installing the mobile application and completing the pairing process, the mobile application would connect to the remote system (40, 140, 240) and retrieve configuration information, including the trigger point data entered by the weight loss coach and/or acetone tags and/or rules that may also be stored in the remote system (40, 140, 240). Thereafter, whenever the participant uses the portable measurement device to take a ketone measurement, the mobile application prompts the participant to indicate whether any of the designated trigger points apply to the measurement. For example, the mobile application may ask the user to indicate which of these trigger points have occurred "since the last measurement" or "in the last six hours." The mobile application reports these trigger point occurrences to the remote system together with the associated measurements.

The data (measurements and trigger point events) captured through this process may be analyzed by the mobile application, the remote system, and/or a separate system component to search for correlations between particular trigger points and acetone levels. For example, once the system has logged a threshold number of occurrences (e.g., 3, 4 or 5) of a given trigger point (e.g., "eat chocolate") together with associated ketone measurements, the system may use an appropriate correlation algorithm to determine whether a statistically significant correlation exists. This analysis may, for example, reveal that the participant's acetone level drops by 15% to 25% when the trigger point occurs. This learning process may continue as subsequent occurrences of the trigger point are recorded, such that the correlation is refined over time.

The correlations detected through this process may be used by the system to generate appropriate messaging to the participant and/or others. For example, the system (e.g., the mobile application or the remote system) may detect, based on the most recent measurements, that a 20% drop has occurred, and that this drop correlates with the participant's "each chocolate" trigger point.

Other factors associated with the latest measurement, such as the time, day of week, or location, may also be considered to assess whether the trigger point has likely occurred. For example, if a trigger point typically occurs at a specific time or location or under specific conditions, trigger point state information can be used to assess whether the trigger point has likely occurred. The trigger point states may be determined using apparatuses that are able to determine the participant's state without involving the participant. For example, a clock can determine if the trigger point was logged at 2 pm (while the participant is at work) versus 8 pm (while the participant is at home). In some cases, a participant may be in one of several locations at a given time. A location sensor (e.g., a GPS) can determine if the trigger point was logged at the gym (at 6 pm) versus at home (at 6 pm). Moreover, if, for example, the trigger point "drink coffee" is associated with the trigger point state "at night before bed," the system may exclude this particular trigger point from consideration unless the latest measurement was taken between 7 PM and 1 AM. Furthermore, as described below, a biofeedback monitor such as a heart rate monitor or blood pressure meter can determine if the trigger point occurred when the user had recently experienced stress (due to a spike in heart rate, for instance). Trigger point states may further aid the software application by causing the software application to either (a) directly log that the trigger point occurred; or (b) provide the participant with a more accurate proposed explanation for a change in ketone measurements, which the participant may then confirm, change or ignore (e.g., the detected occurrence of a trigger point may cause the software application to modify the values of one or more ketone measurements, possibly pending participant approval).

If the system determines that a particular trigger point has likely occurred, it may prompt the participant (e.g., via the mobile application) to indicate whether this particular trigger point has recently occurred, may notify the weight loss coach of the possible occurrence, and/or revise the values of past ketone measurements. The system may determine that a particular trigger point has likely occurred if, for example, the system determines that a location (e.g., detected by a location sensor, such as a GPS) or condition (e.g., heart rate detected by a heart rate monitor, blood pressure detected by a blood pressure monitor, etc.) of the participant when a ketone measurement was taken (referred to as a ketone measurement state) matches a trigger point state, thereby indicating that a trigger point associated with the trigger point state may have occurred.

The process by which the trigger points feature is set up and used may differ for other types of programs. For example, the system may be used by a marathon runner to monitor progress in training for a marathon. In such cases, the runner (rather than a coach) may directly enter the trigger points, and these trigger points may represent particular types of training-related events (e.g., missed day of training, interval training, etc.).

As noted above, the present inventors have discovered that, in many cases, a given user is particularly tempted only by a relatively limited set of trigger points, and those trigger points tend to be highly user-specific. Thus, an initial step or task may involve identifying trigger points that are significant to the particular user and that may pose a particularly high risk of non-compliance for the user. The selection of such trigger points may involve subjective decision making and discretion may be used in identifying which trigger points are to be used, how many, and so on.

In related method implementations, a user can establish a set of trigger points and corresponding breath acetone levels or ketone states. The user may then use the measurement device to take periodic ketone measurements (e.g., as prescribed in the applicable weight management or DKA monitoring or prevention program). A software application such as the App described herein may monitor the ketone measurements. If one or more ketone measurement results are in or at a trigger point level or match or closely match a ketone state, the system under the control of the App (e.g., the electronic device or the remote system) may undertake a response. That response may comprise a notice to the user that a trigger point is suspected (e.g., simple notice, encouragement, warning, etc.). The response may alternatively or in addition comprise an inquiry, a question (e.g., a question like "Has the trigger point occurred?" that the App presents to the user), an alert, or another prompt directed at the user that may request the user to interact with the system to provide a reply to the response. The response also may comprise a notice to a third party that a trigger point is suspected. Examples of such third parties may include a friend or family member, a group support member, a clinical treatment monitor or advisor (e.g., treating physician, nurse, nutritionist, etc.), and/or the like.

FIG. 17 illustrates a specific implementation of the method described herein. In this implementation, Step 1 involves receiving indications of three user-specific trigger points. The indications of the user-specific trigger points may be received, for example, via an interactive user interface of the App or via a content page generated by the remote system (or via a user interface of the breath analysis device in alternative embodiments). These trigger points may be identified, for example, by a healthcare provider after consultation with the specific user, or they may be identified by the user, or they may be deduced from evaluation of historical diet or exercise journals. In this example, each trigger point may be associated with a trigger point state, which is associated with a time of day (e.g., a time when the user is at work, a time at night before the user goes to bed, etc.). The user-specific trigger points are preferably selected from a predefined list presented by the user interface; however, the system may also support the ability for a user to define a new trigger point.

According to Step 2 of this example, the breath acetone levels may be monitored using a breath analysis device and/or software application. A button to begin the breath acetone test may be identified as "Perform Measurement." Above the "Perform Measurement" button are three custom buttons based on the user-specific trigger points (e.g., in this case the three trigger points described above).

The user may utilize this illustrative software application for a pattern recognition time period. During the pattern recognition time period, the application may identify one or more patterns in breath acetone levels that represent aberrant behavior. For example, the user or a third party may log the occurrences of trigger points during this pattern recognition time period. The breath acetone measurements associated with the occurrence of a specific trigger point (e.g., one or more breath acetone measurements that immediately preceded and immediately succeeded the occurrence of the specific trigger point) may be used to identify a pattern of breath acetone levels that result when the specific trigger point occurs. The pattern may be identified by comparing breath acetone levels that resulted each time the specific trigger point occurred (if the specific trigger point occurs multiple times during the pattern recognition time period).

After the pattern recognition time period, the application may use identified patterns to help the user log events that the user may have inadvertently forgotten to record (or intentionally omitted). Because the identified patterns may be associated with known trigger points, specific prompts can be presented to the user. An example prompt displayed to the user may state "This drop in breath acetone levels looks similar to a drop seen during your night eating of chocolate. Did you forget to log this?" as illustrated in FIG. 17. Preferred methods involve logging user-specific trigger points.

User-specific trigger points may be specific to the individual. These trigger points may change during the course of the individual's weight loss or weight management program. For instance, user-specific trigger points during the "initiation" phase of a diet may involve foods that cause cravings to the user. On the other hand, user-specific trigger points during the "maintenance" phase may be extended vacations where friends are overeating.

User-specific trigger points may further be associated with trigger point states. Trigger point states may be, for example, location and/or time of day. A specific example might be that an individual gets coffee with sugar and cream every morning on the individual's way to work. In this example, the trigger point (e.g., consumption of sugar-laden coffee) is associated with a trigger point state (e.g., morning, on the way to work).

The notion of trigger-point monitoring may allow the user to focus on documenting limited data. Trigger-point monitoring may also be the most critical data to facilitate behavioral changes. In this way, trigger-point monitoring is a potent treatment tool and reflects a paradigm shift from current thinking.

Another preferred method for this aspect of the present disclosure involves establishing a pattern associating certain user-specific trigger points with breath acetone levels. Once the pattern has been established, the pattern may be useful to then monitor subsequent breath acetone levels on a regular basis. The pattern and the breath acetone levels may be used to generate a prediction regarding whether the user-specific trigger point occurred. The prediction may be reported to the user (e.g., via a user interface generated by the electronic device or via a content page generated by the remote system and accessible over a network) so that the user may confirm or clarify the prediction.

The term "on a regular basis" as it pertains to monitoring breath acetone levels is not meant to be narrowly construed (e.g., to require a fixed repeated routine). A regular basis may be cyclical (e.g., every morning, three times a week, and/or the like). A regular basis may also be centered around non-cyclical events. For instance, a regular basis may include the monitoring of breath acetone levels 15 days before and after some or all family vacations.

The above method involves correlating occurrences of user-specific trigger points with breath acetone levels to determine or establish a pattern of breath acetone levels associated with the user-specific trigger point. This may be achieved by receiving a selection or other indication of user-specific trigger points and enabling the user to indicate when any one of the user-specific trigger points occurs (e.g., by prompting the user when acetone measurements are taken) during a pattern recognition time period during which breath acetone measurements are received from a breath acetone measurement device. Times during which the user indicates that a user-specific trigger point has occurred may be stored. At a later time, breath acetone measurements associated with a time near the time during which a user-specific trigger point has occurred (e.g., within 24 hours of a time during which a user-specific trigger point has occurred) and/or a threshold number of breath acetone measurements that occurred around the same time as when a user-specific trigger point occurred (e.g., the 2 breath acetone measurements that immediately preceded the time that the user-specific trigger point occurred and the 2 breath acetone measurements that immediately succeeded the time that the user-specific trigger point occurred) may be used to determine a pattern of breath acetone levels that are stored as identifying an occurrence of the user-specific trigger point. For example, the pattern may be determined based on the percent change between the values of the breath acetone levels before the user-specific trigger point occurred and the values of the breath acetone levels after the user-specific trigger point occurred. As another example, the pattern may be determined based on a comparison of the change in values of breath acetone levels each time the user-specific trigger point occurs (if the user-specific trigger point occurs multiple times). If the change in values before and after the occurrence of a trigger point is a decrease of 10% (e.g., the first time the trigger point occurs), 12% (e.g., the second time the trigger point occurs), and 14% (e.g., the third time the trigger point occurs), for example, a combination of these values may be taken to determine the pattern (e.g., a mean of the percent changes could be taken such that the trigger point is identified in subsequent breath acetone measurements when a breath acetone level drops 12%, a range of the percent changes could be taken such that the trigger point is identified in subsequent breath acetone measurements when a breath acetone level drops between 10%-14%, etc.).

A "pattern recognition time period" may be a period of time sufficient to enable determination of a relationship between the breath acetone levels and one or more of the user-specific trigger points. This period may be different from user to user. Moreover, this period may depend on how frequently a trigger point occurs for the given user. For example, the App may wait for a minimum number of trigger points to occur (e.g., 3, 4, 5, etc.) before attempting to determine a pattern of breath acetone levels associated with the specific trigger point. In some embodiments, the pattern recognition time period is an indefinite period of time because the App may continue to determine new patterns or update existing, recognized patterns as breath acetone measurements are taken.

Additional examples of how the pattern may be determined during the pattern recognition time period and whether, based on determined patterns, current ketone measurements may cause the App to identify that a trigger point occurred are described below. Like many chemical measurands, ketone levels in the body are subject to variance. It is not atypical, for instance, for an individual at a physiological "steady state" to have ketone levels that vary from time to time. A significant change in ketone measurements, such as those associated with a clinically significant trigger point, may be determined by comparing some characteristic of the post-trigger point levels to some characteristic of the pre-trigger point (e.g., steady state) levels. Examples of characteristics include: mean, median, standard deviation, a multiplier of the standard deviation, coefficient of variance, and/or the like and may also involve combinations of these characteristics.

When comparing these characteristics, simple subtraction may be used or a more complex comparison, such as those used in determining signal to noise ratios, may be performed. In effect, the post-trigger point state is the "signal" and the pre-trigger point state is the "noise." Using an appropriate algorithm (examples of which are presented in this disclosure), the signal and noise are distinguished.

Example 1

An example of steady state variance in breath ketone measurements for a healthy individual who is not dieting or exercising is shown in Table 3.

TABLE 3

| Day | Breath Acetone (ppm) |
|---|---|
| 1 | 0.2 |
| 2 | 0.4 |
| 3 | 0 |
| 4 | 0.5 |
| 5 | 0.3 |
| 6 | 1.3 |
| 7 | 0.3 |
| Mean | 0.43 |
| St. Dev. | 0.42 |

In this example, this individual's steady state breath ketone measurements over the course of a week have an average of 0.43 ppm and a standard deviation of 0.42 ppm. Now consider the situation in which the Day 8 level is 0 ppm. In this example, despite the fact that the Day 8 level is less than the Day 7 level, because the difference is less than the standard deviation, this difference is not considered significant. Thus, the software application may not prompt the user to confirm or deny that a trigger point occurred between the ketone measurement taken on Day 7 and on Day 8.

In this example, the computation of the standard deviation was done over 7 days, but in other instances, a shorter or longer duration may be used.

Example 2

The relationship between trigger points and ketone measurements may and often are specific to an individual or to a class of individuals. In other words, not all individuals respond in the same way physiologically to macronutrients, micronutrients, activities or situations. An example of a non-universal trigger point is artificial sweeteners. Exemplary data is presented in Table 4. In this example, the user consumed artificial sweetener between the fifth measurement (M5) and the sixth measurement (M6).

In Table 4, the first column is the measurement number (M #, where # represents the sequential ordering of the measurements taken by the ketone measurement device). The second column shows the output of the ketone measurement device. The third column shows whether or not the software application prompted the user to confirm or deny that a trigger point occurred. The fourth column presents exemplary rules that enable the software application that determined whether or not the software application should prompt the user, as shown in column three.

TABLE 4

| Measurement | Output of the Ketone Measurement Device, Breath Acetone (ppm) | Trigger Point Prompted? | Rationale for Not Prompting for Trigger Points (M = measurement) |
|---|---|---|---|
| M1 | 6 | No | First measurement |
| M2 | 8 | No | M2 > M1 |
| M3 | 10 | No | M3 > M2 and M3 > M1 |
| M4 | 5 | No | (M4) > (at least one good point minus device precision) |
| M5 | 7 | No | [Average (M1 to M4) − Stdev (M1 to M4)] < M5 < [Average (M1 to M4) + Stdev (M1 to M4)] |
| M6 | 2 | Yes | — |
| M7 | 4 | No | M7 > M6 |

Exemplary Algorithm M2>M1. As shown in the row for M2, if a measurement is greater than the preceding measurement, generally the software application does not prompt the user to confirm. There are exceptions, however, such as if the user is failing to recover from an already confirmed trigger point event within a known period of time. For example, if the user is able to recover from administration of an artificial sweetener within 3 days and has not recovered by Day 4, the software application may prompt the user to confirm that subsequent episodes of the same or a different trigger point have occurred. This is not atypical in the event of a major "cheating episode" where a user begins to spiral downward and consume increasing amounts of a trigger point. Another situation in which an individual may not recover within a regular recovery period is athletic injury. An athlete may sprain his or her ankle (a first trigger point) and it is known that recovery takes 2 days. However, as a result of the sprained ankle, the athlete stops working out for those 2 days, but now has two hours of free time in the evening, which is spent at social activities where desserts (a second trigger point) are consumed. As a result, even though the ankle may heal within two days, the ketone measurements do not recover by Day 3, which causes the software application to prompt for a second trigger point.

Exemplary Algorithm M4>(at least one good point−device precision). In addition to the inherent physiological fluctuation of the ketone measurements, the ketone measurement device has its own precision and variance. Consider the situation in which the device precision is 2 ppm. Based on the preceding rule, M4<M3 and this difference appears significant (5 ppm). However, M4 (5 ppm) is greater than one of the previously recognized "good" points (M1=6 ppm) minus the device precision (2 ppm). In this situation, the software application does not prompt the user to confirm that a trigger point occurred between Day 3 and Day 4. Exceptions might be if the previous "good" point was too far back in time or otherwise not applicable because of changes made to the user's weight management or fitness program.

The above algorithms may utilize baselines, such as those presented elsewhere in this disclosure (e.g., such as like the algorithms described with respect to FIGS. 18A-22). Instead of M4>M3, for example, M4>Baseline may be used. Additionally, as was described earlier, instead of subtraction, a ratio may be used. In the sensor literature, a signal to noise ratio (SNR) of 3 or more is desirable. In many clinical (or physiological) situations, however, an SNR of 2 is considered desirable, and sometimes even less.

Example 3

Comparing trigger points to ketone measurements may require use of compensation factors, such as those described in U.S. patent application Ser. No. 14/690,756, filed Apr. 20, 2015, which is hereby incorporated by reference in its entirety as if fully set forth herein. For example, it is generally known that a woman's body temperature is slightly higher during ovulation. In some instances, because of the increased temperature, there is increased kinetic/metabolic activity, which can cause an increase in ketone levels. If comparing two measurements (one the day before and one the day after ovulation begins), it may be necessary to adjust the post-ovulation measurement to account for the increase. In so doing, the data is normalized so that trigger points can be more readily recognized. Algorithms described in U.S. patent application Ser. No. 14/690,756, filed Apr. 20, 2015, which is hereby incorporated by reference in its entirety as if fully set forth herein, may be used for this purpose.

Example 4

The trigger point state aids in determining the likelihood that a trigger point occurred. There are instances in which overwhelming evidence that a trigger point state has been achieved overrides the otherwise driving algorithms. For example, if M5>M4 (which ordinarily does not trigger a prompt to a user requesting confirmation of a trigger point), if M5 occurred on a day when the user was at a salt water taffy shop and this user has a known problem with salt water taffy, the user may be prompted to confirm the trigger point. This type of approach is particularly useful in the following situations: (1) the user is traveling and forgot his or her ketone measurement device at home, but interpretation of the measurements when the user returns home is dependent on knowing if the user deviated during the trip; (2) there is a delayed decrease in the ketone measurement as a result of the trigger point. For example, if the user's heart rate is elevated 3-4 times during a 24-hour period, this might indicate high levels of stress due to a social or family situation, but the stress-impact to ketone measurements may not be noticeable until cortisol levels have changed some 48-72 hours later; and/or (3) the user has already experienced a significant trigger point and ketone measurements are low in general. In this type of situation, to aid in predicting the time period to recovery, counting the number of trigger points is useful. To exemplify this, a user's consumption of a high carbohydrate food (e.g., 1 bag of potato chips) may be enough to drop ketone levels to zero but recovery may occur within 2 days. However, if the user then consumes five times the volume (e.g., 5 other bags of potato chips), sufficient glycogen and/or glucose may be stored (from the multiple bags of chips) and the user will not return to a state of ketosis for a longer than normal period of time. Knowing the quantity of potato chips consumed is useful predictively for the ketone measurement system.

The algorithms for detecting the correlations between breath acetone levels and the occurrence of trigger points may be embodied in the mobile application run on the electronic device, in software executed by the remote system, and/or in software executed by the measurement device.

Once a pattern is determined, future breath acetone measurements can be analyzed (e.g., by the measurement device, by the mobile application running on the electronic device, etc.) to identify whether the pattern or a close match of the pattern (e.g., within a threshold value or percentage) has resulted as described in the examples above. Thus, the occurrence of a user-specific trigger point may be identified even without any explicit indication from the user or a third party that such a trigger point has occurred.

Preferably, the method comprises sending a message or alert to a caregiver or another third party via a network if a pre-specified alarm number of predictions occur. For example, the App may generate a notification to be transmitted to a caregiver or another third party if a certain number of trigger points are determined to have occurred within a set period of time.

A pre-specified alarm number may be set to mark the tolerance for user-specific trigger points to occur and cause unacceptable behavior. As an example, if a user has a challenge overeating popcorn when going to a movie theater, each time the user is at a movie theater and his or her breath acetone levels drop, a prediction may be generated suggesting that the user consumed popcorn. If the pre-specified alarm number is two times a month, two popcorn violations may cause the physician to be notified.

Alternatively, the method may comprise changing the treatment program if a pre-specified alarm number of predictions occur. This is important because if behavioral modification alone is not sufficient to control the user's actions, the treating physician may need to administer drugs, therapy, consider a different diet that is better suited for the user's physiology, or other intervention.

System for Managing Medical Conditions

In an embodiment, ketone sensors, such as the breath acetone measurement device 212, work in conjunction with sensors that measure other health parameters. As described elsewhere in this disclosure, ketones can be measured through the blood, breath, urine or skin. Other health parameters can be similarly measured in various ways, including through the blood, breath, urine or skin.

Certain individuals utilize a low carbohydrate diet (or a ketogenic diet) to manage diseases or chronic health conditions, such as diabetes, cancer, epilepsy and other conditions. In such situations, a ketone sensor, such as 212, can be used to monitor adherence to a low carbohydrate diet. If an individual adheres to the diet, certain symptoms are abated, thereby decreasing the need for medication, frequency of acute episodes, or other forms of treatment. However, the consequences of non-adherence are similarly significant. For example, a diabetic who fails to adhere to a low carbohydrate diet and is not taking insulin can suffer the effects of uncontrolled diabetes. In such scenarios, it is desirable for ketone measurements to be considered in the context of other health parameters so as to provide guidance and feedback to the patient or his/her physician on the suitability of the diet as a form of treatment.

A combination approach is use of a low-carbohydrate diet and insulin program, where the user attempts to adhere to a low-cab diet as much as possible, but is given insulin on an as-needed basis during occasional periods of non-compliance. In such a situation, the ketone sensor system, in one embodiment, interacts with and controls an insulin pump such that insulin is delivered only when the current ketone level or pattern indicates a need for it.

Figure 30:
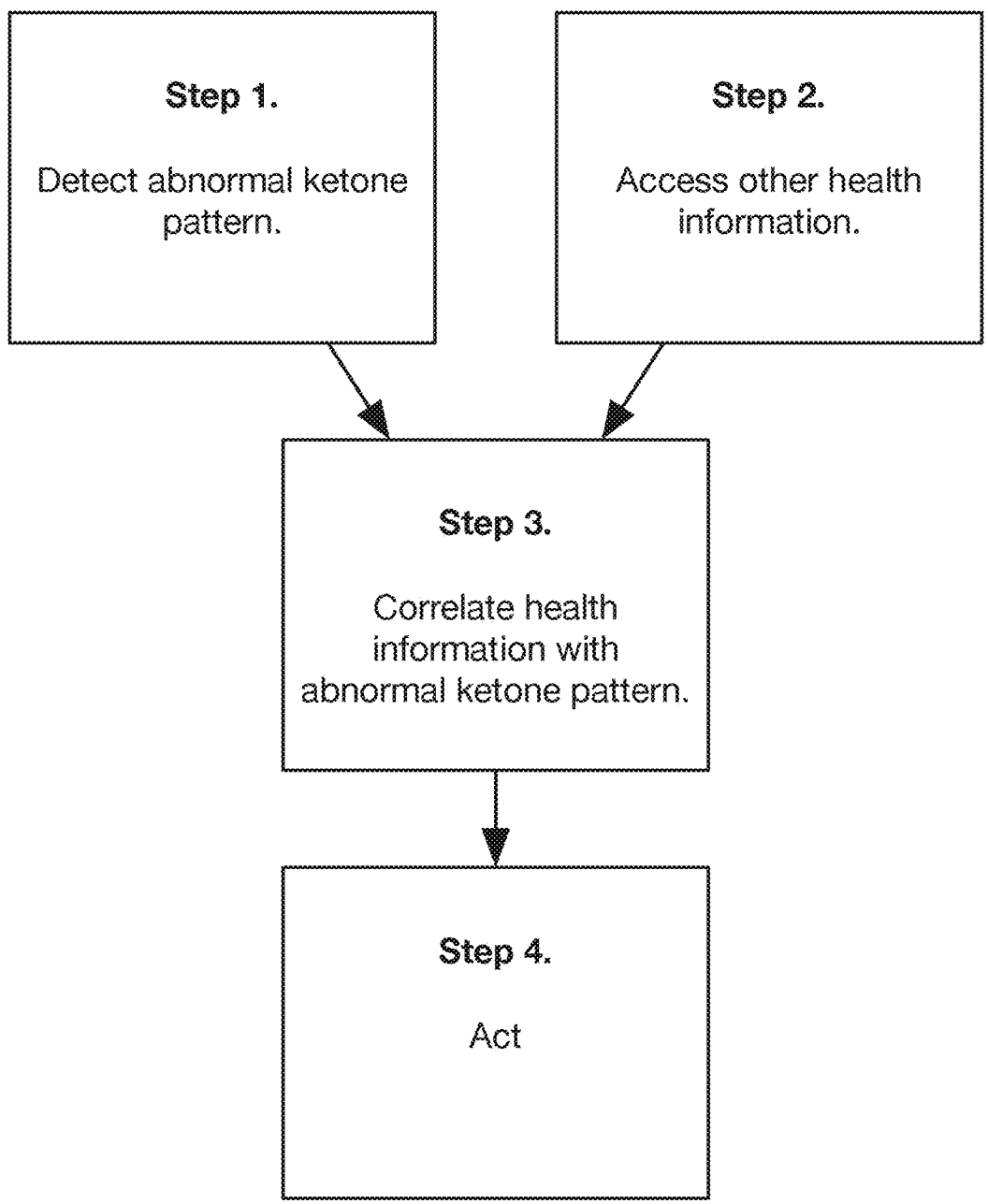
FIG. 30 is a flow chart or diagram that illustrates process flows and displays for a software application involving a ketone pattern and non-ketone health parameters.

An exemplary approach to address this problem is described next. These steps will be described serially, as depicted in FIG. 30, but other orders of the steps apply as well, such as those shown in FIG. 31. As will be apparent (and as described below), the process shown in FIGS. 30 and 31 can be performed by any one or more devices (under control of software executed by the processors of such devices), such as a portable ketone measurement device (ketone sensor) 212, a mobile computing device (such as a smartphone) 130, 230, 2710 of the user, a remote computer system or server 40, 140, 240, a measurement device (such as a glucose measurement device) that measures a physiologic parameter other than ketone levels, or any combination of the forgoing. Some of the steps of the process may be performed by different devices than others.

Figure 31:
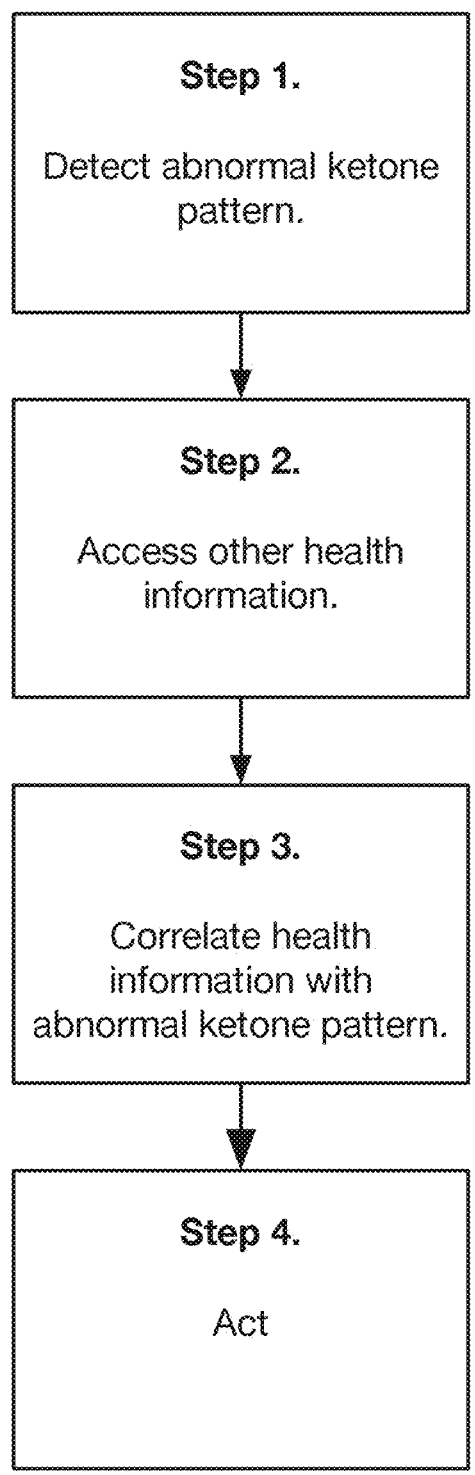
FIG. 31 is another flow chart or diagram that illustrates process flows and displays for a software application involving a ketone pattern and non-ketone health parameters.

First, in Step 1 of FIGS. 30 and 31, the process detects an "abnormal" pattern of ketone readings. In certain embodiments, the processor that performs this step is within the ketone sensor 212, in other situations within the user's mobile device 130, 230, 2710, and in other situations within a remote server/system 40, 140, 240. Combinations may also be used. The abnormal pattern is primarily intended to provide an indication that the patient is not able to sustain elevated ketone levels. Various algorithms can be used to detect an abnormal pattern of ketones. Certain algorithms make use of an alarm threshold. An alarm threshold can be determined in various ways, including input by a healthcare professional or other authority figure, input by the user, learned by the processor or remote system based on data analysis of past ketone levels, or learned by the processor or remote system based on data analysis of past ketone levels and other health parameters. Certain algorithms may make use of configuration parameters to customize the pattern recognition process on a case by cases basis. These parameters may be input by a healthcare professional or other authority figure, input by the user, learned by the processor or remote system based on data analysis of past ketone levels, or learned by the processor or remote system based on data analysis of past ketone levels and other health parameters.

A first algorithm includes detection of ketone levels dropping below the alarm threshold. A second algorithm includes detection of ketone levels dropping below an alarm threshold a certain number of times within a specified time period. A third algorithm includes detection of a pattern in which multiple previous ketone levels resemble a dip (i.e., ketone levels suddenly drop significantly but then quickly rise back to normal levels). The number of ketone levels considered by this third algorithm is a configuration parameter that is learned dynamically by the system by analyzing ketone levels of not only the patient but many other patients as well. Various other algorithms can be used and are described, for example, in conjunction with Trigger Points in this disclosure. The primary output of the algorithm is an indication of whether an abnormal pattern of ketone measurements is detected. This determination may be made, for example, whenever a new ketone measurement is generated.

Second, in Step 2 of FIGS. 30 and 31, the process obtains other health parameters. This Step 2 may be performed in response to the detection of the abnormal pattern in Step 1. The term "health parameter" is used broadly and it includes any parameters useful in confirming the presence, absence or extent of a disease or health condition. Examples of health parameters are: hemoglobin A1c, insulin and glucose levels. Another health parameter is breath glucose levels, which can be determined directly or indirectly using other parameters. The health parameters could be indicators of disease progression or stage. Or, they could indicate the user's "emotional" state or activity level. In the latter instance, how the patient "feels" or the patient's energy level could be important to determine the disease severity. An example of such data would be a patient report of pain level if a patient is using a low carbohydrate diet to manage an inflammatory disease, such as arthritis. Another example of such data would be analyzing a patient's personal data such as social network updates, calendar appointments, email, Web browsing history etc. Another example of such data would be asking one or more trusted individuals that are part of the patient's social network to estimate the patient's emotional state.

Figure 33:
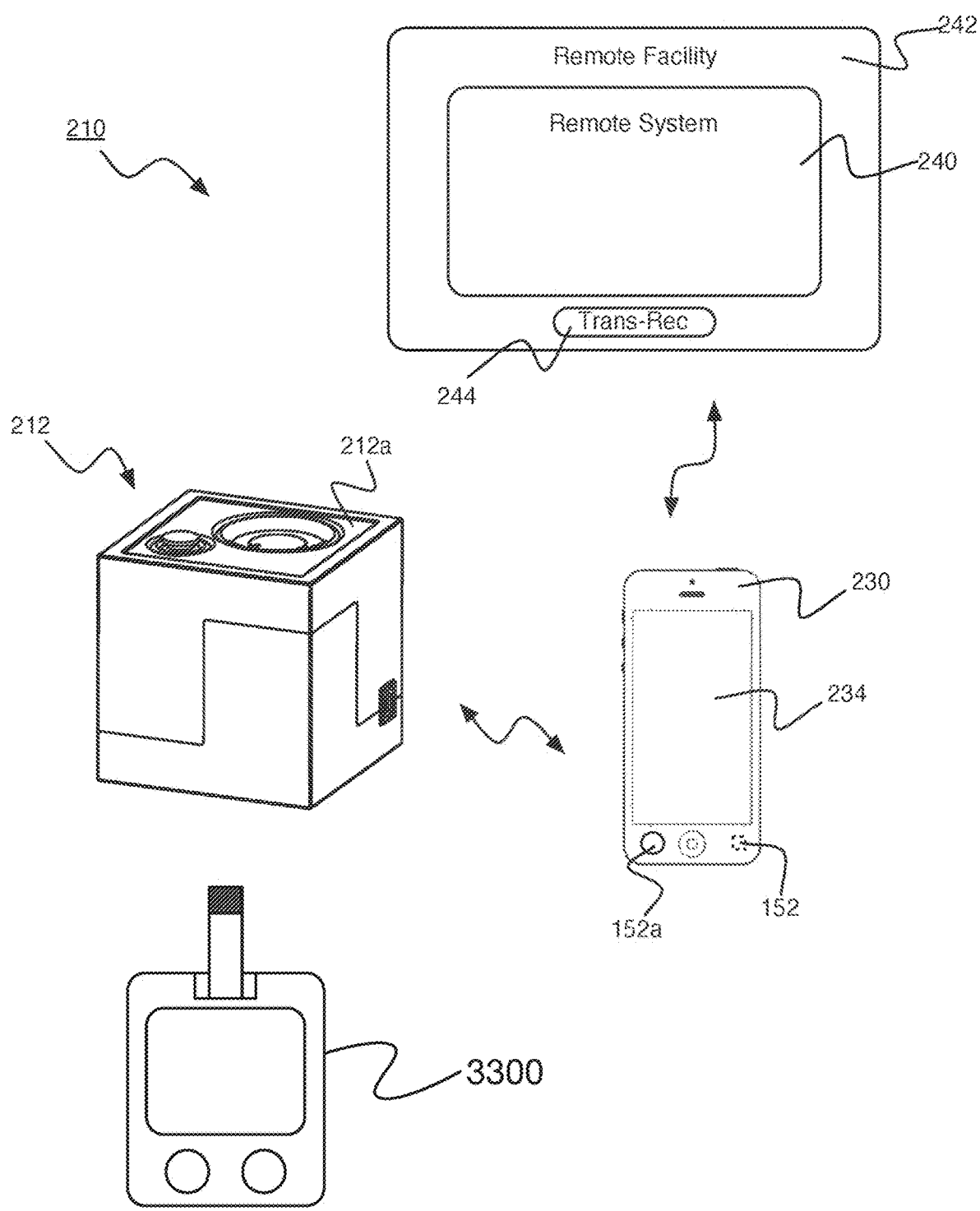
FIG. 33 shows an embodiment of a ketone sensor that works in conjunction with a glucose sensor.

The process can obtain this health information by prompting the user for input, by accessing databases containing health information (e.g., from Apple's Health Kit), and/or by issuing commands to other devices, such as an implantable glucose sensor or an iWatch, to perform a measurement. FIG. 33 depicts a system wherein the ketone sensor 212 is coupled to a mobile device 230. The mobile device prompts the user to perform a glucose reading on the glucose sensor 3300. The processor on the mobile device 230 is configured to compare the ketone levels with the glucose levels.

Figure 32A:
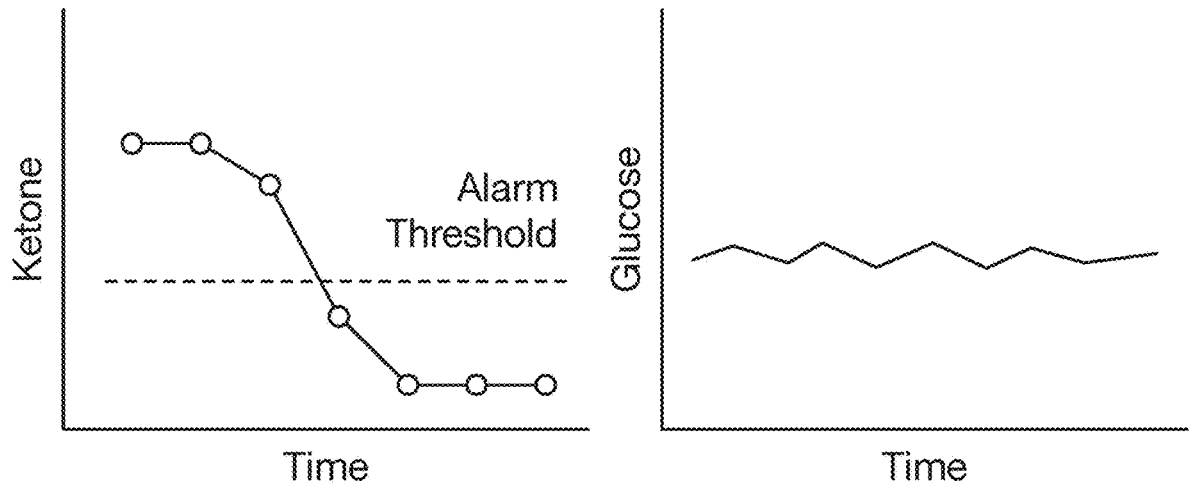
FIG. 32A-32B show graphical charts of the output of a ketone sensor and a sensor of a second health parameter, here glucose.
Figure 32B:
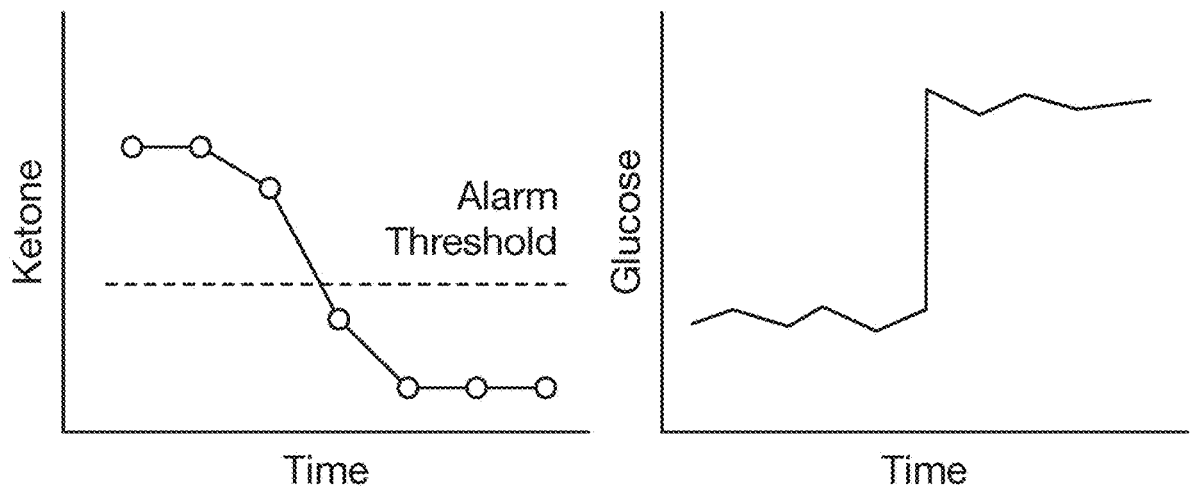

Third, in Step 3 of FIGS. 30 and 31, the abnormal ketone pattern is correlated and compared with the health parameter data. An exemplary comparison is shown in FIG. 32. In FIG. 32A, the ketone levels drop below an alarm threshold. However, the glucose levels, which are an indication of the level of control of diabetes, remain relatively constant. In contrast, in FIG. 32B, the ketone levels drop below an alarm threshold. Around the same time, the glucose levels spike. Here, the glucose levels (the health parameter) provide additional context to determine if the abnormal ketone pattern is problematic. In some embodiments, this process responds to this problematic combination by performing a corrective action (as described below), such as outputting a message to the user, sending a message to a clinician, activating an insulin pump, and/or activating another type of therapeutic device.

Other considerations for the correlation include: is the health parameter significantly different than normal levels? Is the health parameter significantly different than normal levels or patterns observed in the general population or a subset of the general population that matches one or more demographic characteristic of the user (e.g., age, sex, height, weight, race)? How frequently has the abnormal ketone pattern been observed? Are there other ketone levels that did not meet an "alarm threshold" but were close? How frequently did those close calls occur? The process of FIGS. 30 and 31 may take these and other factors into consideration.

Fourth, in Step 4 of FIGS. 30 and 31, the system is configured to act if the correlation suggests that the abnormal ketone pattern is problematic, in view of the acquired health parameter data. Examples of actions that the process can take include: (a) notifying the user via an email, instant message, popup message on their device, etc., (b) changing a display of all associated ketone levels post-determination to contain a certain flag or warning viewable on the user interface, (c) preventing further measurements on the ketone sensor 212, (d) sending a notification to a physician, parent or other authority figure, and (e) enabling or disabling certain peripheral devices. For example, in the case of an epileptic, the process may disable the ability to turn on the ignition of a car (so as to reduce the chances of a seizure while driving). In the case of a diabetic, the process may disable opening a refrigerator with an automated lock (so as to reduce the changes of consuming problematic foods). Another example would be to turn on an auditory signal or LED on related measurement devices, such as a glucose monitor, to encourage the patient to perform a test.

As will be apparent, some or all of the steps of the process of FIGS. 30 and 31 can be performed by the ketone sensor 212. The following is an example. The system takes readings from the ketone sensor 212 which is coupled to a mobile device 230. The ketone sensor 212 is used by the patient and the sensor 212 tracks the measurements over time. The ketone sensor 212 is configured to compare the ketone levels. Upon detecting an abnormality in ketone levels such as a drop in ketone level, the sensor can: 1) flag all measurements, and/or 2) place an indicator over measurements to identify the severity of the deviation. The ketone sensor 212 can also prompt the user to perform a glucose reading on the glucose sensor 3300, or a connected mobile device receiving information from the sensor 212 could prompt the user to perform a glucose reading on the glucose sensor 3300. Additionally, the mobile device 230 can be configured to 1) notify a physician of the readings, 2) prompt a glucose monitor or other parameter sensor to take a measurement (e.g., via a wearable sensor), 3) prompt the user via an app to measure fasting glucose at 6 AM (an alarm for 6 AM could be set on the phone by the app or to any connected device like an alarm clock via an internet or Bluetooth connection, or 4) place an order with a pharmacy to obtain more glucose strips.

As an example, the ketone sensor 212 could determine that a user is sustaining ketone levels at 5 ppm to 10 ppm. Two months later, however, the ketone sensor 212 measures a level that is below 2 ppm. The sensor relays that information to the mobile device 230. The mobile device prompts the user to check the glucose value. In its history of glucose measurements, the mobile device knows that the previous reading taken a month ago was 80. A new measurement determines that the glucose level is now 130. The mobile device can prompt the user to take measurements over the next three days. For example, the mobile device receives readings between 120 and 130 over three days. Additional measurements can be taken to make sure the readings are consistent and accurate. Based upon these readings, the mobile device can perform any one of the actions previously mentioned.

As will be apparent, all of the measurement analysis tasks described herein as performed by the mobile device 230 (or the App which it runs) can alternatively be performed by the remote system 40, 140. Such tasks include, for example, the detection of the abnormal ketone pattern in Step 1 of FIGS. 30 and 31, and the analysis of other physiologic parameter data as shown in FIG. 33. For example, the mobile device/application may acquire a sequence of measurements from the ketone sensor or other measurement device, and transmit these measurements to the remote system 40, 140 for analysis. In some embodiments, the mobile device and application may be omitted, in which case the ketone sensor 212 may communicate directly with the remote system 40, 140.

In one specific embodiment, the process of FIGS. 30 and 31 is embodied in the executable program code of the mobile application installed on the user's smartphone or other mobile computing device, and is used to trigger a check of the user's glucose level. In this embodiment, when the mobile application obtains a new ketone measurement, is determines whether an abnormal pattern is present in the most recent N ketone measurements, where N is integer such as 3, 4, 5, 6, 7, or 8. The process may alternatively search for an abnormal pattern within a bounded ranged of the most recent ketone measurements. The mobile application may make this determination by analyzing the ketone measurements, or by sending the ketone measurements to the remote system 40, 140 for analysis. If the analysis reveals that the pattern is abnormal (or that a particular type of abnormality exists), the mobile application either prompts the user to generate a glucose measurement, or instructs a glucose measurement device to take the measurement. (The mobile application may already have a record of past glucose measurements received from the glucose measurement device.) The mobile application then determines (possibly through interactions with the remote system) whether the glucose reading, or a sequence of most recent glucose readings, is abnormal. For example, the mobile application may determine whether a sequence of glucose measurements follows an abnormal pattern corresponding to the abnormal pattern of ketone measurements. Depending on the outcome of this determination, the mobile application may then perform a corrective action, such as displaying or sending a notification or activating an insulin pump, as described above.

Using Non-Ketone Biometric Data with Rule Compliance Detection, Acetone Tags, and Trigger Points In some embodiments, the system (e.g., the measurement device, the electronic device, the remote system, or another diagnostic or measurement device not shown in FIGS. 1-3) may be capable of monitoring the heart rate and/or other non-ketone biometric parameters of the user. For example, in embodiments that use a mobile application running on a smartphone, the smartphone may communicate by Bluetooth, Wi-Fi, or another wireless standard with a user-worn heart rate monitoring device such as a wristband or watch. Through this wireless connection, the mobile application may monitor the user's heart rate in real time, or may retrieve heart rate statistics or history data. As another example, the mobile application may run on a smart watch or other user-worn device that is capable of directly monitoring the user's heart rate, and the smartphone may be omitted.

In these embodiments, some or all of the above-described features involving rules, acetone tags, and trigger points may be varied to make use of the additional biometric data. As one example, a rule may require that a user engage in a certain level of aerobic exercise within a prescribed time frame before taking an acetone measurement. To evaluate compliance with this rule, the mobile application (or another system component) may determine whether the user's heart rate reached a certain threshold level during the relevant time frame preceding the acetone measurement. As another example, the system may use the monitored heart rate to generate rule-based reminders; for instance, where a rule requires aerobic activity within a prescribed time period before an acetone measurement, the mobile application may generate a measurement reminder upon detecting that the user's heart rate has reached a target exercise level and has then dropped to a non-exercise level. As yet another example, the system may automatically record, in association with a specific acetone level measurement, one or more heart rate statistics, such as the user's average and peak heart rates over a particular time period, such as the last 2 hours. As yet another example, a rule may require that the user take the ketone measurement as soon as the user wakes up. The mobile application may receive information from a pedometer (or an application running on the electronic device that functions as a pedometer using sensors present in the electronic device) that indicates a number of steps that the user has walked in the current day. If the number of steps is low (e.g., less than 10 steps), then the mobile application may automatically determine that the user has complied with the rule.

As another example, an acetone tag applicable to a user may be whether the user has engaged in exercise during a time immediately preceding the ketone measurement (e.g., button 510 in FIG. 13 discussed above). The mobile application may automatically select the acetone tag for the next ketone measurement if the user's heart rate exceeded a minimum level in the time immediately preceding the ketone measurement (e.g., the minimum level was exceeded within a 2 hour period before the ketone measurement), which may indicate that the user was exercising. Likewise, another acetone tag applicable to a user may be whether or not the user has been in a high stress condition prior to the ketone test (e.g., button 512 in FIG. 13 discussed above). The mobile application may automatically select the acetone tag for the next ketone measurement if the user's heart rate exceeded a minimum level in the time immediately preceding the ketone measurement (e.g., the minimum level was exceeded within a 2 hour period before the ketone measurement), which may indicate that the user was experiencing a high level of stress.

As another example, a trigger point applicable to a user may be "drinking coffee." In some cases, the user's heart rate may rise to a target heart rate level when the user drinks coffee. Thus, the mobile application may automatically generate a prompt to ask the user whether the user drank coffee prior to the ketone measurement test if the heart rate meets or exceeds the target heart rate level.

Communications

Before any communications described herein are sent between the breath analysis device and the electronic or user device (e.g., smartphone), the electronic device may pair with the breath analysis device using techniques described in U.S. Provisional Patent Application No. 62/161,872, filed May 14, 2015, which is hereby incorporated by reference in its entirety as if fully set forth herein.

Either the communication device (e.g., electronic device) or the breath analysis device may retain a local copy of the transmitted data such that the data resides both on the remote system as well as the communication device and/or the breath analysis device.

The system between the breath analysis device and the remote system may also facilitate a "mandatory uplink" feature. The mandatory uplink feature may cause the breath analysis device to transmit data (e.g., readings) to the electronic device, and the electronic device may automatically transmit the data to the remote system, without any user interaction upon receipt of the data from the breath analysis device. This feature may also involve withholding output or display of the measurement signal (e.g., the readings) until the signal has been transmitted to and/or received by the remote system. The mandatory uplink feature desirably prevents users from selectively reporting or withholding certain test results. For example, in the context of a weight loss program in which reported results are reviewed by a coach, some users may wish to report only the "good" test results.

In some embodiments, the mandatory uplink feature includes a selective transmission of data based on one or more factors. For example, conditions may be placed on a location in which the user is allowed to take readings. Thus, the electronic device may use a GPS location to determine whether to forward received data to the remote system. As another example, conditions may be placed on a time in which the user is allowed to take readings. Thus, the electronic device may use a time (e.g., wall clock time) to determine whether to forward received data to the remote system. As another example, conditions may be placed on the type of physiological state the user must be in when the readings are taken. Thus, the electronic device may use the physiological state of the user (e.g., heart rate, whether the user is asleep or awake, etc.) to determine whether to forward the received data to the remote system. Alternatively, the electronic device may forward the data regardless of location, time, and/or physiological state of the user, but may use the GPS location, time, and/or physiological state of the user to determine whether to mark the data as normal or aberrant.

The breath analysis device and/or the electronic device may further cache data before the data is forwarded to the remote system. For example, the breath analysis device and the electronic device may lose a connection with each other (e.g., because the electronic device is moved out of transmission range of the breath analysis device). The breath analysis device may then cache the data at least until connectivity with the electronic device is restored and the cached test results transferred. As another example, the electronic device may receive data from the breath analysis device, but may not be in networked communication with the remote system. Thus, the electronic device may cache the received data at least until the electronic device can communicate with and transmit the data to the remote system.

This mandatory uplink feature can be advantageous for several reasons. As an example, the remote system may be consulted to improve the measurement process (e.g., use different parameters given a user's response). In such a case, the remote system processes the measurement signal, generates a response signal in response to the measurement signal, and transmits the response signal to the breath analysis device. This response signal can be useful to control or modify an operating parameter for instrumentation within the breath analysis device, such as pumps, linear actuators, or sensors. As a further example, mandatory uplink can be useful to ensure that parameter data is stored and made available to facilitate broader population data. "Population Data" is used broadly to mean qualitative or quantitative information pertaining to the aspect of the relevant analyte or measurement that is being reported, where the information has been collected from a plurality of individuals. Such information is often useful to establish population reference ranges, trends or changes, or predictions. It may be desirable for the plurality of individuals to represent a statistically significant sample, for example of a particular ethnicity, sex, health status, or other stratifying characteristic.

Population data aids in establishing parameters such as normal variability, ranges of acceptable and pathological values, and trends, and the like. As yet another example, mandatory uplink can be useful to check the user's measurement signal against historical signals to assess whether the user's measurement signal appears accurate or whether a measurement may have occurred. This would result in a user prompt for additional information regarding, for instance, the user's state.

In view of the foregoing, there are various new methods for displaying ketone measurement data that facilitate the principles and innovations set forth herein. For example, the ketone measurement data may be manipulated to form statistical results and the statistical results may be displayed. Examples of such statistical results are provided in FIGS. 18A-22. The manipulated ketone measurement data illustrated in FIGS. 18A-22 may be generated by the electronic device 130 and displayed within a user interface. The manipulated ketone measurement data illustrated in FIGS. 18A-22 may alternatively or in addition be displayed in a content page generated by the remote system 140. A user may access the data by visiting the content page using, for example, a browser running on the electronic device 130.

FIGS. 18A-E present breath acetone measurement results data for five established dieters over a 50-day weight loss program. At the bottom of the charts illustrated in FIGS. 18A-E, various formulas are shown that can be used to display the data in different formats.

Figure 18A:
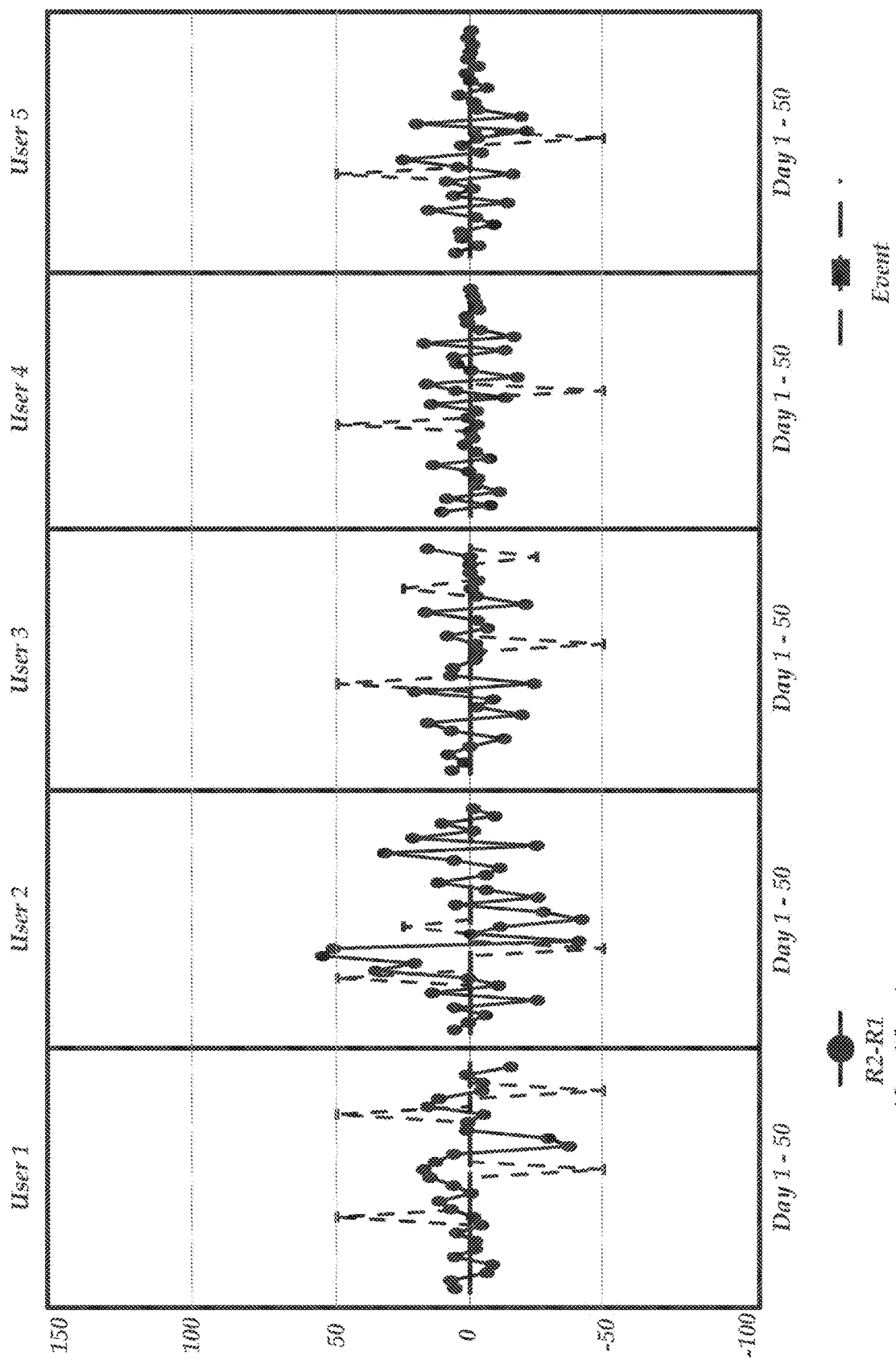
FIGS. 18A-E show graphical charts utilizing various algorithms to represent breath acetone levels and various event tags according to the implementation that is the subject of FIG. 17.

For example, as illustrated in FIG. 18A, Algorithm 1 may include a breath acetone level measured on a first day (e.g., a day before the current day) subtracted from the breath acetone level measured on a second day (e.g., the current day). In Algorithm 1, R2 may represent the breath acetone level measured on a current day and R1 may represent a breath acetone level measured on the day before the current day.

Figure 18B:
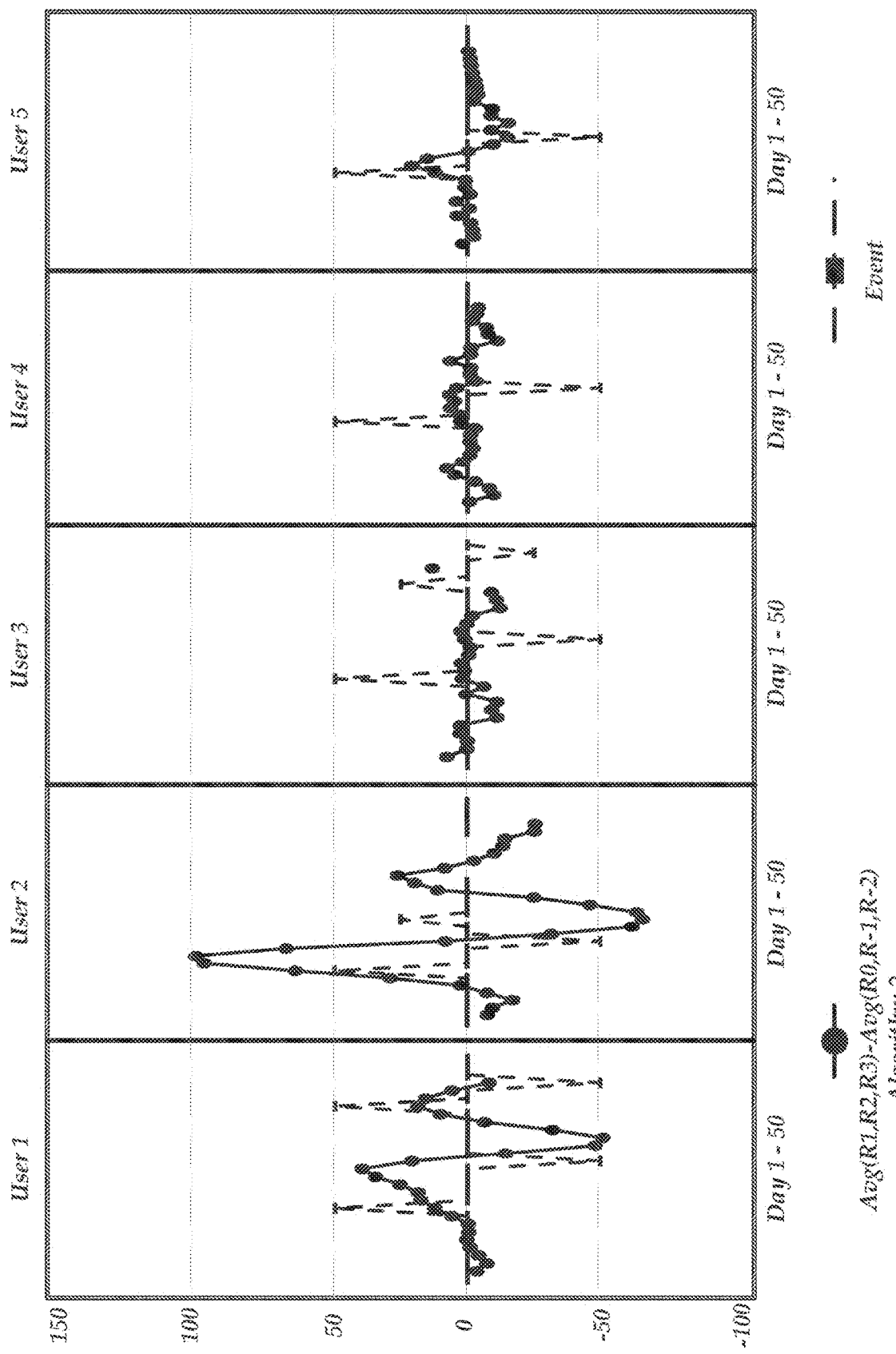

As another example, as illustrated in FIG. 18B, Algorithm 2 may include a multi-day running average (e.g., a 3-day running average) of breath acetone levels subtracted from another multi-day running average (e.g., another 3-day running average) of breath acetone levels. In Algorithm 2, Avg(R1, R2, R3) may refer to a 3-day running average of breath acetone levels for a day after the current day (e.g., R1), two days after the current day (e.g., R2), and three days after the current day (e.g., R3). Avg(R0, R−1, R−2) may refer to a 3-day running average of breath acetone levels for a day after a current day (e.g., R0), a day before the current day (e.g., R−1), and two days before the current day (e.g., R−2). A multi-day running average may be useful in smoothing varying breath acetone measurements to provide the user with more meaningful results. For example, a user may exercise every other day, thereby resulting in large variations in the breath acetone levels day by day. Because of the large variations, displaying the raw breath acetone measurements may not provide a clear indication of whether the user is positively progressing to a desired goal. A running average, on the other hand, may provide a clearer indication of whether the user is positively progressing to the desired goal.

Figure 18C:
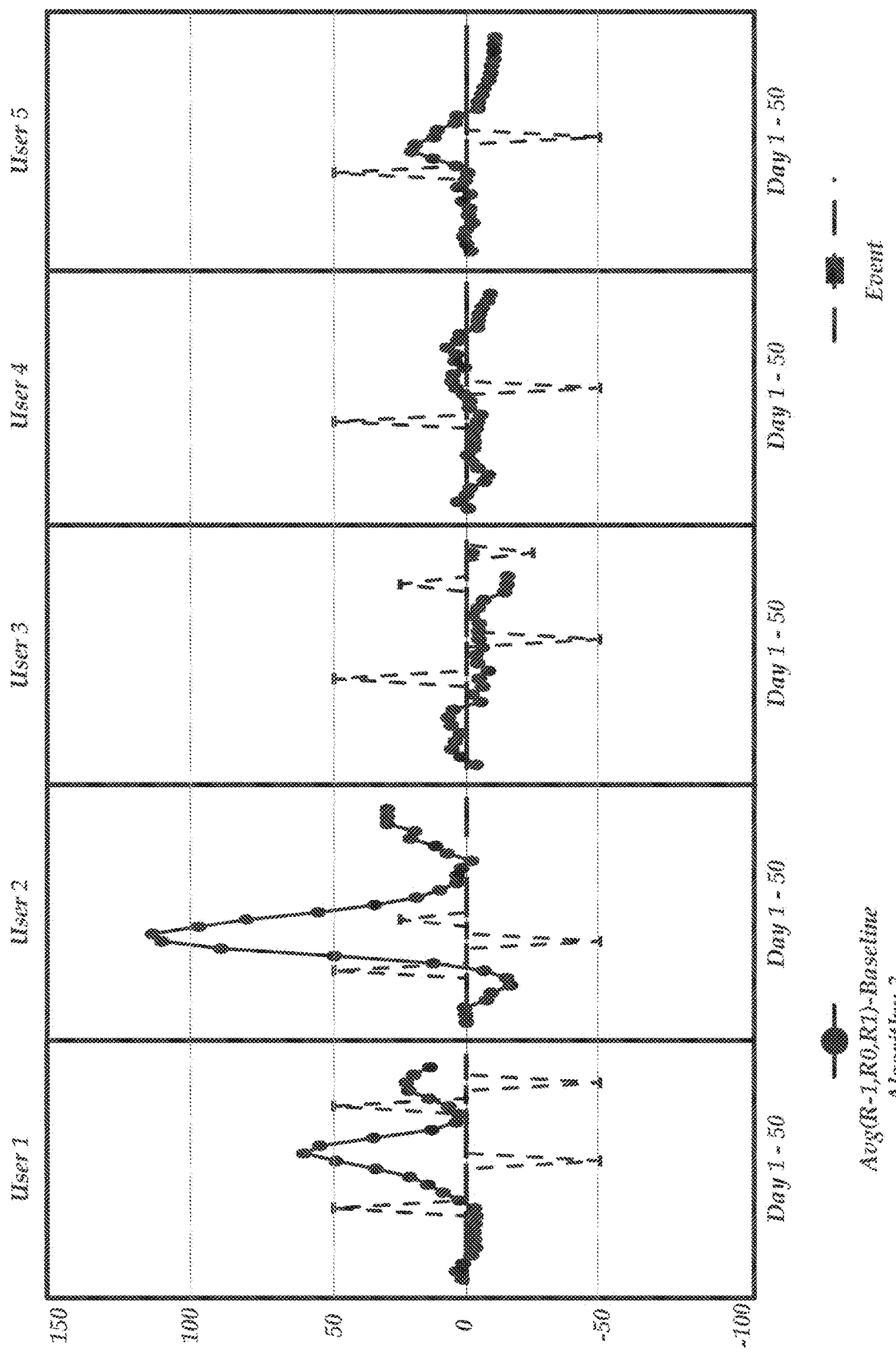

As another example, as illustrated in FIG. 18C, Algorithm 3 may include a baseline breath acetone level subtracted from a multi-day running average (e.g., a 3-day running average) of breath acetone levels. In Algorithm 3, Avg(R−1, R0, R1) may refer to a 3-day running average of breath acetone levels for a day before the current day (e.g., R−1), a current day (e.g., R0), and a day after the current day (e.g., R1).

Figure 18D:
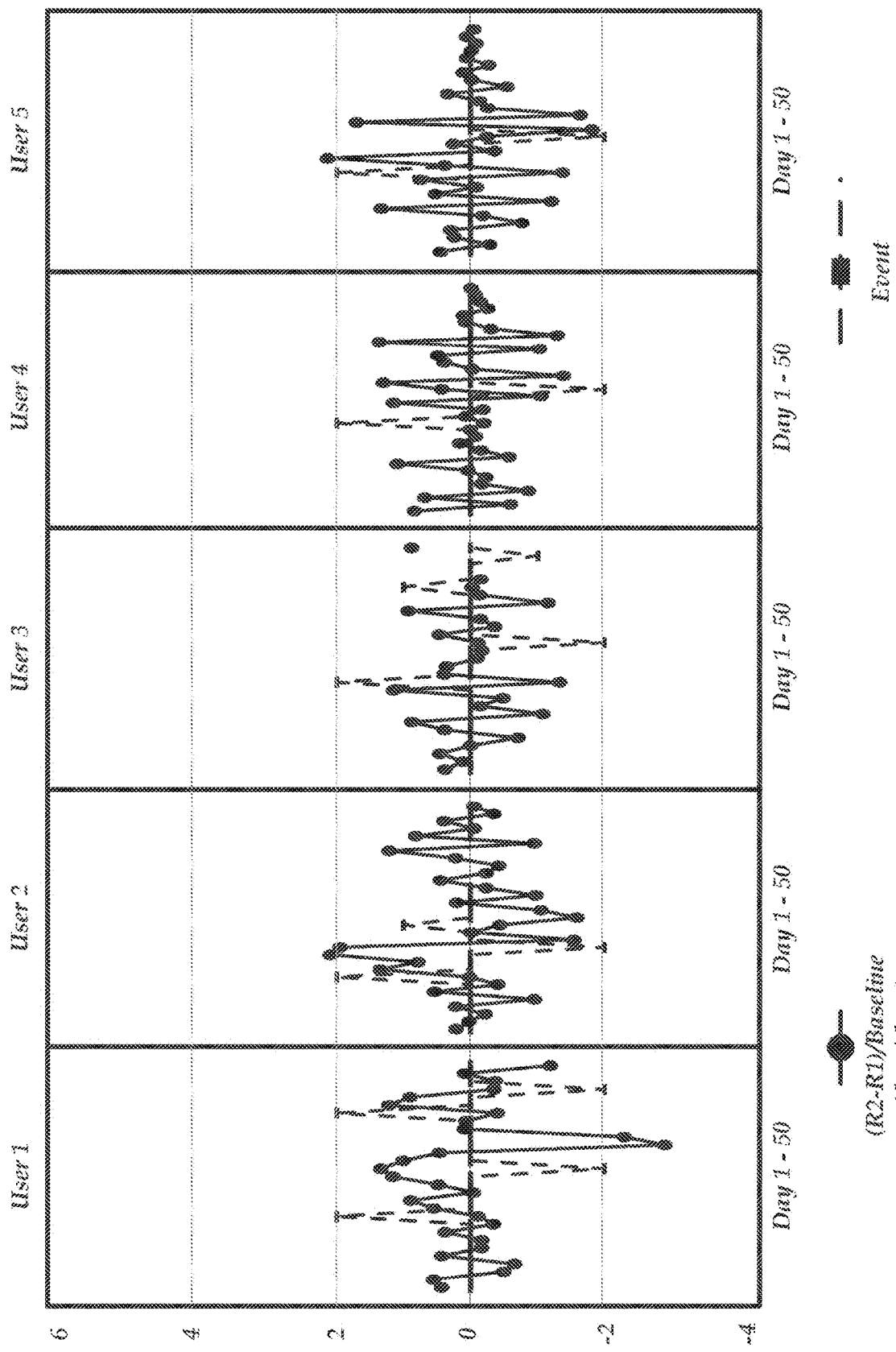

As another example, as illustrated in FIG. 18D, Algorithm 4 may include a breath acetone level measured on a first day (e.g., a day before the current day) subtracted from the breath acetone level measured on a second day (e.g., the current day), with that difference divided by the baseline breath acetone level. In Algorithm 4, R2 may represent the breath acetone level measured on a current day and R1 may represent a breath acetone level measured on the day before the current day.

Figure 18E:
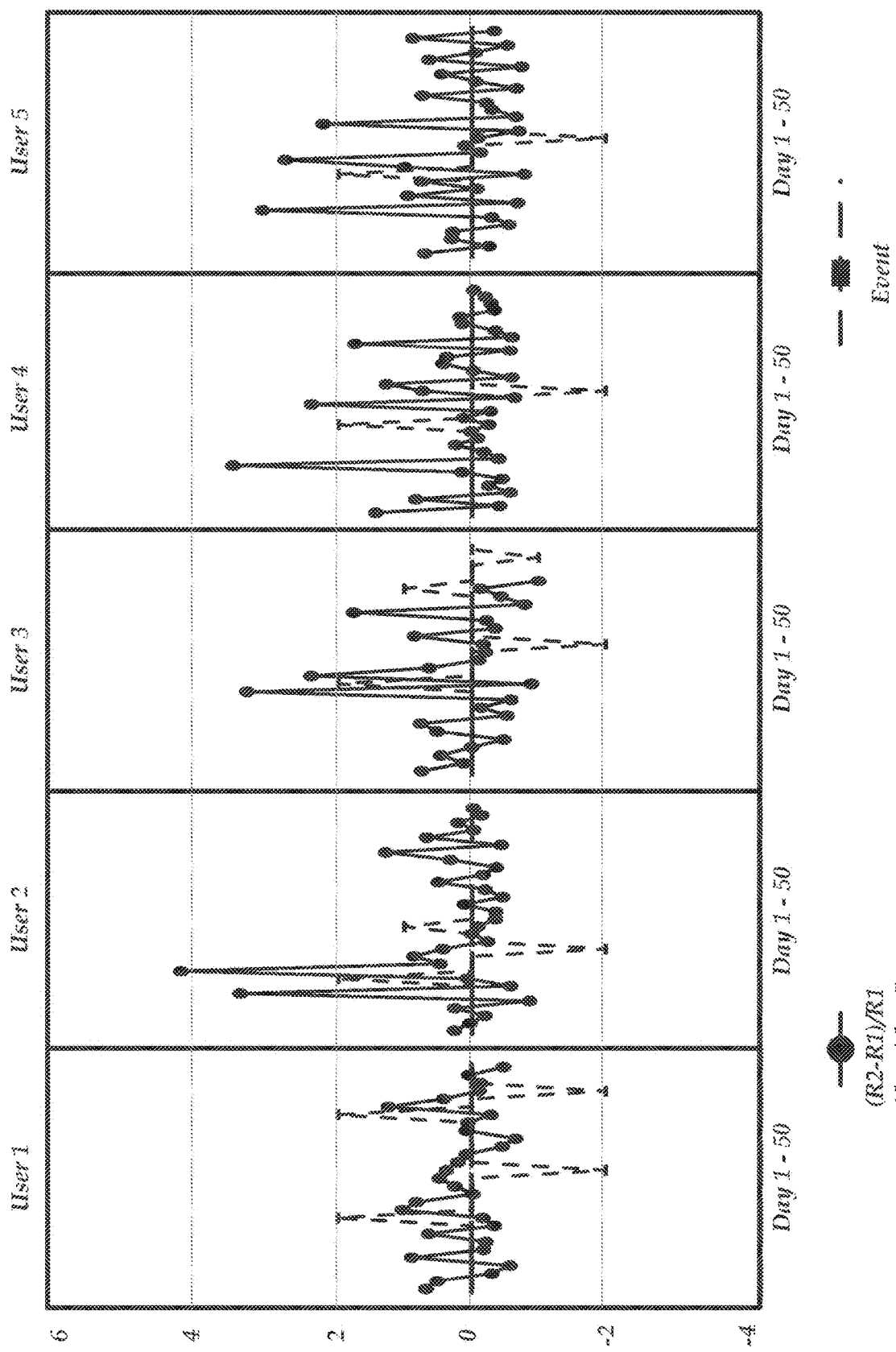

As another example, as illustrated in FIG. 18E, Algorithm 5 may include a breath acetone level measured on a first day (e.g., a day before the current day) subtracted from the breath acetone level measured on a second day (e.g., the current day), with that difference divided by the breath acetone level measured on the first day. In Algorithm 5, R2 may represent the breath acetone level measured on a current day and R1 may represent a breath acetone level measured on the day before the current day.

Figure 19:
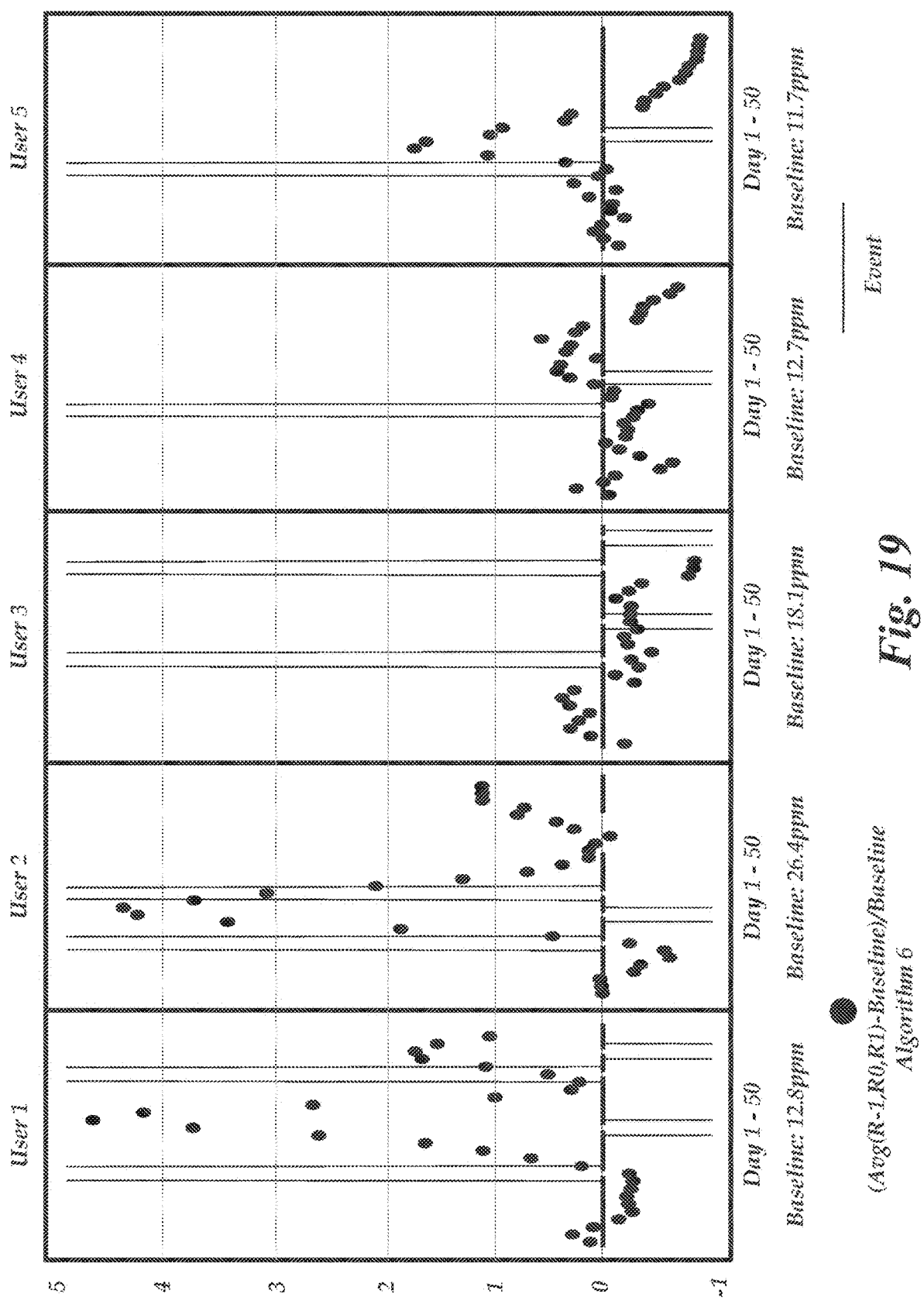
FIG. 19 shows a graphical chart that uses a given algorithm to re-present raw breath acetone levels for enhanced reporting to a healthcare provider according to preferred implementations of the present disclosure.

As another example, another algorithm illustrated in FIG. 19 (e.g., referred to herein as Algorithm 6) may include a baseline breath acetone level subtracted from a multi-day running average (e.g., a 3-day running average) of breath acetone levels, with that difference divided by the baseline breath acetone level. In the algorithm, Avg(R−1, R0, R1) may refer to a 3-day running average of breath acetone levels for a day before the current day (e.g., R−1), a current day (e.g., R0), and a day after the current day (e.g., R1).

Optionally, the raw baseline may be displayed along with plotted acetone levels. The raw baseline and/or the plotted acetone levels (e.g., the raw acetone measurements and/or the data resulting from implementation of one or more of the above described algorithms) may be transmitted to an external device, such as a device operated by a physician or similar third party support person, via the App.

In some embodiments, the measurement device 112 and/or the electronic device 130 (e.g., via the App) selects one or more of the algorithms and displays data based on the selected algorithm(s). For example, each of the above-described algorithms, when plotted, may provide useful information for only a subset of users. Data plotted based on Algorithm 1 for a first user may provide useful information to the first user and/or a third party, but data plotted based on Algorithm 2 for the first user may not provide useful information to the first user and/or the third party. Thus, the measurement device 112 or the electronic device 130 (e.g., via the App) may select and plot data corresponding to algorithms that may provide useful information to the respective user.

The App may select an algorithm based on the occurrence of user-reported events and/or based on characteristics of the user. For example, the App may generate a different graph based on one or more of the algorithms and the raw breath acetone measurements. If the user indicates that an event occurred, the App may analyze the values in each graph around a time that the event occurred. The App may select the algorithms for which there is a change in values before and after the time that the event occurred that is greater than a threshold value. As another example, the App may receive and store characteristics of the user. Such characteristics may include biographical information, how often the user exercises, the intensity of such exercise, and/or the like. Combinations of these characteristics may be correlated with a specific algorithm or specific algorithms. Based on the combination of characteristics stored for a particular user, the App may select one or more algorithms and generate a different graph based on the selected algorithms for display in the App.

FIG. 19 shows a response of five established dieters to a temporary change in the diet program that is known to cause increased ketone levels. For example, the baseline breath ketone level for each of the five users may be 12.8 ppm, 26.4 ppm, 18.1 ppm, 12.7 ppm, and 11.7 ppm, respectively. Because each user has different baseline breath ketone levels, the App may normalize the ketone levels such that differences between measured ketone levels and the baseline can be visualized. For example, the App may use Algorithm 6 to normalize the ketone levels. As illustrated in FIG. 19, users 1, 2, and 5 showed clinically positive responses to the temporary diet change, which is reflected in normalized ketone levels that are above 0. Users 3 and 4 did not report success with the change in the diet program, which is reflected in their low normalized levels of ketones (e.g., normalized ketone levels around 0).

Figure 20:
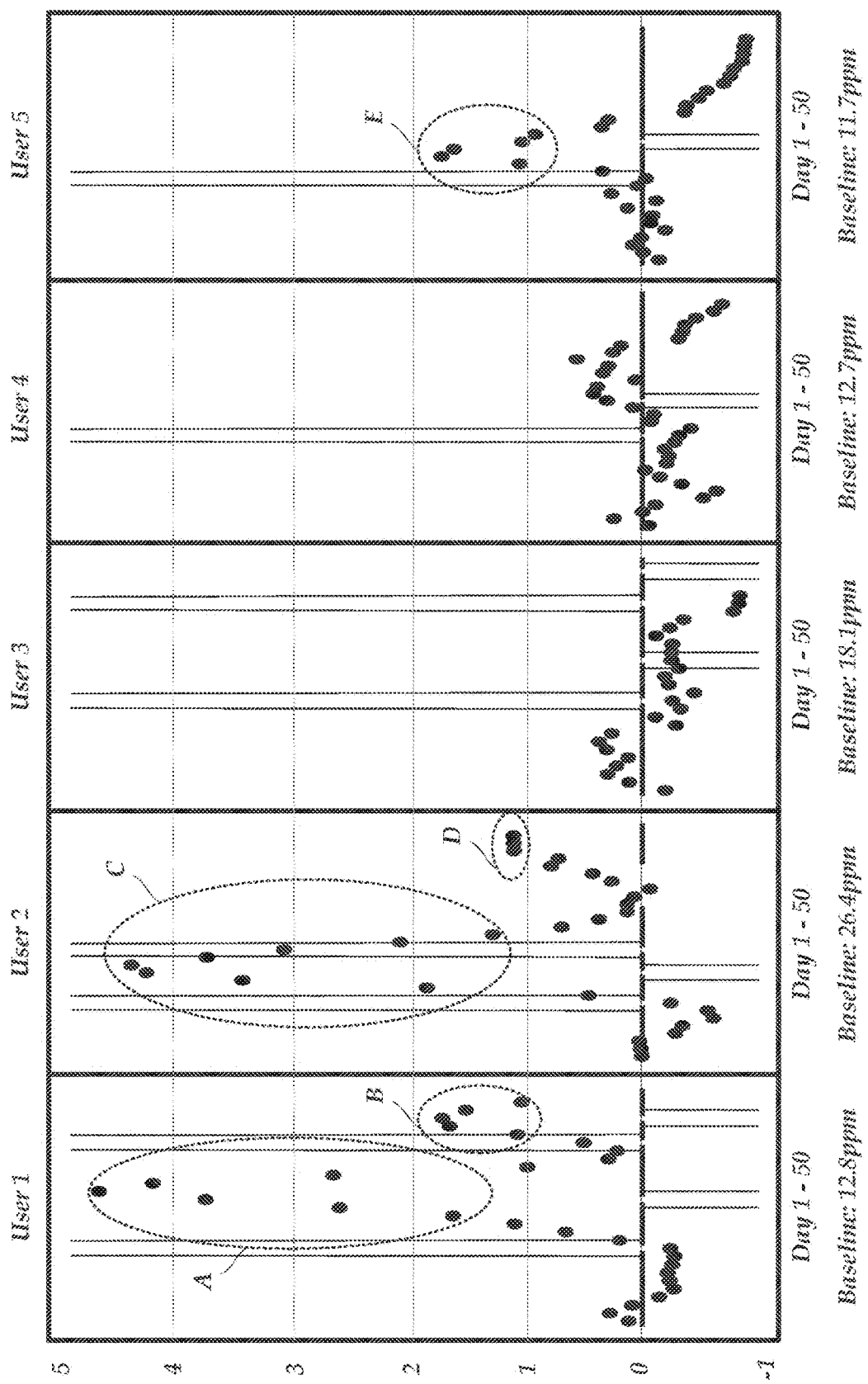
FIG. 20 depicts the data of FIG. 19 with certain features highlighted.

FIG. 20 shows the same data as is presented in FIG. 19, but highlights significant variations in the data. For example, the App may highlight normalized ketone levels that are a threshold value (e.g., a specific value, a standard deviation, two standard deviations, etc.) greater than a set value (e.g., a median or mean normalized ketone level, 0, etc.). The normalized ketone levels may be highlighted by being displayed in a color different from the color of other normalized ketone levels that are closer to the set value, as a symbol different from the symbol used to depict other normalized ketone levels that are closer to the set value, as being enclosed within a shape (e.g., an oval, a rectangle, etc.), and/or the like. As illustrated in FIG. 20, the normalized ketone levels that are the threshold value greater than the set value are enclosed in ovals A, B, C, D, and E.

Figure 21:
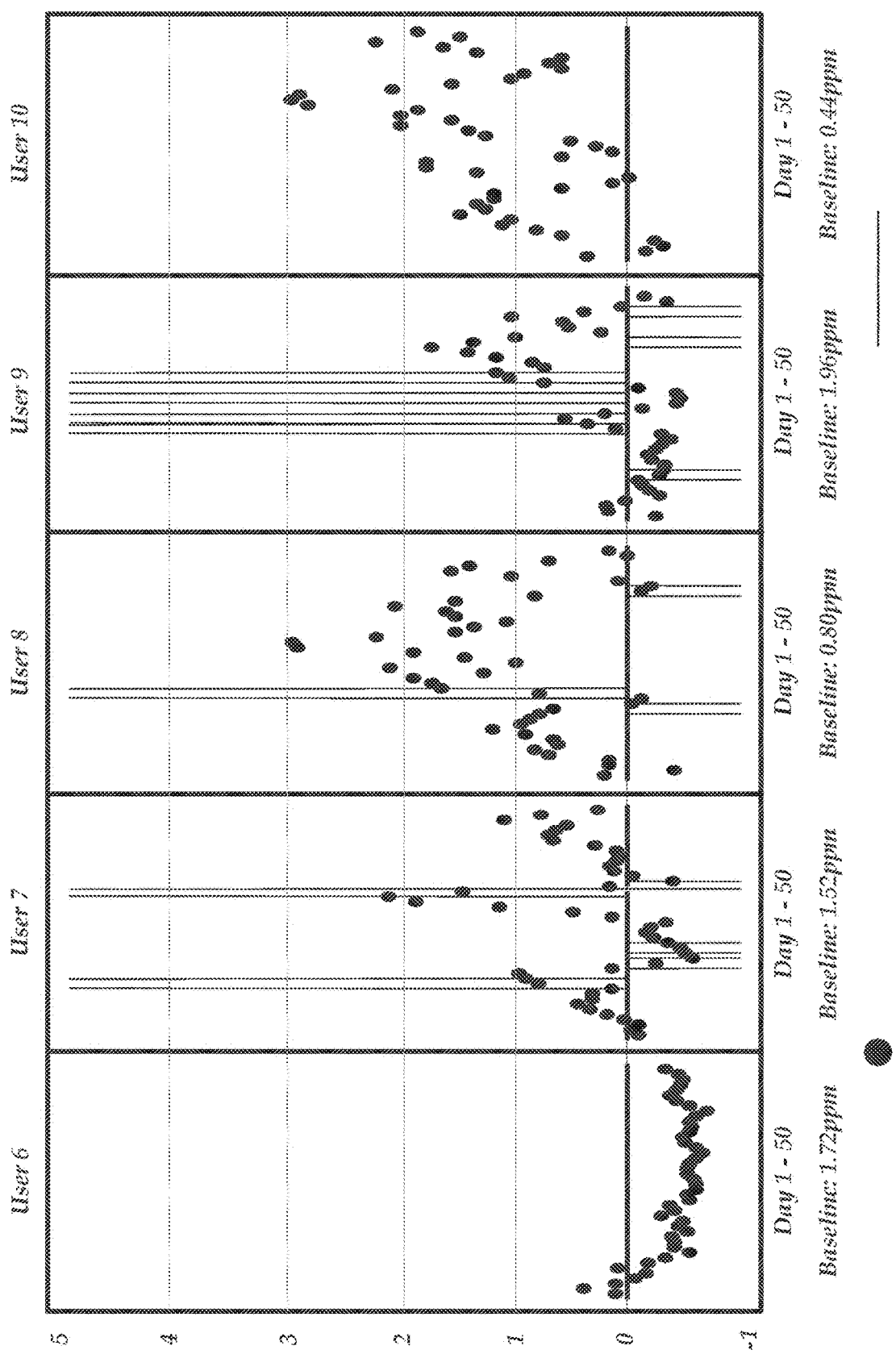
FIG. 21 shows a graphical chart that uses a given algorithm to re-present raw breath acetone levels for enhanced reporting to a healthcare provider.

FIG. 21 shows the response of five individuals who were starting off on a diet program. For example, the baseline breath ketone level for each of the five users may be 1.72 ppm, 1.52 ppm, 0.80 ppm, 1.96 ppm, and 0.44 ppm, respectively. Because each user has different baseline breath ketone levels, the App may normalize the ketone levels such that differences between measured ketone levels and the baseline can be visualized. For example, the App may use Algorithm 6 to normalize the ketone levels, as described above with respect to FIG. 19.

Figure 22:
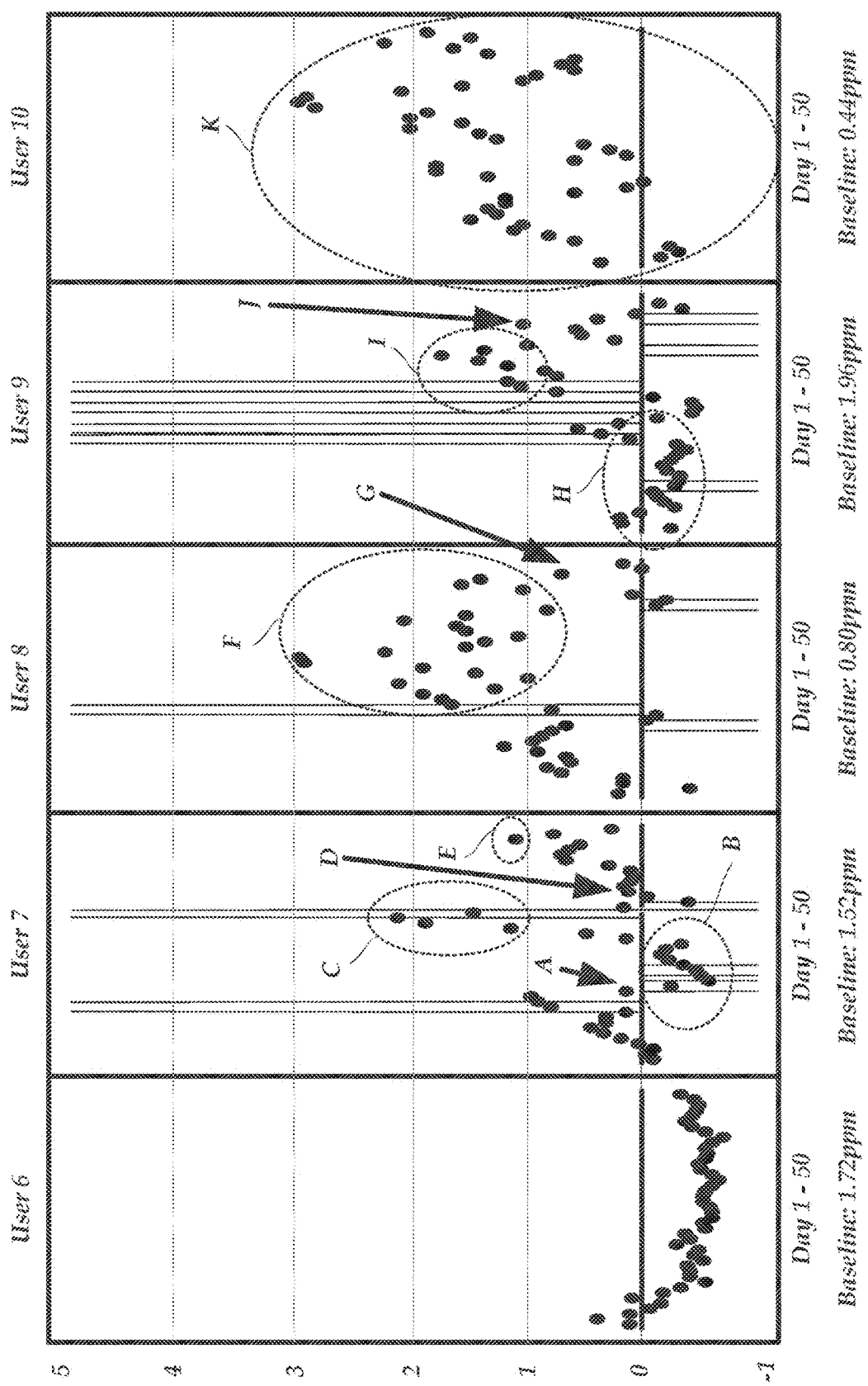
FIG. 22 depicts the data of FIG. 21 with certain features highlighted.

FIG. 22 shows the same data as is presented in FIG. 21, but highlights significant variations in the data. For user 7, events A, B, and D reflect non-compliance. Event E shows the effect of exercise. Event C shows the user's processed ketone levels in response to compliance with the diet program. For user 8, event F reflects the addition of exercise and event G reflects non-compliance. For user 9, event H reflects the user's difficulty controlling the user's diet for several days after a birthday party. Event I reflects the user's improved ketone levels in response to a change in the diet program. Event J reflects the user's non-compliance. For user 10, although the data seems to suggest that the user outperformed the user's baseline, it is important to note that the user's baseline was very low (within the normal range) and that all raw levels were within the normal range. This is an instance in which both the baseline and the processed data should be consulted in tandem. In an embodiment, the App may generate the graphs illustrated in FIG. 22 with annotations identifying and/or describing the various events A-K described above.

Although these processes are useful, this may be too much information for a given user. The App may provide a healthcare provider the option to see more data or to limit the presentation formats of data to the user.

In some embodiments, the measurement device 112 and/or the electronic device 130 (e.g., via the App) update the values of previous breath acetone measurements based on the values of current breath acetone measurements. For example, the App may include a graph that plots breath acetone measurements (or some manipulation of the measurements based on one of the above-described algorithms). As new breath acetone levels are measured, the App may update the graph by revising the values of the previously plotted breath acetone measurements. The values may be revised, for example, such that the graph is more easily understood by the user. In some cases, breath acetone levels may drop due to a trigger point or another event. The drop in breath acetone levels may be gradual and occur over several days because some acetones may take several days to be flushed from the user's body. The user, however, may expect the drop to be sudden and may not understand why the plotted graph shows a gradual drop in breath acetone levels. Thus, if the measured breath acetone levels show a downward trend, with the currently measured breath acetone level at or near an expected trough, the App may revise the graph such that the breath acetone levels measured in one or more days before the current day are depicted as having values that match or nearly match the measured breath acetone level of the current day.

Terminology

All of the actions described herein as being performed by an "electronic device" may be performed under the control of a mobile application, such as the mobile application 2715. All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, and/or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. In some embodiments, the computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on general purpose computer hardware, or combinations of both. To clearly illustrate this interchangeability of hardware and software, various illustrative components, blocks, modules, and steps have been described above generally in terms of their functionality. Whether such functionality is implemented as specialized hardware versus software running on general-purpose hardware depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, and at least one of Z to each be present.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A device-implemented process, comprising:
generating, by a portable ketone measurement device, a sequence of ketone measurements representing ketone levels of a human subject on a carbohydrate-restricted diet; and
by execution of program instructions by one or more processors:
detecting an abnormal pattern in the sequence of ketone measurements, wherein the abnormal pattern comprises a ketone level decline indicating a possible failure of the human subject to adhere to the carbohydrate-restricted diet;
in response to detecting the abnormal pattern, acquiring physiologic parameter data representing a non-ketone physiologic parameter of the human subject;
determining, based at least partly on the acquired physiologic parameter data, whether a corrective action should be taken to address a condition of the human subject associated with failure to comply with the carbohydrate-restricted diet; and
in response to determining that a corrective action should be taken, automatically activating a pump that administers a therapeutic substance into a body of the human subject.

2. The device-implemented process of claim 1, wherein the physiologic parameter data is a measurement of at least one of glucose, hemoglobin A1c, and insulin.

3. The device-implemented process of claim 1, wherein acquiring the physiologic parameter data comprises activating a measurement device that measures the physiologic parameter.

4. The device-implemented process of claim 1, wherein the pump is an insulin pump.

5. The device-implemented process of claim 1, further comprising, in response to determining that a corrective action should be taken, transmitting a notification to a user.

6. The device-implemented process of claim 1, wherein the one or more processors include a processor of a mobile phone that wirelessly communicates with the portable ketone measurement device.

7. The device-implemented process of claim 1, wherein the one or more processors include a processor of a remote server.

8. The device-implemented process of claim 1, wherein the one or more processors include a processor of the portable ketone measurement device.

9. The device-implemented process of claim 1, wherein the one or more processors include a processor of a measurement device that measures the physiologic parameter, the measurement device being separate from the portable ketone measurement device.

10. The device-implemented process of claim 1, wherein the portable ketone measurement device is a breath analysis device that measures ketone levels in breath samples.

11. The device-implemented process of claim 1, wherein generating the sequence of ketone measurements comprises detecting color changes occurring in cartridges through which breath samples are passed.

12. The device-implemented process of claim 1, wherein detecting the abnormal pattern comprises detecting a drop in a ketone level of the human subject below an alarm threshold.

13. The device-implemented process of claim 1, wherein detecting the abnormal pattern comprises determining that multiple ketone measurements of the human subject taken over a selected time period fall below a threshold.

14. The device-implemented process of claim 1, wherein detecting the abnormal pattern comprises detecting a ketone level dip over multiple measurements followed by a ketone level increase.

15. The device-implemented process of claim 1, wherein the human subject is a diabetic, and the process manages effects of diabetes in the human subject by determining when insulin should be administered.

16. A system, comprising:
a portable ketone measurement device configured to analyze bodily fluid samples of a human subject, and to generate ketone measurements representing ketone levels in the bodily fluid samples; and
executable program code, stored in non-volatile memory, that directs one or more processors to perform a process that comprises (1) determining that a sequence of the ketone measurements generated by the portable ketone measurement device follows an abnormal pattern, said abnormal pattern comprising a ketone level decline indicating a possible failure of the human subject to adhere to a carbohydrate-restricted diet, (2) in response to determining that the sequence follows the abnormal pattern, acquiring physiologic parameter data representing a non-ketone physiologic parameter of the human subject, (3) determining whether the physiologic parameter data is consistent with non-adherence to the carbohydrate-restricted diet, and (4) in response to determining that the physiologic parameter data is consistent with non-adherence to the carbohydrate-restricted diet, taking a corrective action.

17. The system of claim 16, wherein determining whether the physiologic parameter data is consistent with non-adherence to the carbohydrate-restricted diet comprises determining whether the physiologic parameter data follows an abnormal pattern corresponding to the abnormal pattern in the sequence of ketone measurements.

18. The system of claim 17, wherein the physiologic parameter data comprises glucose measurements.

19. The system of claim 16, wherein the portable ketone measurement device comprises a wireless transceiver and a processor, and is programmed to use the wireless transceiver to wirelessly transmit the ketone measurements to a mobile device, and the executable program code comprises code of an application that runs on the mobile device.

20. The system of claim 16, wherein at least a portion of the executable program code runs on the portable ketone measurement device.

21. The system of claim 16, wherein the physiologic parameter data comprises a measurement of at least one of the following: glucose, hemoglobin A1c, and insulin.

22. The system of claim 16, wherein taking the corrective action comprises activating a pump that administers a therapeutic substance into a body of the human subject.

23. The system of claim 22, wherein the pump is an insulin pump.

24. The system of claim 16, wherein the corrective action is a transmission of a notification.

25. The system of claim 16, wherein the abnormal pattern comprises a drop in a ketone level of the human subject below an alarm threshold.

26. The system of claim 16, wherein the abnormal pattern comprises multiple ketone measurements falling below an alarm threshold.

27. The system of claim 16, wherein the abnormal pattern comprises a ketone level dip over multiple measurements followed by a ketone level increase.

* * * * *